United States Patent
Hou et al.

(10) Patent No.: US 11,397,229 B2
(45) Date of Patent: Jul. 26, 2022

(54) LOCAL COIL APPARATUS FOR MAGNETIC RESONANCE IMAGING

(71) Applicant: SHANGHAI UNITED IMAGING HEALTHCARE CO., LTD., Shanghai (CN)

(72) Inventors: Xiangming Hou, Shanghai (CN); Zidong Wei, Shanghai (CN); Guangzu Xu, Shenzhen (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/033,928

(22) Filed: Sep. 28, 2020

(65) Prior Publication Data

US 2021/0018580 A1    Jan. 21, 2021

Related U.S. Application Data

(63) Continuation-in-part of application No. 16/442,419, filed on Jun. 14, 2019, now Pat. No. 10,830,847.

(30) Foreign Application Priority Data

Mar. 14, 2019   (CN) .......................... 201910194177.2
Sep. 26, 2019   (CN) .......................... 201910918082.0

(51) Int. Cl.
    *G01R 33/34*    (2006.01)
    *A61B 5/055*    (2006.01)

(52) U.S. Cl.
    CPC ........ *G01R 33/34092* (2013.01); *A61B 5/055* (2013.01); *G01R 33/34084* (2013.01)

(58) Field of Classification Search
    CPC .............. A61B 5/055; A61B 2562/164; G01R 33/34007; G01R 33/341
See application file for complete search history.

(56) References Cited

U.S. PATENT DOCUMENTS

| | | | |
|---|---|---|---|
| 5,221,902 A * | 6/1993 | Jones | G01R 33/34061 |
| | | | 324/318 |
| 5,664,568 A | 9/1997 | Srinivasan et al. | |

(Continued)

FOREIGN PATENT DOCUMENTS

| | | |
|---|---|---|
| CN | 201585986 U | 9/2010 |
| CN | 101950006 A | 1/2011 |

(Continued)

OTHER PUBLICATIONS

First Office Action in Chinese Application No. 201910918082.0 dated Mar. 3, 2022, 21 pages.

(Continued)

*Primary Examiner* — Gregory H Curran
(74) *Attorney, Agent, or Firm* — Metis IP LLC

(57) ABSTRACT

A local coil apparatus for performing a magnetic resonance (MR) scanning on a local part of a subject is provided. The local coil apparatus may include at least one receiving system for receiving the local part. The at least one receiving system may each include an activation member, a receiving member assembly, and a driving mechanism. The receiving member assembly may include one or more receiving members. Each of the one or more receiving members may include a first coil assembly configured to receive MR signals during the MR scanning. The driving mechanism may be physically connected to the one or more receiving members. When the local part is placed on the activation member, the activation member may cause the driving mechanism to drive the receiving member assembly to change from a first configuration to a second configuration to reduce a distance between at least a portion of the first coil assembly and a portion of the local part so that the first coil assembly conforms to the local part.

17 Claims, 28 Drawing Sheets

(56) References Cited

U.S. PATENT DOCUMENTS

| | | | |
|---|---|---|---|
| 6,029,082 A | 2/2000 | Srinivasan et al. | |
| 6,441,612 B1 * | 8/2002 | Shimo | G01R 33/34053 324/307 |
| 6,577,888 B1 | 6/2003 | Chan et al. | |
| 6,591,128 B1 | 7/2003 | Wu et al. | |
| 6,784,665 B1 | 8/2004 | Chan et al. | |
| 6,867,593 B2 | 3/2005 | Menon et al. | |
| 6,980,002 B1 | 12/2005 | Petropoulos et al. | |
| 7,375,527 B2 | 5/2008 | Vaughan, Jr. | |
| 7,518,365 B2 | 4/2009 | Driemel | |
| 7,911,209 B2 | 3/2011 | Alradady et al. | |
| 8,046,046 B2 | 10/2011 | Chan et al. | |
| 8,952,694 B2 | 2/2015 | Biber et al. | |
| 9,138,164 B2 | 9/2015 | Driemel | |
| 9,250,302 B2 | 2/2016 | Driemel et al. | |
| 9,322,891 B2 | 4/2016 | Biber | |
| 2005/0107686 A1 | 5/2005 | Chan et al. | |
| 2008/0097192 A1 | 4/2008 | Driemel | |
| 2011/0260728 A1 | 10/2011 | Biber et al. | |
| 2011/0279119 A1 | 11/2011 | Driemel et al. | |
| 2012/0286784 A1 | 11/2012 | Driemel | |
| 2013/0076358 A1 | 3/2013 | Taracila et al. | |
| 2013/0131498 A1 | 5/2013 | Taracila et al. | |
| 2013/0307540 A1 | 11/2013 | Taracila et al. | |
| 2013/0317346 A1 | 11/2013 | Alagappan et al. | |
| 2014/0005525 A1 | 1/2014 | Chen et al. | |
| 2014/0039301 A1 | 2/2014 | Driemel | |
| 2015/0057527 A1 | 2/2015 | Driemel | |
| 2015/0057528 A1 | 2/2015 | Driemel | |
| 2016/0047868 A1 | 2/2016 | Driemel | |
| 2016/0058397 A1 | 3/2016 | Kim et al. | |
| 2016/0349336 A1 | 12/2016 | Chang et al. | |
| 2017/0143204 A1 | 5/2017 | Johnson et al. | |
| 2018/0070852 A1 | 3/2018 | Azulay et al. | |
| 2018/0356477 A1 | 12/2018 | Lau et al. | |
| 2019/0154775 A1 | 5/2019 | Stack et al. | |

FOREIGN PATENT DOCUMENTS

| | | |
|---|---|---|
| CN | 104473644 A | 4/2015 |
| CN | 204241676 U | 4/2015 |
| CN | 204989437 U | 1/2016 |
| CN | 207679454 U | 8/2018 |
| WO | 2018097863 A1 | 5/2018 |

OTHER PUBLICATIONS

Xin, Xuegang, Intraoperative Magnetic Resonance Radiofrequency Coil Design, Chinese Doctoral Dissertations & Master's Theses Full-text Database (Master) Information Science and Technology, 2011, 96 pages.

* cited by examiner

1900

1910: Positioning the bottom component 216 of the housing 210 on the scanning table 112 of the imaging system 100

1920: Positioning the subject may be positioned on the scanning table 112, ensuring that, for each of the at least one receiving system of the local coil apparatus 200, the local part of the subject is properly placed on the activation mechanism 240 of the receiving system 1930: For each of the at least one receiving system, causing, by the activation mechanism 240, the driving mechanism 250 to drive each of the one or more receiving members 230 to change from the first configuration to the second configuration 1940: Mounting the top component 215 of the housing 210 on the bottom component 216

1950: Causing the scanning table 122 to advance the subject to the scanning region 113 of the scanner 110, so that the local apparatus 200 is inside the scanning region 113

1960: Causing the scanner 110 and the local coil apparatus 200 to together perform an MR scanning on the local part of the subject

FIG. 19

LOCAL COIL APPARATUS FOR MAGNETIC RESONANCE IMAGING

CROSS-REFERENCE TO RELATED APPLICATIONS

This application claims priority of Chinese Application No. 201910918082.0, filed on Sep. 26, 2019, and is a continuation-in-part of U.S. application Ser. No. 16/442,419, filed on Jun. 14, 2019, which claims priority of Chinese Patent Application No. 201910194177.2 filed on Mar. 14, 2019, the entire contents of each of which are hereby incorporated by reference.

TECHNICAL FIELD

This present disclosure relates to an imaging system, and more particularly, relates to a local coil apparatus for magnetic resonance (MR) imaging.

BACKGROUND

During a magnetic resonance (MR) imaging process, a subject to be scanned (e.g., a patient) is placed in a varying magnetic field, and a radiofrequency (RF) coil system can emit excitation RF signals to excite the subject and receive response signals (or be referred to as MR signals) emitted by the excited subject. The received response RF signals are transformed to scan data, which is further processed to generate an MR image of the subject. In many situations, to obtain an MR image of a local part (e.g., the head, a knee) of the subject, a local coil apparatus may be mounted in direct proximity on, below, next to, or in the corresponding part of the subject, so as to improve the signal-to-noise ratio (SNR) of the MR image of the scanned part. Taking the head coil apparatus as an example, the head coil apparatus may be in the form of a hamlet and include a plurality of coils. The scanning of the subject's head can be achieved by the plurality of coils, thereby obtaining an MR image of the head for diagnosis or analysis. However, most of the existing head coil apparatus can't precisely accommodate different sizes of heads. As a result, there are usually gaps between the coils and the head, and the gaps are usually non-negligible. The gaps may affect the MR imaging performance, causing a reduced SNR of the resulting MR image.

Therefore, it is desirable to provide a local coil apparatus capable of precisely accommodate different sizes of heads (or other local parts) to reduce the gaps and improve the imaging performance.

SUMMARY

According to an aspect of the present disclosure, a local coil apparatus for performing a magnetic resonance (MR) scanning on a local part of a subject is provided. The local coil apparatus may include a housing and at least one receiving system for receiving the local part. The housing may provide an inner space for receiving the local part of a subject. The at least one receiving system may each include an activation member, a receiving member assembly, and a driving mechanism. The activation member may be disposed inside the inner space. The receiving member assembly may include one or more receiving members inside the inner space. Each of the one or more receiving members may include a first coil assembly configured to receive MR signals during the MR scanning. The driving mechanism may be physically connected to the one or more receiving members. When the local part is placed on the activation member, the activation member may cause the driving mechanism to drive the receiving member assembly to change from a first configuration to a second configuration to reduce a distance between at least a portion of the first coil assembly and a portion of the local part so that the first coil assembly conforms to the local part.

In some embodiments, the receiving member assembly in the second configuration may be in closer conformity to the local part than in the first configuration.

In some embodiments, for at least one receiving member of the one or more receiving members: the driving mechanism may include a first rod and a second rod; the first rod may be connected to the driving mechanism; the first rod may be directly or indirectly connected to the second rod; the second rod may be connected to the at least one receiving member; and when the local part is placed on the activation member, the first rod may be driven, by the activation member, to move with respect to the activation member, and the first rod may cause the second rod to push the at least one receiving member toward the local part, causing a configuration change of the at least one receiving member.

In some embodiments, the first rod and the second rod may be pivotally connected via a first connecting shaft, and the second rod may be configured to rotate with respect to the first rod via the first connecting shaft.

In some embodiments, an elastic component may be disposed at the first connecting shaft. The elastic component may cause the second rod to rotate along with the first rod when the at least one receiving member is not in contact with the local part, and the elastic component may also cause the second rod to rotate relative to the first rod when the configuration change of the at least one receiving member is obstructed by the local part while the activation member is still causing the driving mechanism to drive the at least one receiving member.

In some embodiments, the elastic component may be a torsion spring connecting the first rod and the second rode.

In some embodiments, when the local part is placed on the activation member, the activation member may be pressed down by the local part, causing the configuration change of the at least one receiving member.

In some embodiments, the first rod may be connected to the activation member via a second connecting shaft. When the local part is pressing down the activation member, the first rod may be pulled by the activation member to move relative to the second connecting shaft, causing the second rod to move along with the first rod to push at least one receiving member toward the local part.

In some embodiments, the at least one receiving system may include a first receiving system and a second receiving system. The first receiving system may be configured to receive a first portion of the local part. The second receiving system may be configured to receive a second portion of the local part.

In some embodiments, the first portion may include at least a portion of the head of a patient, and the second portion may include at least a portion of the neck of the patient.

In some embodiments, the activation member of the first receiving system and the activation member of the second receiving system may be an integral structure.

In some embodiments, at least one of the one or more receiving members may include a flexible component. When the receiving member assembly is in the second configuration, the flexible component of at least one receiving member may undergo an elastic deformation and be caused to press against at least a portion of the local part.

In some embodiments, the first coil assembly of the receiving member may be disposed inside the flexible component.

In some embodiments, the housing may includes a first component and a second component. The first component may be configured to be positioned on a table of an MR imaging system. The first component and the second component may be detachably mounted together to form a chamber to provide the inner space for receiving the local part. The at least one receiving system may be mounted on the first component.

In some embodiments, the first component may include a movable scan section. The movable scanning section may include a third coil assembly and is movable with respect to the first component to conform to a portion of the local part.

In some embodiments, the housing may include a second coil assembly. The second coil assembly may be configured to receive MR signals during the MR scanning. The second coil assembly may have a fixed configuration with respect to the housing.

According to another aspect of the present disclosure, a magnetic resonance (MR) imaging system is provided. The MR imaging system may include a medical device, a data processing device, and a local coil apparatus. The medical device may include a scanner and a table. The scanner may be configured to perform an MR scanning in a scanning region provided by the scanner and obtain MR scan data resulting from the MR scanning. The table may be configured to support a subject and advance the subject to the scanning region. The data processing device may be in communication with the MR medical device, and be configured to generate an MR image based on the MR scan data. The local coil apparatus may include a housing, at least one receiving system for receiving the local part, and a communication module. The housing may include a first component and a second component. The first component may be configured to be positioned on the table. The housing may provide an inner space for receiving a local part of a subject. The at least one receiving system may each include an activation member, a receiving member assembly and a driving mechanism. The activation member may be disposed inside the inner space. The receiving member assembly may include one or more receiving members inside the inner space. Each of the one or more receiving members may include a first coil assembly. The first coil assembly may be configured to receive MR signals during the MR scanning. The driving mechanism may be physically connected to the one or more receiving members. When the local part is placed on the activation member, the activation member may cause the driving mechanism to drive the receiving member assembly to change from a first configuration to a second configuration to reduce a distance between at least a portion of the the first coil assembly and a portion of the local part so that the first coil assembly conforms to the local part. The communication module may be configured to transmit the MR signals or data generated based on the MR signals to the medical device or the data processing device.

In some embodiments, when the local part is placed on the activation member, the activation member may be pressed down by the local part. For at least one receiving member of the one or more receiving members: the driving mechanism may include a first rod and a second rod; the second rod may be connected to the at least one receiving member; the first rod and the second rod may be pivotally connected via a first connecting shaft; the first rod may be connected to the activation member via a second connecting shaft; an elastic component may be disposed at the first connecting shaft; when the local part is pressing down the activation member, the first rod may be pulled by the activation member to rotate about the second connecting shaft, causing the second rod to move with the first rod to push the at least one receiving member toward the local part, so as to cause a configuration change of the at least one receiving member. The elastic component may cause the second rod to move with the first rod when the receiving member is not in contact with the local part. The elastic component may also cause the second rod to rotate relative to the first rod when the configuration change of the at least one receiving member is obstructed by the local part.

In some embodiments, the medical device may be a multi-modality scanner including an MR imaging modality and another imaging modality. The local coil apparatus may include one or more materials that have have limited influence on the another imaging modality.

In some embodiments, the housing may include a second coil assembly configured to receive MR signals during the MR scanning. The second coil assembly may have a fixed configuration with respect to the housing.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTIONS OF THE DRAWINGS

The present disclosure is further described in terms of example embodiments. These example embodiments are described in detail with reference to the drawings. These embodiments are non-limiting examples, in which like reference numerals represent similar structures throughout the several views of the drawings, and wherein:

FIG. 19 is a flow chart illustrating an exemplary process for performing an MR imaging on a local part of a subject with the imaging system illustrated in FIG. 1 according to some embodiments of the present disclosure;

DETAILED DESCRIPTION

Figure 1:
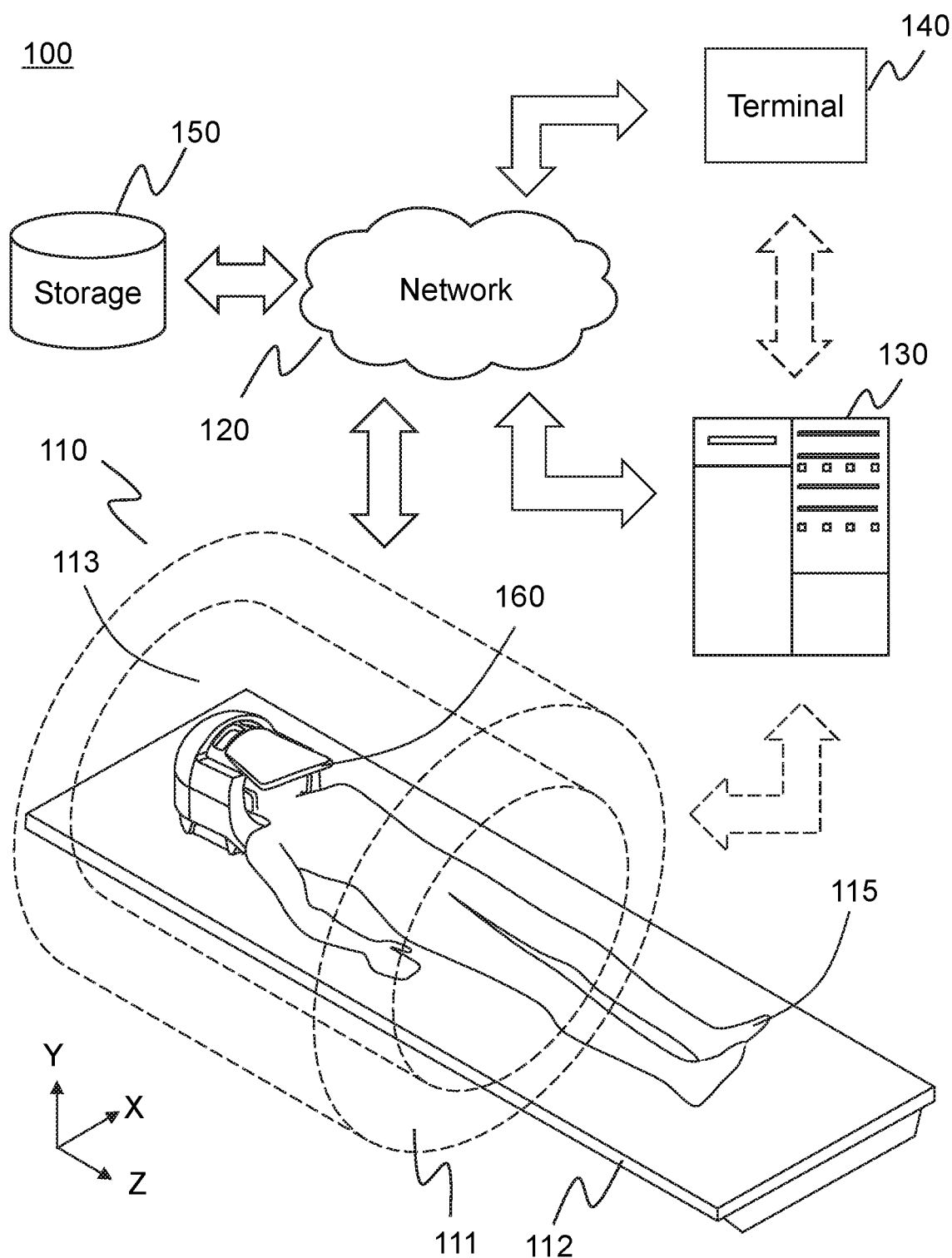
FIG. 1 is a schematic diagram illustrating an exemplary imaging system according to some embodiments of the present disclosure.

The present disclosure provides a local coil apparatus for performing an MR scanning on a local part of a subject, such as the head of a patient. The local coil apparatus includes a receiving system configured to reduce the distances between the coils of the local coil apparatus and the local part received by the local coil apparatus to improve the MR imaging performance. The receiving system is also adaptive to local parts of different subjects with different shapes/sizes.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise", "comprises", and/or "comprising", "include", "includes", and/or "including", when used in this specification, specify the presence of stated features, integers, steps, operations, elements, and/or components, but do not preclude the presence or addition of one or more other features, integers, steps, operations, elements, components, and/or groups thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements (for example, between layers) are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent").

It should also be understood that terms such as "top," "bottom," "upper," "lower," "vertical," "lateral", "longitudinal" "above," "below," "upward(s)," "downward(s)," "left," "right," and other such spatial reference terms are used in a relative sense to describe the positions or orientations of certain surfaces/parts/components of the apparatus in relation to other such features of the apparatus when the apparatus is in a normal operating position, and may change if the position or orientation of the apparatus changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure.

FIG. 1 is a schematic diagram illustrating an exemplary imaging system 100 according to some embodiments of the present disclosure. The imaging system 100 may include a medical device 110, a network 120, a data processing device 130, one or more terminals 140, and a storage device 150.

The medical device 110 may be an MR device for scanning a subject so as to generate an MR image of the patient. The medical device 110 may be a single modality scanner or a multi-modality scanner (e.g., an MR-Positron emission tomography (PET) scanner). Correspondingly, the MR image may be a normal MR image or a multi-modality image including an MR image component. As used herein, the term "image" may generally refer to a normal image, a video, a video frame, a spectrum, or the like, or a combination thereof. The image may be a two-dimensional (2D) image, a three-dimensional (3D) image, or an image of a higher dimension. The subject may include a biological object and/or a non-biological object. For example, a biological object may be a human being, an animal, a plant, or the like, or a portion thereof (e.g., a cell, a tissue, an organ). A non-biological object may be or may include a radioactive ore, an antique, luggage, etc. The medical device 110 may obtain scan data of the subject via the scanning. The data processing device 130 may obtain the scan data from the medical device 110 and process the scan data to obtain the corresponding image.

The medical device 110 may include a scanner 111 and a table 112. The scanner 111 may be in the form of a hollow cylinder, which may provide an inner space as a scanning region 113. The scanner 111 may include a magnet assembly, a gradient coil assembly, and an RF coil assembly (not shown in FIG. 1). In some embodiments, the medical device 110 may be a multi-modality scanner including an MR imaging modality and another imaging modality (e.g., a PET imaging modality). In such embodiments, the scanner 111 may further include other imaging components (e.g., PET detection rings). To perform an MR scanning on a subject 115 (e.g., a patient), the subject 115 may be placed on the table 112, and the table 112 may be configured to support the subject and advance the subject to the scanning region 113, so as to perform an MR scanning on the subject 115.

Positions of the scanning region 113 may be represented by coordinates with respect to a Cartesian coordinate system as shown in FIG. 1. The Cartesian coordinate system may include an X axis, a Y axis, and a Z axis, directions of which may be referred to as an X direction, a Y direction, and a Z direction. Coordinates of a point in the scanning region 113 may be mapped to a voxel/pixel in the resulting MR image.

The magnet assembly may be configured to generate a static magnetic field (or be referred to as a main magnetic field) in the scanning region 113. The static magnetic field may polarize the subject 115 for MR imaging. The static magnetic field may be in the Z direction. The magnet assembly may be or may include a permanent magnet, a superconducting electromagnet, a resistive electromagnet, etc. The magnet assembly may have any magnetic field intensity, for example, 0.2 Tesla, 0.5 Tesla, 1.0 Tesla, 1.5 Tesla, and 3.0 Tesla. In some embodiments, the magnet assembly may further include shim coils for enhancing the homogeneity of the magnetic field.

The gradient coil assembly may generate magnetic field gradient pulses for localizing MR signals (e.g., for phase encoding or frequency encoding). The magnetic field gradient pulses may be in the X direction, the Y direction, and/or the Z direction. The magnetic field gradient pulses may form one or more gradient magnetic fields. The gradient coil assembly may form part of the magnet assembly or be independent of the magnet assembly.

The RF coil assembly may generate RF signals to excite the subject and receive the MR signals responding to the RF signals. The MR signals detected by the RF coil assembly may be used to generate MR scan data, e.g., in the form of one or more K-space datasets. The MR scan data may further be processed by the data processing device 130 to generate an MR image.

In some embodiments, to scan a local part of the subject 115, such as the head, the neck, a knee, the abdomen, a limb, an ankle, a hand, a foot, etc., of the subject 115, a local coil apparatus 160 may be mounted in direct proximity on, below, next to, or in the corresponding part of the subject, so as to improve the signal-to-noise ratio (SNR) of the MR image of the scanned part. The local coil apparatus 160 may include a plurality of coils configured to specifically receive MR signals of the corresponding local part of the subject 115. The local coil apparatus 160 may be in any proper form. For example, the local part of the subject 115 may be the head of the subject 115, then the local coil apparatus 160 may be in the form of a headgear for receiving the head of the subject 115, and may include a plurality of coils specifically configured to scan the head of a patient. Detailed descriptions of the local coil apparatus 160 may be found elsewhere in the present disclosure (e.g., in connection with FIG. 2A)

During the scanning of the local part (e.g., a head), coils of the local coil apparatus 160 may receive MR signals emitted by the local part. The MR signals may be transformed (e.g., by the local coil apparatus 160, the medical device 110, or the data processing device 130) into corresponding MR scan data. The scan data may be transmitted to the data processing device 130 for generating an MR image of the local part. Compared to the RF coil assembly inside the scanner 111 of the medical device 110, the local coil apparatus 160 may provide better imaging performance toward the local part.

In some embodiments, the local coil apparatus 160 may include a communication module (now shown) configured to transmit the received MR signals or data generated based on the MR signals to the medical device 110 or the data processing device 130. For example, the communication module may directly transmit the received MR signals to the medical device 110 or the data processing device 130. As another example, the local coil apparatus 160 may include a component (e.g., an analog-to-digital converter) to obtain digital data based on the received MR signals, and the communication module may transmit the digital data to the medical device 110 or the data processing device 130.

It is noted that when the medical device 110 is a multi-modality scanner including an MR imaging modality and another imaging modality, the materials of the local coil apparatus may have limited influence on the other imaging modality so that the quality of the image obtained based on scan data of the other imaging modality is acceptable. For example, when the medical device 110 is an MR-PET medical device, at least the scanner of the local coil apparatus 160 (and also coils thereof in some embodiments) is made of gamma-photon-permeable materials.

In some embodiments, the medical device 110 may also include another functioning component, such as a radiation emitter. For example, the medical device 110 may be an MR-radiation therapy (RT) device. Correspondingly, at least the body of the local coil apparatus 160 (and also coils thereof in some embodiments) is made of X-ray-permeable materials.

The network 120 may include any suitable network that can facilitate the exchange of information and/or data for the imaging system 100. Components of the imaging system 100 (e.g., the medical device 110, the terminal 140, the data processing device 130, the storage device 150) may communicate information and/or data with each other via the network 120. The network 120 may be a wired network (e.g., an Ethernet network), a wireless network (e.g., a cellular network, a Wi-Fi network), or the like or a combination thereof. In some embodiments, the network 120 may further include one or more network access points such as base stations and/or internet exchange points.

The data processing device 130 may process data and/or information obtained from the medical device 110, the terminal 140, and/or the storage device 150. For example, the data processing device 130 may be in communication with the medical device 110 and configured to generate an MR image based on the MR scan data obtained from the medical device 110. For example, the MR scan data may be normal MR scan data, and the MR image may be a normal MR image. As another example, the MR scan data may include normal MR scan data and scan data obtained via another imaging modality, such as PET scan data. Then the generated MR image may be a multi-modality image, such as an MR-PET image obtained by fusing the corresponding MR image and PET image. The data processing device 130 may also be configured to control one or more components of the imaging system 100. For example, the data processing device 130 may be configured to control the medical device 110 to scan the subject 115 for MR imaging.

The terminal 140 may be configured to display information to a user and/or receive instructions of the user. For example, the terminal 140 may receive instructions for MR imaging from a user, transmit the instructions to the data processing device 130 to initiate a scanning by the medical device 110, and display the obtained MR image to the user. The terminal 140 may include a mobile phone, a tablet computer, a laptop computer, a wearable device, a virtual reality device, an augmented reality device or the like, or any combination thereof. In some embodiments, the terminal 140 may be a part of the data processing device 130, such as a remote controller of the data processing device 130, a display screen, a mouse, a keyboard, a microphone, a loudspeaker, or the like, or a combination thereof.

The storage device 150 may store any data and/or instructions associated with the imaging system 100. For example, the storage device 150 may store scan data or MR images obtained by the imaging system 100. As another example, the storage device 150 may store instructions to be executed by the data processing device 130 for processing scan data obtained by the medical device 110.

It is noted that the above descriptions about the imaging system 100 are only for illustration purposes, and not intended to limit the present disclosure. After learning the major concept and the mechanism of the present disclosure, a person of ordinary skill in the art may alter the imaging system 100 in an uncreative manner. The alteration may include combining and/or splitting modules or sub-modules, adding or removing optional modules or sub-modules, etc. All such modifications are within the protection scope of the present disclosure.

Figure 2A:
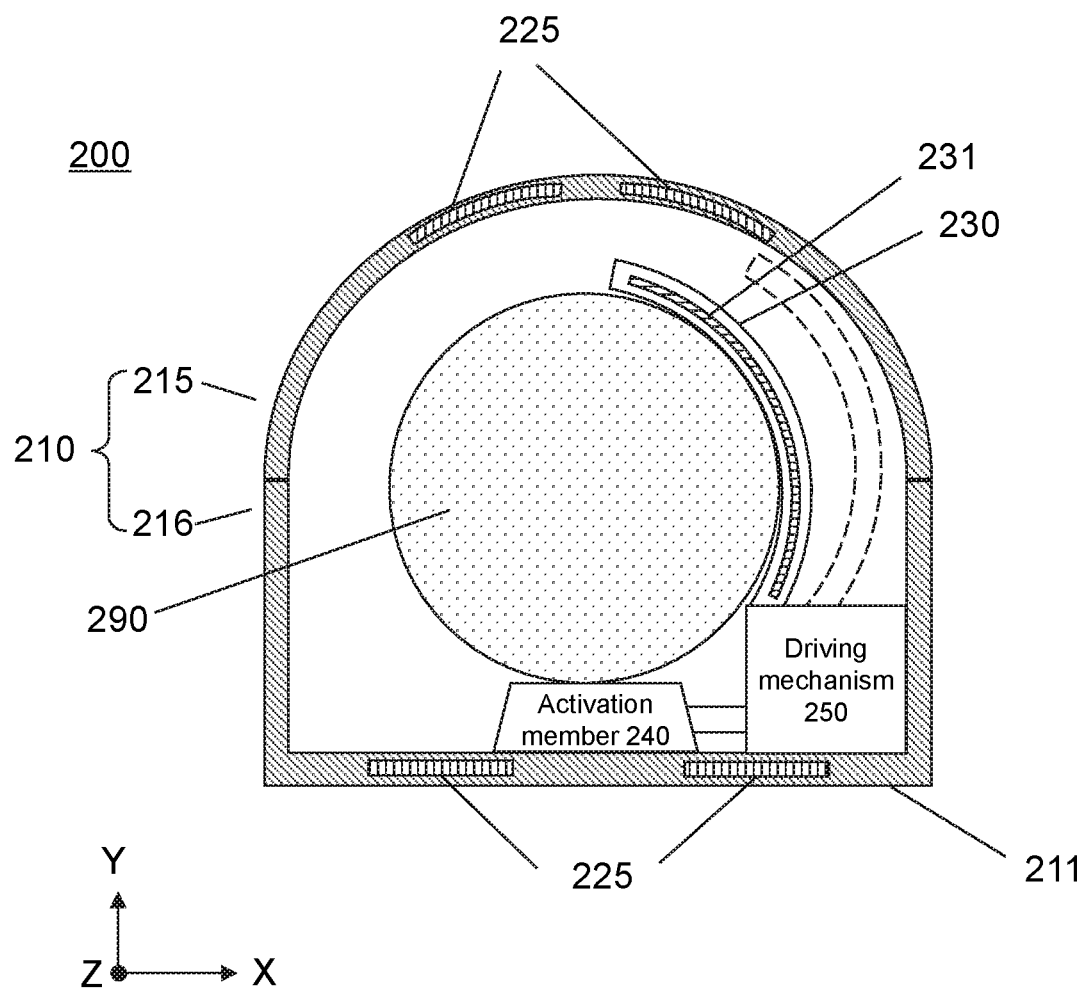
FIG. 2A is a schematic diagram illustrating an exemplary local coil apparatus 200 according to some embodiments of the present disclosure.

FIG. 2A is a schematic diagram illustrating an exemplary local coil apparatus 200 according to some embodiments of the present disclosure. The local coil apparatus 200 is an example of the local coil apparatus 160. The local coil apparatus 200 may be used to perform a local MR imaging on a local part 290 of a subject. In some embodiments, when the subject 115 is a human, the local part 290 may be the head, a knee, an ankle, the abdomen, a hand, a foot, etc., of the subject 115. Compared to other existing local coil apparatuses, the local coil apparatus 200 may accommodate to the corresponding local part 290 of any reasonable size/shape. The local coil apparatus 200 may include mechanisms configured to reduce the gaps (or distances) between the coils and the local part 290 of any size/shape, so as to further improve the imaging performance.

For demonstration purpose, the Cartesian coordinate system shown in FIG. 1 may be used for demonstrating the relative positions of the components of the local coil apparatus 200 or an embodiment thereof.

The local coil apparatus 200 may include a housing 210. The housing 210 may include at least one material which may provide sufficient mechanical strength, so that the housing 210 may provide mechanical support to other components of the local coil apparatus 200. The housing 210 may also allow penetration of RF signals and magnetic fields generated by the medical device 110 so that the MR imaging is enabled. In some embodiments, the housing 210 may include a substantially flat surface (e.g., the surface 211) so that the local coil apparatus 200 may be steadily placed on the table 112. Alternatively or additionally, the housing 210 may include a mounting structure to mount the local coil apparatus 200 on the table 112, so that the local part 290 may not move during the MR scanning.

The housing 210 may be in the form of a receiving chamber providing an inner space for receiving the local part 290. The housing 210 may also provide mechanical support to other components of the local coil apparatus 200.

The local coil apparatus 200 may also include at least one receiving system for receiving the local part. Each of the at least one receiving system is configured to receive a corresponding portion of the local part 290. For example, the local coil apparatus 200 may include a first receiving system for receiving a first portion of the local part 290 and a second receiving system of receiving a second portion of the local part 290. In some embodiments, the local coil apparatus 200 may be a head coil apparatus, and the local part 290 may include the head and the neck of a patient (e.g., the body above shoulders). Then the above first portion may include at least a portion of the head of a patient, and the second portion may include at least a portion of the neck of a patient.

Each of the at least one receiving system may include a receiving member assembly, an activation member 240, and a driving mechanism 250. For demonstration purposes, only one receiving system is illustrated in FIG. 2A and is to be described in detail as following.

The receiving member assembly may include one or more movable/rotatable/bendable receiving members 230 arranged inside the inner space provided by the housing 210. The configuration of each of the one or more receiving members 230 may be changeable to comfort to a corresponding portion of the local part 290. For example, the one or more receiving members 230 may be movable, rotatable, and/or bendable toward the local part 290 to receive the local part 290. For demonstration purposes and not intended to be limiting, only one receiving member 230 is illustrated in FIG. 2A.

The one or more receiving members 230 may be physically supported by the housing 210. In some embodiments, the one or more receiving member 230 may be connected to the inner surface of the housing 210. Each of the one or more receiving members 230 may include a first coil assembly 231 formed by one or more coils. The first coil assembly 231 may be disposed on the surface of or be embedded in the corresponding receiving member 230, and may be moved along with the receiving member 230.

When the local coil apparatus 200 is in a state (or be referred to as a scanning state) for performing an MR scanning (e.g., when the installation of the local coil apparatus 200 on the subject 115 is completed), the receiving member assembly may change from a first configuration to a second configuration. In the second configuration, at least a portion of the receiving member assembly may be in closer conformity to the local part than in the first configuration. After the configuration change, the distance between at least a portion of the first coil assembly 231 thereof and a corresponding portion of the local part 290 may be reduced. When the receiving member assembly is in the second configuration, the first coil assemblies 231 thereof may together form at least a part of a combined coil assembly for performing the MR scanning on the local part 290.

As used herein, the inner surface of the housing 210 may be the surface facing the local part 290, and the outer surface of the shell may be the surface away from the local part 290.

During the configuration change of the receiving member assembly, the one or more receiving members 230 may also have their respective configuration changes. After the configuration change, each of the one or more receiving members 230 may be in closer conformity to the local part 290, so that the distance between the first coil assembly 231 thereof and a corresponding portion of the local part 290 may be minimized. It is noted that when the local coil apparatus 200 includes multiple receiving members 230, the extents of the configuration changes of the multiple receiving members 230 may be the same or different, depending on the size/shape of the local part 290. It is also noted that the one or more receiving members 230 may have substantially the same structure/shape/size or different structures/shapes/sizes.

In some embodiments, the receiving member assembly may further include one or more other members for receiving the local part 290 and/or performing the MR imaging on the local part 290. For example, the receiving member assembly my include one or more movable/rotatable/bendable receiving members (or be referred to as limiting members, not shown) including no coils. The one or more limiting members may be configured to further limit the movement of the local part 290 and/or another local part (e.g., a local part doesn't need an MR scanning) of the subject 115, so that the local part 290 may be kept in still during the MR imaging to reduce artifacts. The one or more limiting members may be drying by the driving mechanism 250, by another independent driving mechanism, or be operated manually by an operator of the imaging system 100. As another example, the receiving member assembly may include one or more coil-including members (not shown), each of which may have a fixed configuration (i.e., have no configuration change) with respect to the housing 210. The one or more coil-including members may support the one or more receiving members 230 and/or guide the local part 290 to be placed on the activation member 240. As a futher example, the receiving member assembly may include one or more movable/rotatable/bendable coil-including receiving members (not shown), which may be drying by another driving mechanism, or be operated manually by an operator of the imaging system 100.

In some embodiments, the local coil apparatus 200 may further include a second coil assembly 225 formed by one or more coils. The second coil assembly 225 may be disposed on the inner surface or the outer surface of the housing 210, or be embedded in the housing 210. Compared to the first coil assembly 231, the second coil assembly 225 may have a fixed configuration (e.g., shape, structure, position) with respect to the housing 210. After the configuration change of the one or more receiving members 230, the first coil assemblies 231 and the at least one second coil assembly 225 may together form a combined coil assembly (or at least a part thereof) for performing the MR scanning on the local part 290. In some embodiments, the at least one second coil assembly 225 may be optional and be removed from the local coil apparatus 200.

The activation member 240 may be disposed inside the inner space provided by the housing 210. When the local part 290 is received by the housing 210, a portion of the local part 290 may be placed on the activation member 240, and the activation member 240 may be triggered by the local part 290. The driving mechanism 250 may be physically connected to the one or more receiving members 230. When the local part is placed on the activation member 240, the activation member 240 may cause the driving mechanism 250 to drive the receiving member assembly to change from the first configuration to the second configuration. For example, the activation member 240 may activate the driving mechanism 250. The activated driving mechanism 250 may exert a driving force on each of the one or more receiving member 230 to cause the configuration change.

In some embodiments, the activation member 240 may exert an activation force to the driving mechanism 250 when the local part 290 is placed thereon. The driving mechanism 250 may include a plurality of driving elements, such as one or more rods, belts, gears (e.g., mechanical gears and/or magnetic gears), springs (e.g., torsion spring), bears, or the like, or a combination thereof. The driving elements of the driving mechanism 250 may operate together to transmit the activation force from the activation member 240 to one or more receiving members 230. The transmitted activation force may be the aforementioned driving force. In different embodiments, to transmit the force, the driving mechanism 250 may include at least one of a magnetic coupled driving mechanism, a hydraulic driving mechanism, a pneumatic driving mechanism, an electro-mechanical driving mechanism, or a mechanical driving mechanism.

The activation member 240 may have various forms and activation mechanisms. In some embodiments, when the local part 290 is placed on the activation member 240, the local part 290 may exert a force (e.g., the gravity force) to the activation member 240, and the activation member 240 may transmit the force exerted by the local part 290 to the driving mechanism 250 as the activation force (with or without a reduction of the force), and the configuration changes of the one or more receiving members may be resulting from the force exerted by the local part 290. In some embodiments, the activation member 240 may include an electric motor and a triggering mechanism to turn on (or turn off) the electric motor. For example, the triggering mechanism may be or may include a pressing button/plate serving as a switch of the electric motor. When the local part 290 is placed on the activation member 240, the pressing button/plate may be pressed down, and the electric motor may be switched on. As another example, the activation member 240 may include a first sensor for sensing the distance between the local part 290 and the first sensor. When the distance is below a predetermined threshold, the first sensor or a processor in communication with the first sensor may transmit a control signal to the electric motor, causing the electric motor to be turned on. The activation member 240 (or the driving mechanism 250) may further include a properly designed transformation mechanism to transform the mechanic energy generated by the electric motor to the activation force to activate the driving mechanism 250.

In the above embodiments, optionally, when the local part 290 is placed on the activation member 240, the activation member 240 may be pressed down by the local part 290, causing the configuration change of the receiving member assembly. For example, due to the gravity force of the local part 290, the pressed activation member 240 may pull a component of the driving mechanism 250 to activate the driving mechanism 250. As another example, the whole body of the activation member 240 may be made as a pressing button to switch on an electric motor to activate the driving mechanism 250.

In some embodiments, the activation member 240 may include one or more coils (optionally) for performing the MR scanning.

Figure 2B:
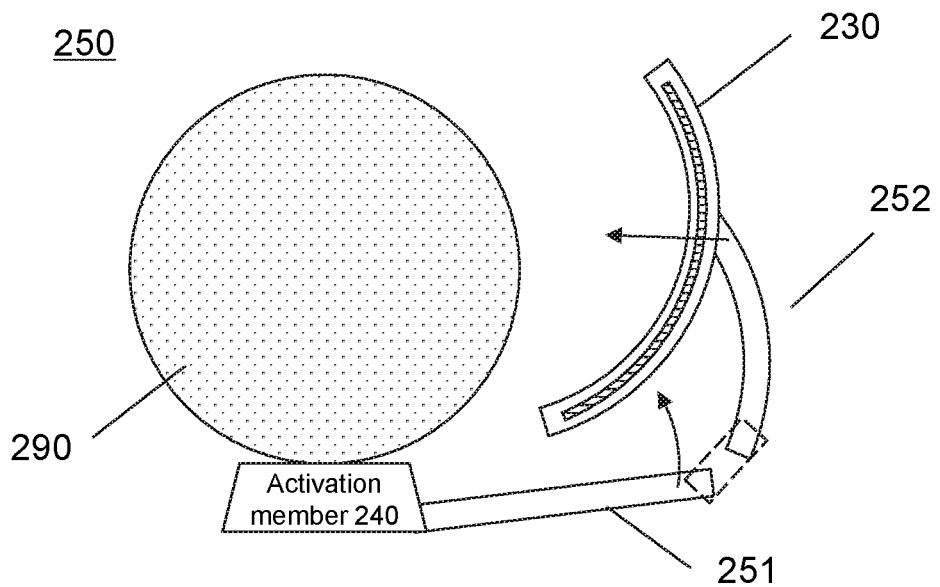
FIGS. 2B and 2C are schematic diagrams illustrating a driving mechanism of the local coil apparatus illustrated in FIG. 2A according to some embodiments of the present disclosure.
Figure 2C:
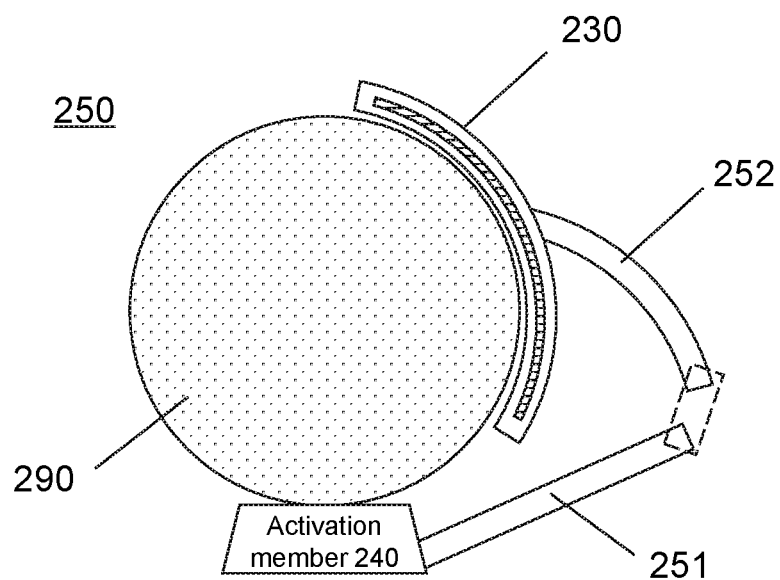

FIGS. 2B and 2C are schematic diagrams illustrating the driving mechanism 250 of the local coil apparatus 200 illustrated in FIG. 2A according to some embodiments of the present disclosure. For at least one of the one or more receiving members 230 in a receiving system, the driving mechanism 250 may include at least a first rod 251 and a second rod 252. For demonstration purposes, only one receiving member 230 and the corresponding first/second rod 251/252 is illustrated in FIGS. 2B and 2C, and is to be further described as following. The first rod 251 may be connected to the activation mechanism 240, and may be directly or indirectly connected to the second rod 252. The second rod 252 may be connected to at least one receiving member 230 of the receiving member assembly. When the local part 290 is placed on the activation member 240, the first rod 251 may be driven, by the activation member 240, to move (e.g., rotate) relative to the activation member 240. The first rod 251 may cause, via the direct or indirect connection, the second rod 252 to push the at least one receiving member 230 toward the local part 290, causing the configuration change of the at least one receiving member 230.

In some specific embodiments, for each of the one or more receiving members 230, the driving mechanism 250 may include at least a first rod 251 and a second rod 252 for driving the configuration changes of the one or more receiving members 230.

In some embodiments, the second rod 252 may be coonnected to a single receiving member 230.

In some embodiments, the second rod 252 may be connected to multiple receiving members 230, and may drive the configuration changes of the multiple receiving members 230 concurrently.

In some embodiments, the first rod 251 and the second rod 252 may be directly connected. For example, the first rod 251 may be pivotally connected to the second rod 252 via, e.g., a connecting shaft (first connecting shaft, not shown in FIGS. 2A to 2C), and the second rod 252 may be configured to rotate with respect to the first rod 251 via the connecting shaft, so that the configuration change of the receiving member 230 may be performed smoothly.

In some embodiments, an elastic component (not shown in FIGS. 2A to 2C) may be disposed at the connecting shaft. The elastic component may cause the second rod 252 to move (e.g., rotate) along with the first rod 251 when the receiving member is not in contact with the local part 290. Under such a situation, the elastic component may provide a strengthening force to strengthen the connection between the first rod 251 and the second rod 252, and the second rod 252 and the first rod 251 may be viewed as an integrated structure. The elastic component may also cause the second rod 252 to move (e.g., rotate) relative to the first rod 251 when the configuration change of the receiving member 230 has obstructed by the local part 290 and the activation member 240 further causes the driving mechanism 250 to drive the receiving member 230. For example, under such a situation, the activation member 240 may continue to provide an activation force (e.g., resulted from the gravity force exerted by the local part 290, generated by an electric motor) to the driving mechanism 250. Consequently, the receiving member 230 may be pressed tighter against the local part 290 by the driving mechanism (or the second rod 252), and the local part 290 may exert a stronger feedback force back to the receiving member 230, which may be transmitted to the elastic component and overwhelm the strengthening force provided by the elastic component, causing the second rod 252 to move (e.g., rotate) relative to the first rod 251. The elastic component may enable the driving mechanism 250 to adapt to local part 290 of different sizes and/or shapes, and avoid a possible accident caused by an oversized local part 290 or a malfunction of the activation member 240.

In some embodiments, the elastic component may include at least one of a normal spring, a torsion spring, a rubber band, an elastic belt, or the like, or a combination thereof. An example of the elastic component, the first rod, and the second rod are provided in connection with FIGS. 11 to 15.

In some embodiments, the first rod 251 and the second rod 252 may be indirectly connected via one or more other driving components, such as a rod, a gear, a belt, magnetic coupling components, or the like, or a combination thereof. The driving mechanism 250 may have any proper configuration to allow the rotated first rod 251 to drive the second rod 252 to change the configuration of the receiving member 230. In some specific embodiments, at least two of the components of the driving mechanism 250 may be connected via an aforementioned elastic component.

In some embodiments, a guiding system (now shown) may be introduced into the driving mechanism 250 to guide the rotation/move of the first/second rod 251/252, so that the first/second rod 251/252 may move (e.g., rotate) along a fixed trajectory, and the steady of the driving mechanism 250 may be improved. For example, the guiding system may include one or more of a guiding slot, a guiding rod, a stop block (for limiting the rotation/moving range), a magnet, or the like, or a combination thereof. The guiding system may also provide mechanic support to the first/second rod 251/252.

Referring back to FIG. 2A, during the configuration change the receiving member assembly from the first configuration to the second configuration, at least one of the shape, the position, or the structure of each of the one or more receiving members 230 thereof may be adjusted automatically, so that the receiving member may have closer conformity toward the local part 290. For each of the one or more receiving members 230, when the receiving member assembly is in the first configuration, the receiving member 230 may be in a position/shape/structure that facilitate the local part 290 (even in a biggest reasonable size) to be received by the housing 210 and be placed on the at least one activation member 240 (e.g., the broken lines in FIG. 2A); when the receiving member assembly is in the second configuration, the receiving member 230 may be automatically adjusted toward the local part 290 to reduce the distance between the corresponding first coil assembly 231 and the local part 290 (e.g., the receiving member 230 as shown in FIG. 2A). For example, the receiving member 230 may be moved/bent/rotated away from the inner surface of the housing 210, so as to reduce the distance between the first coil assembly 231 thereof and the local part 290. In some embodiments, when the receiving member assembly in the second configuration, each receiving member 230 thereof may be in contact with the local part 290. Under such a situation, the distance between the first coil assembly 231 of each receiving member 230 and a corresponding portion of the local part 290 may be minimized, and the movement of the local part 290 may also be limited. The minimized distance and the limited movement of the local part 290 may further improve the MR imaging performance of the local coil apparatus 200 and/or the medical device 110. For example, the SNR of the MR image of the local part 290 may be improved.

In some embodiments, the second configuration of the receiving member assembly may be a fixed configuration that cannot be self-adaptively adjusted. When the receiving member assembly is in the second configuration, the configurations of the one or more receiving member 230 thereof may be predetermined.

In some embodiments, the second configuration of the receiving member assembly may be self-adaptively adjustable accoding to the size and/or shape of the local part 290. For example, each receiving member 230 of the receiving member assembly may have an initial configuration correspond to the first configuration of the receiving member assembly, and a final configuration corresponding to the maximum allowable configuration change of the receiving member 230. For example, in the initial configuration, the receiving member 230 may be closer to the housing 210, and in the final configuration, the receiving member 230 may be closer to the local part 290 or the central part of the receiving chamber formed by the housing 210. When the receiving member assembly reaches the second configuration, each receiving member 230 thereof may be in an intermediate configuration between the initial configuration and the final configuration. Such an intermediate configuration may be referred to as a stop configuration. The stop configuration may depend on various factors, such as the strength of the driving force, the distance between a corresponding portion of the local part 290 and the receiving member 230, the size and/or shape of the local part 290, or the like, or a combination thereof.

In some embodiments, the stop configuration may depend on the driving force from the driving mechanism 250. For example, a larger driving force may cause a higher degree of configuration change, and the stop configuration may be more toward the final configuration change. In some specific embodiments, the receiving member 230 may include an elastic component, which may exert a feedback force to the driving mechanism 250 due to the configuration change of the receiving member 230. The feedback force may be increased with the extent of the configuration change. When the feedback force reaches an equilibrium with the driving force, the configuration change of the receiving member 230 may be stopped, and the current configuration may be the stop configuration. For example, a smaller size of the local part 290 may generally have a smaller weight. For a local part 290 having a smaller weight, the activation member 240 may cause the driving mechanism 250 to generate a larger driving force, and the stop configuration may be more toward the final configuration.

In some embodiments, the second configuration may depend on the distance between the local part 290 and the receiving member 230. For example, the receiving member 230 may include a second sensor for sensing the distance between the local part 290 and the second sensor. When the distance is below a predetermined threshold, the second sensor or a processor in communication with the second sensor may transmit a control signal to the driving mechanism 250 to deactivate the driving mechanism 250. For example, the driving mechanism 250 may include an electric motor for generating the driving force, and the control signal may turn off the electric motor. When the driving mechanism 250 is deactivated, the configuration change of the receiving member 230 may be stopped, and the current configuration may be the stop configuration of the receiving member 230.

In some embodiments, the stop configuration of the receiving member 230 may depend on the size and/or shape of the local part 290. For example, during the configuration change, if the elastic deformation of the local part 290 is neglected, when the receiving member 230 presses the local part 290 and the local part 290 stopes the configuration of the receiving member 230 from changing further, the current configuration may be the stop configuration. As another example, during the configuration change, when the receiving member 230 is pressed against the local part 290 by the driving mechanism 250, the local part 290 may exert a feedback force to the receiving member 230. When the feedback force reaches an equilibrium with the driving force, the configuration change of the receiving member 230 may be stopped, and the current configuration may be the stop configuration of the receiving member 230.

In some embodiments, during the configuration change of the receiving member 230, the receiving member 230 may be moved/rotated toward the local part 290. During the moving/rotating of the receiving member 230, or when the receiving member 230 reaches the local part 290, the receiving member 230 may further be bent toward the local part 290 to cover a larger portion of the local part 290, so that the conformity toward the local part 290 may be improved.

The one or more receiving members 230 of the receiving system may be set according to the actual needs. In some embodiments, a receiving system may include a single receiving member 230. During the configuration change of the receiving member 230, the receiving member 230 may be bent to wrap the local part 290. In some specific embodiments, the receiving member 230 may further include a mechanical structure to guide its bending. Alternatively, the receiving system may include multiple receiving members 230, which may correspond to different portions of the local part 290. When the receiving member assembly is in the second configuration, each receiving member 230 thereof may be caused to conform to the corresponding portion of the local part 290. The multiple receiving members 230 may have the same or different shapes, sizes, and/or structures. In some embodiments, the multiple receiving members 230 may be symmetrically arranged.

In some embodiments, at least one receiving member 230 of the receiving system may include a flexible component which may be in contact with the local part 290 when the at least one receiving member 230 is in the second configuration. For example, the flexible component may be disposed on the surface of the receiving member 230 to be in contact with the local part 290. As another example, the flexible component may cover the whole surface of the receiving member 230. As a further example, the whole receiving member 230 may be the flexible component.

The flexible component may include at least one soft/elastic/flexible material, such as cotton, wool, cloth, leather, artificial fiber, sponge, rubber, silica gel, polyurethane, ethylene vinyl acetate (EVA) copolymer, latex, or the like, or a combination thereof. When the receiving member 230 is in the second configuration, the flexible component may undergo an elastic deformation and be caused to press against at least a portion of the local part 290, thereby reducing the pressure of the receiving member 230. When the subject 115 is a patient, the flexible component may make the patient feel more comfortable, and may avoid possible damage to the patient. In some specific embodiments, the first coil assembly 231 of the receiving member 230 may be inside the flexible component. Due to the elastic deformation of the flexible component, the first coil assembly 231 may be closer to the local part 290, and the imaging performance of the local coil apparatus 200 may be further improved.

In some embodiments, the housing 210 may include a bottom component 216 (first component) and a top component 215 (second component). The "bottom" and the "top" are with respect to the Y direction. During the MR scanning, the bottom component 216 may be configured to be positioned on the table 112, and the top component 215 may be installed on the bottom component 216. The top component 215 and the bottom component 216 can be detachably mounted together to form the whole housing 210 when the housing 210 is in a closed state, or be separated apart when the housing 210 is in an open state. In some embodiments, the at least one receiving system of the local coil apparatus 200 may be mounted on the bottom component 216. However, it is also possible that one or more of the above components may be mounted on the top component 215. When the housing 210 is in the open state, the local part 290 can be received by the bottom component 216. During the receiving, for each of the at least one receiving system, a corresponding portion of the local part 290 may be placed over the activation member 240 of the receiving system. Before the receiving, each of the one or more receiving member 230 of the receiving system may be in the first configuration to enable the local part 290 to be placed on the activation member 240. After the local part 290 is placed on the activation member 240, each of the one or more receiving member 230 may be changed into the second configuration, so that the first coil assembly (or assemblies) 231 of the local coil apparatus 200 may approach the local part 290. Then the top component 215 may be mounted on the bottom component 216 so that the housing 210 is in the closed state and be ready for MR imaging.

It is noted that besides the top-bottom form illustrated in FIG. 2A, the housing 210 may have any proper form for receiving the local part 290, which is not limited in the present disclosure.

In some embodiments, the top component 215 and the bottom component 216 may each include a part of the second coil assembly 225. Alternatively, either the top component 215 or the bottom component 216 may include the whole second coil assembly 225 (if any).

In some embodiments, the local coil apparatus 200 may further include a third coil assembly (not shown). The shape/position/structure of the third coil assembly may be changeable with respect to the housing 210, and the third coil assembly may be disposed on a component of the local coil apparatus 200 other than the one or more receiving members 230. For example, the top component 215 may include a movable section, which is movable/bendable/rotatable with respect to the top component 215. The movable section may include the above third coil assembly, and may be moved/bent/rotated to conform to a portion of the local part 290. For example, when the local part 290 includes the head of a patient, the movable section may be moved/bent/rotated to conform to the upfront face (or a part thereof) of the patient. The movable section is independent of the receiving system described above, and may be manually operated.

In some embodiments, in response to an activation of a corresponding activation member similar to the activation member 240, the top component 215 may be driven by a driving system similar to the driving mechanism 250, so as to be mounted on the bottom component 216. For example, when the local part 290 is properly placed on the activation member(s) 240 of the receiving member(s) 230 to trigger the activation member(s) 240, the local part 290 may trigger the activation member of the top component 215 as well. As a result, each of the receiving member(s) 230 may change the configuration to conform to the local part 290. In the meantime or with a short delay, the top component 215 may also be driven to cover the bottom component 216. During such a process, the top component 215 may also have a configuration change (e.g., be moved, rotated, and/or bent). In such embodiments, the top component 215 may also be viewed as a specifically configured receiving member 230. In some specific embodiments, the top component 215 may be formed by multiple parts, each of which may be viewed as a specifically configured receiving member 230. The configuration changes of the multiple parts may be performed simultaneously or sequentially. After the configuration changes, the multiple parts may together form the top component 215.

In some embodiments, the local coil apparatus 200 may further include other functioning members. For example, the local coil apparatus 200 may include a built-in power unit or a power input port to receive external power supply from, e.g., the medical device 110 or the data processing device 130. As another example, the local coil apparatus 200 may include an analog-to-digital converter to convert the received MR signals into digital data. As a further example, the local coil apparatus 200 may include an output port to output the received MR signals or digital data converted from the received MR signals to, e.g., the medical device 110 or the data processing device 130.

In some specific embodiments, the subject 115 may be a patient, and the local part 290 may include the head and the neck (or a portion thereof) of the patient. The local coil apparatus 200 may include a first receiving system and a second receiving system for receiving the head and the neck of the patient respectively according to the difference between the sizes/shapes of the head and the neck of the patient. Each of the first receiving system and the second receiving system may include an activation member 240, a driving mechanism 250, and a pair of receiving members 230 symmetrically arranged at both lateral sides of the local coil apparatus. Such embodiments are illustrated in FIGS. 5 to 10 and the descriptions thereof. It is noted that the local coil apparatus 200 may also include only one receiving system, or include more than two receiving systems.

In some embodiments, the activation members 240 of the first receiving system and the second receiving system may be integrated into an integral structure. For example, the local coil apparatus 200 may include a single activation member 240 for both the first receiving system and the second receiving system. When the local part 290 is placed on such an activation member 240, the driving mechanisms 250 of both the first receiving system and the second receiving system may be activated to cause the receiving members 230 of both the first receiving system and the second receiving system to conform to the local part 290.

Figure 3:
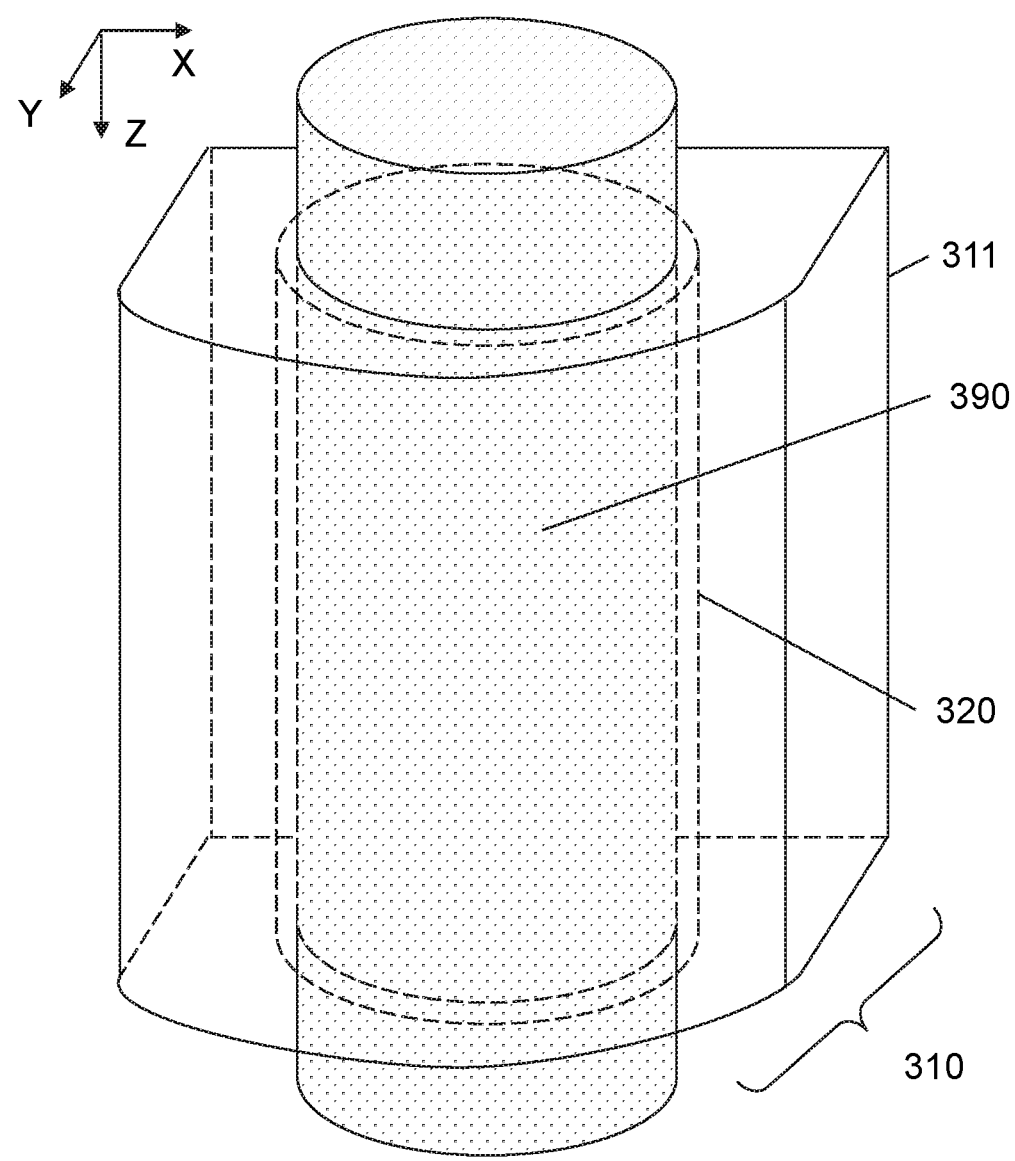
FIG. 3 is a schematic diagram illustrating an exemplary local coil apparatus according to some embodiments of the present disclosure.

In some embodiments, the local coil apparatus 200 may have the form as shown in FIG. 3. FIG. 3 is a schematic diagram illustrating an exemplary local coil apparatus 300 according to some embodiments of the present disclosure. The local coil apparatus 300 may be an example of the local coil apparatus 200. The local coil apparatus 300 illustrated in FIG. 3 is in the closed state.

The local coil apparatus 300 may include a housing 310 for receiving a local part 390 of a subject 115, and may include a coil assembly 320 for performing the MR imaging on the local part 390. The local coil apparatus 300 may also include an aforementioned receiving member assembly. The receving member assembly may include one or more receiving members corresponding to the receiving member 230, which are not illustrated in FIG. 3. When the receiving member assembly of the local coil apparatus 300 is in the second configuration, the first coil assemblies of the one or more receiving members may together form at least a portion of the coil assembly 320. The housing 310 may be an example of the housing 210. The housing 310 may include a substantially flat surface 311 corresponding to the surface 211. The housing 310 may include at least two openings. The subject 115 may penetrate the housing 310 through the at least two openings, leaving the local part 390 (e.g., a knee) inside the housing 310. In some embodiments, the local coil apparatus 300 may include fixed coils that are embodiments of the second coil assembly 225. The fixed coils may be a part of the coil assembly 320. In some embodiments, the local coil apparatus 300 may not include coils that are embodiments of the second coil assembly 225. Then the coil assembly 320 may be formed only by the first coil assembly (or assemblies) of the one or more receiving members.

Figure 4:
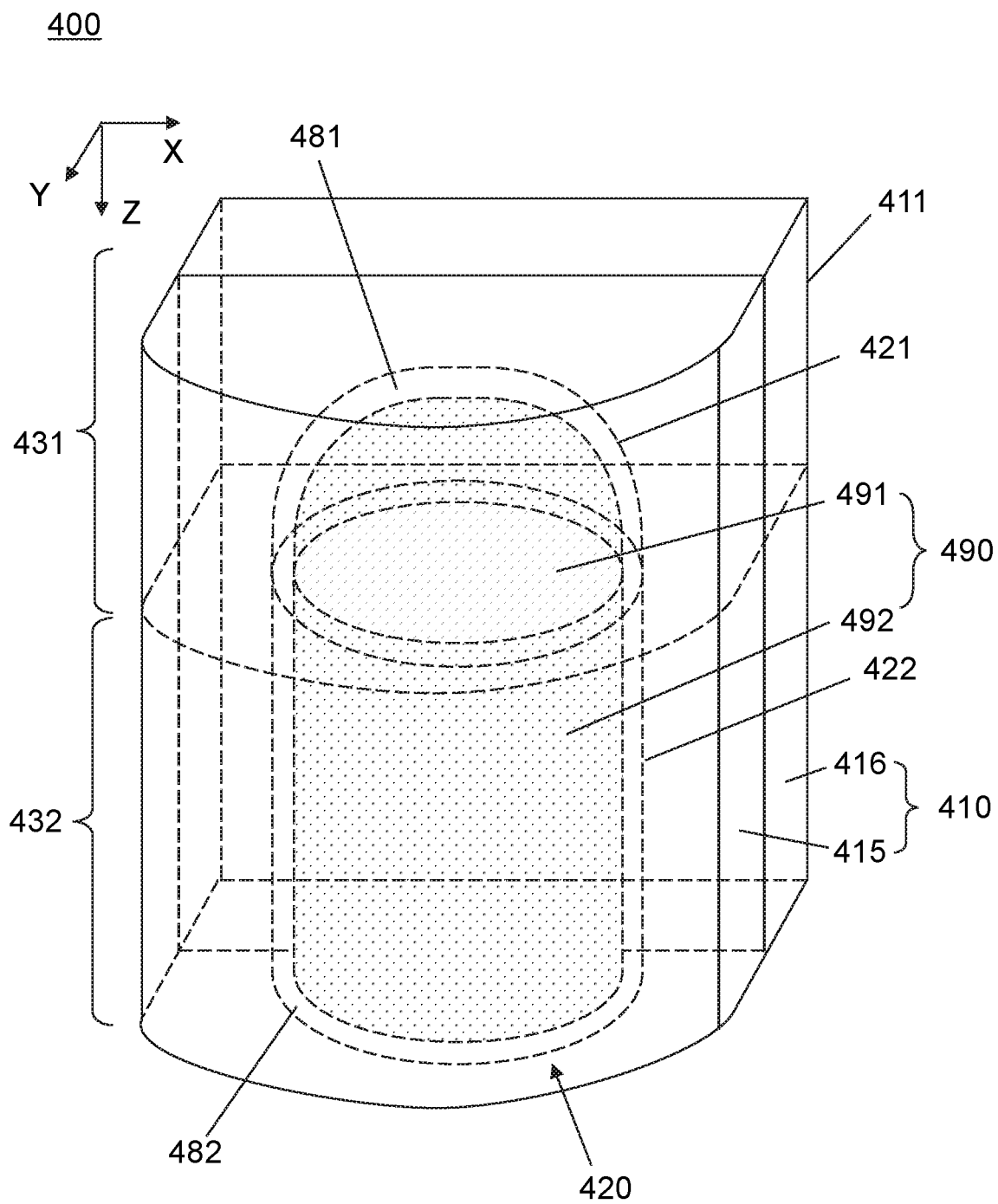
FIG. 4 is a schematic diagram illustrating an exemplary local coil apparatus according to some embodiments of the present disclosure.

In some embodiments, the local coil apparatus 200 may have the form as shown in FIG. 4. FIG. 4 is a schematic diagram illustrating an exemplary local coil apparatus 400 according to some embodiments of the present disclosure. The local coil apparatus 400 may be an example of the local coil apparatus 200. The local coil apparatus 400 illustrated in FIG. 4 is in the closed state.

The local coil apparatus 400 may include a housing 410 for receiving a local part 490 of a subject 115, and may include a coil assembly 420 for performing the MR imaging on the local part 490. The coil assembly 420 may include an upper coil sub-assembly 421 and a lower coil sub-assembly 422 for performing the MR imaging on different portions of the local part 490 (with respect to the Z direction). The local coil apparatus 400 may also include a receiving member assembly. The receiving member assembly may include one or more receiving members corresponding to the receiving member 230, which are not illustrated in FIG. 4. When the receiving member assembly is in the second configuraion, the first coil assembly (or assemblies) thereof may together form at least a part of the lower coil sub-assembly 422. The local coil apparatus 400 may include fixed coils that are embodiments of the second coil assembly 225. The upper coil sub-assembly 421 may be formed solely by the fixed coils. In some embodiments, the lower coil sub-assembly 422 may also include a part formed by the fixed coils.

The housing 410 may be an example of the housing 210. The housing 410 may include a substantially flat surface 411 corresponding to the surface 211. The housing 410 may include a single opening for receiving the local part 390, but may include openings for other use in some embodiments. The local part 390 may be an end (e.g., the head) of the subject 115, which may not penetrate through the housing 410. The local part 490 may include a first portion 491 and a second portion 492. The upper coil sub-assembly 421 may be for scanning the first portion 491, and the lower coil sub-assembly 422 may be for scanning the second portion 492. In some embodiments, the housing 410 may include a top component 415 and a bottom component 416, which may correspond to the top component 215 and the bottom component 216 respectively.

In some embodiments, the local part 490 may be the head of a patient, and the local coil apparatus 400 may also be referred to as a head coil or a head coil apparatus. When the installation of the local coil apparatus 400 on the head of the patient is completed, the local coil apparatus 400 may accommodate the head of the patient and optionally a part of the neck of the patient. Under such a situation, a first scanning region 481 and a second scanning region 482 may be formed inside the inner space of the local coil apparatus 400. The first scanning region 481 may be for scanning, by the upper coil sub-assembly 421, the top (or be referred to as an upper part) of the head, and the second scanning region 482 may be for scanning, by the lower coil sub-assembly 422, the other part (or be referred to as a lower part) of the head. The upper coil sub-assembly 421 may conform to the upper part of the head, and may receive the MR signals of the upper part of the head. For example, the upper coil sub-assembly 421 may be around the upper part of the head and may form a dome-like structure. The lower coil sub-assembly 422 may conform to the lower part of the head, and may receive the MR signals of the lower part of the head. For example, the lower coil sub-assembly 422 may be around the lower part of the head and may form a barrel-like structure. In some embodiments, the lower coil sub-assembly 422 may further emit RF signals for exciting the scanning part. The RF signals emitted by the lower coil sub-assembly 422 may form a local RF field. The angle between the direction of the local RF field and the direction (e.g., along the Z direction) of the main magnetic field generated by the magnet assembly of the medical device 110 may be adjusted by adjusting the position of the first coil assembly (or assemblies) of the local coil apparatus 400.

In some embodiments, the lower coil sub-assembly 422 may include a posterior part and an anterior part (with respect to the Y direction). The anterior part of the lower coil sub-assembly 422 may correspond to the top component 415 of the housing 410, and may be configured to receive the MR signals of the anterior portion of the head of the subject 115. The posterior part of the lower coil sub-assembly 422 may corresponding to the bottom component 416 of the housing 410, and may be configured to receive the MR signals of the neck, cheek, and/or posterior portion of the head of the subject. The top component 415 and the bottom component 416 may together hold the head and neck of the subject 115.

According to the positions of the upper coil sub-assembly 421 and the lower coil sub-assembly 422, the inner space provided by the housing 410 may include an upper space 431 and a lower space 432. In some embodiments, the one or more receiving members of the local coil apparatus 400 may be disposed inside the lower space 432. In the case of the local coil apparatus 300 illustrated in FIG. 3, the one or more receiving members may be disposed throughout the inner space provided by the housing 310.

In some embodiments, the local coil apparatus 300/400 may include a first receiving system and a second receiving system. The first receiving system may include at least one first receiving member, and the second receiving system may include at least one second receiving member. The at least one first receiving member may each include a first flexible component, and the at least one second receiving member may each include a second flexible component. The first flexible component(s) and/or the second flexible component(s) of the local coil apparatus 300/400 may each include a first coil assembly.

In some embodiments, the at least one first receiving member may include a pair of first receiving members, and the at least one second receiving member may include a pair of second receiving members. The pair of first/second receiving members may be mounted on the two lateral sides of the inner surface of the housing 310/490 respectively. When the pair of first/second receiving members are in their second configurations, the first/second flexible components thereof may be in contact with and may together hold a corresponding portion of the local part 390/490. For example, in the case of the local coil apparatus 400, the local part 490 may include the head of a patient and at least a portion of the neck of the patient, the first flexible components may together hold the neck of the patient, and the second flexible components thereof may together hold the head of the patient (or a portion thereof).

Each of the first receiving system and the second receiving system may include a driving mechanism (corresponding to the driving mechanism 250) and an activation member (corresponding to the activation member 240) for driving the configuration change of each of the pair of first receiving members and the pair of second receiving members. In some embodiments, the activation members of the first receiving system and the second receiving system may be integrated into a single component.

In some embodiments, only one first receiving member and only one second receiving member may be mounted on the inner surface of the housing 310/410. When the receiving member assembly is in the second configuration, the first/second flexible component thereof may contact a corresponding portion of the head of a patient. In some embodiments, during the configuration change, the first/second flexible component may be transformed or bent to wrap a corresponding portion of the head.

It is understood that other proper configurations of the receiving member(s) are also possible. For example, the local coil apparatus 300/400 may include only one first driving mechanism and a pair of second receiving members, or include only one second driving mechanism and a pair of first driving mechanisms. As another example, besides the first receiving member(s) and the second receiving member(s), the local coil apparatus 400 may further include other receiving member(s) to hold another portion of the local part 290.

In the following of the present disclosure, an exemplary head coil apparatus is described in detail, which may be an embodiment of the local coil apparatus 200/400. It is understood that the head coil apparatus are provided only for demonstration purposes and not intended to be limiting. The configuration of the head coil apparatus, especially the configurations of the receiving member(s), the activation member(s), and the driving mechanism(s), may be used in local coil apparatus of other types of local part, such as a knee, the abdomen, a hand, or a foot of a patient. The provided configurations may also be used in apparatus specially designed to perform an MR imaging on another type of subject, such as animals, antiques, plants, etc. The provided configurations may also be used in other application fields. For example, the first coil assembly and the second coil assembly (if any) may be removed from the apparatus, and the one or more receiving members of the apparatus may be configured to clamp a local part of an object to be fixed. The apparatus may be used as a mounting or fixing structure in medical imaging fields as well as other application fields.

Figure 5:
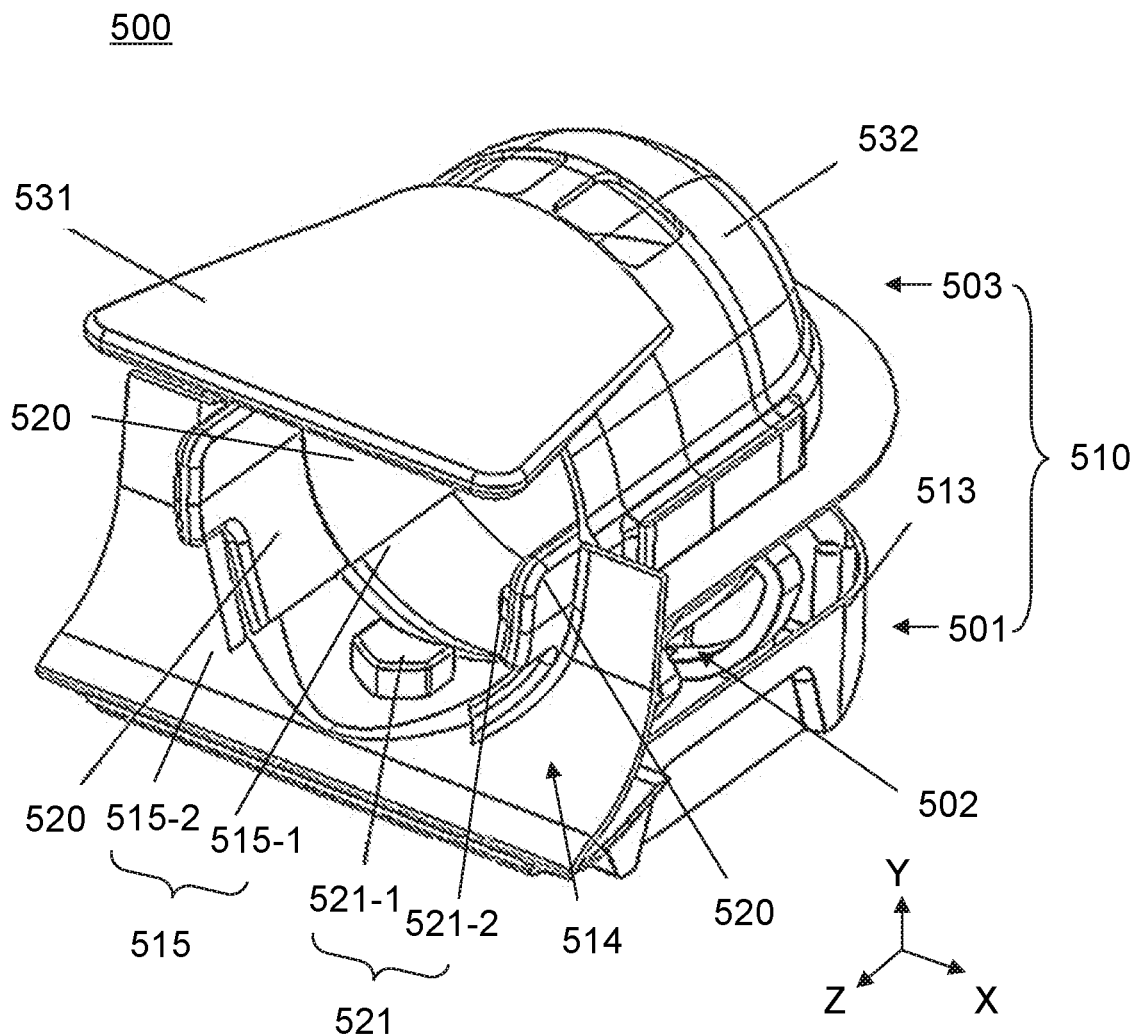
FIGS. 5 to 7 are schematic diagrams illustrating an exemplary head coil apparatus according to some embodiments of the present disclosure.
Figure 6:
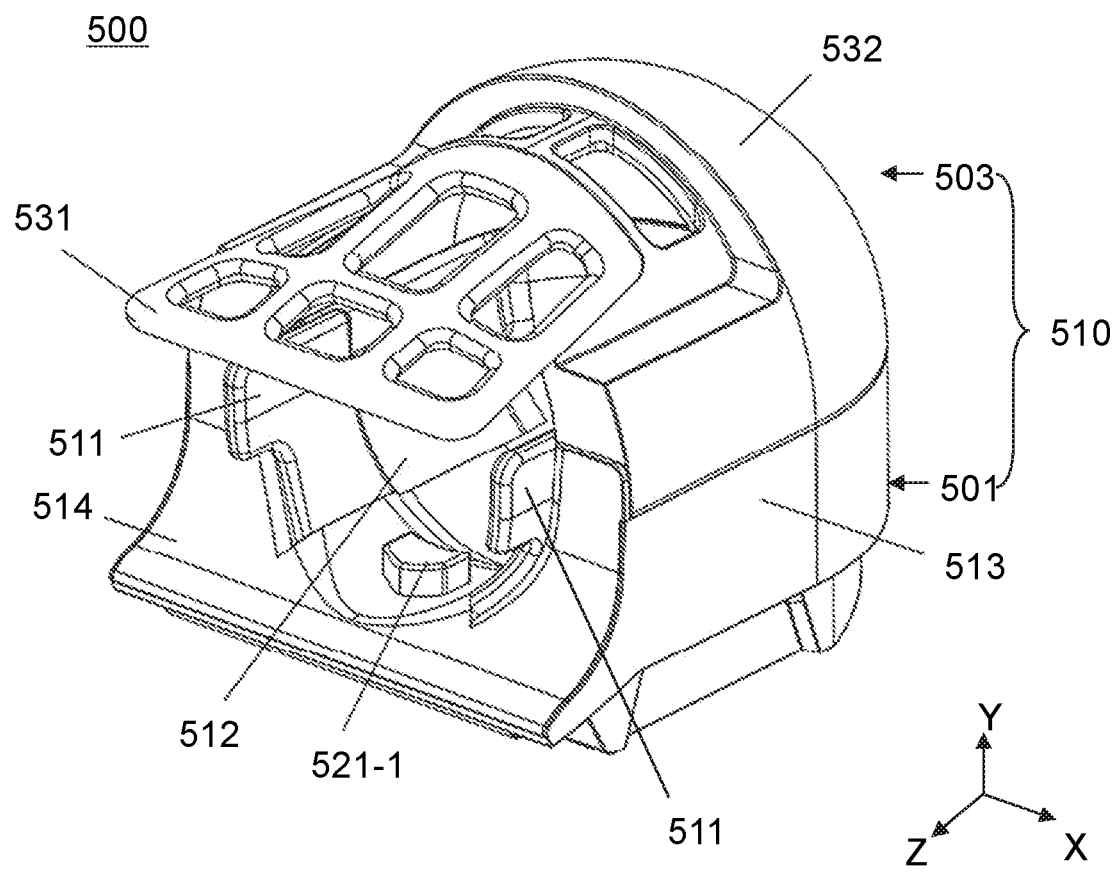
Figure 7:
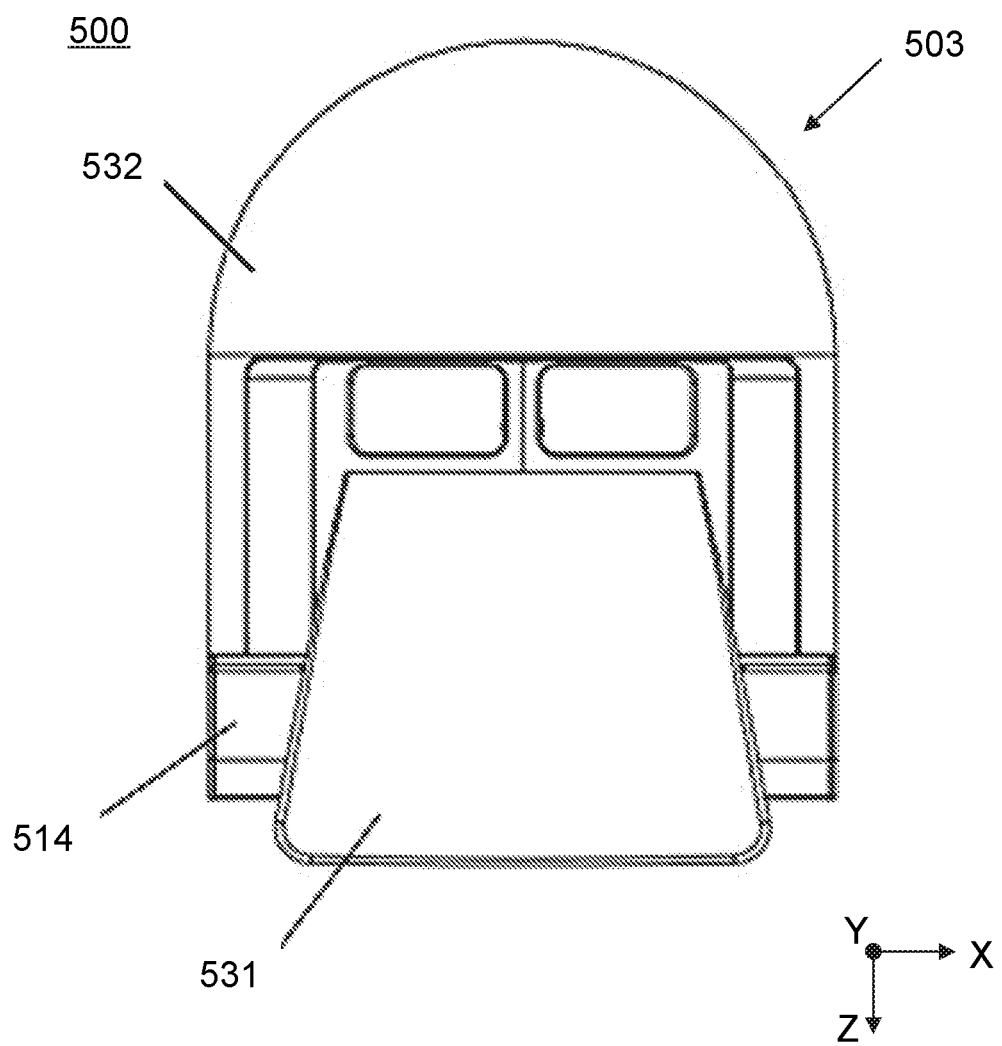

FIGS. 5 to 7 are schematic diagrams illustrating an exemplary head coil apparatus 500 according to some embodiments of the present disclosure. FIG. 5 illustrates a first view of the head coil apparatus 500 illustrated. FIG. 6 illustrates a second view of the head coil apparatus 500. FIG. 7 illustrates a third view of the head coil apparatus 500. The head coil apparatus 500 may be an example of the local coil apparatus 200 (or 400). As shown in FIGS. 5 to 7, the head coil apparatus 500 may include a housing 510 and a one or more receiving systems. Each of the one or more receiving systems may include a receiving member assembly, a driving mechanism 502, and an activation member 521. The receiving member assembly may include a plurality of receiving members 520. In some embodiments, the receiving member assembly may further include one or more other functioning members (e.g., as described in connection with FIG. 2A). The housing 510 may be an example of the housing 210 (or 410). Each of the plurality of receiving members 520 may be an example of the receiving member 230. The driving mechanism 502 may be an example of the driving mechanism 250. The housing 510 may include a top component 503 and a bottom component 501. The top component 503 and the bottom component 501 may be examples of the top component 215 and the bottom component 216, respectively. The top component 503 and the bottom component 501 may be connected together to form an arc-shaped receiving chamber providing an inner space. The plurality of receiving members 520 and the driving mechanism 502 may be inside the receiving chamber. The configurations of the top component 503 and the bottom component 501 may enable the head of the user to enter into the receiving chamber and take an MR imaging. The plurality of receiving members 520 may be connected to the inner surface of the receiving chamber, and can be rotated around the connecting point.

Figure 8:
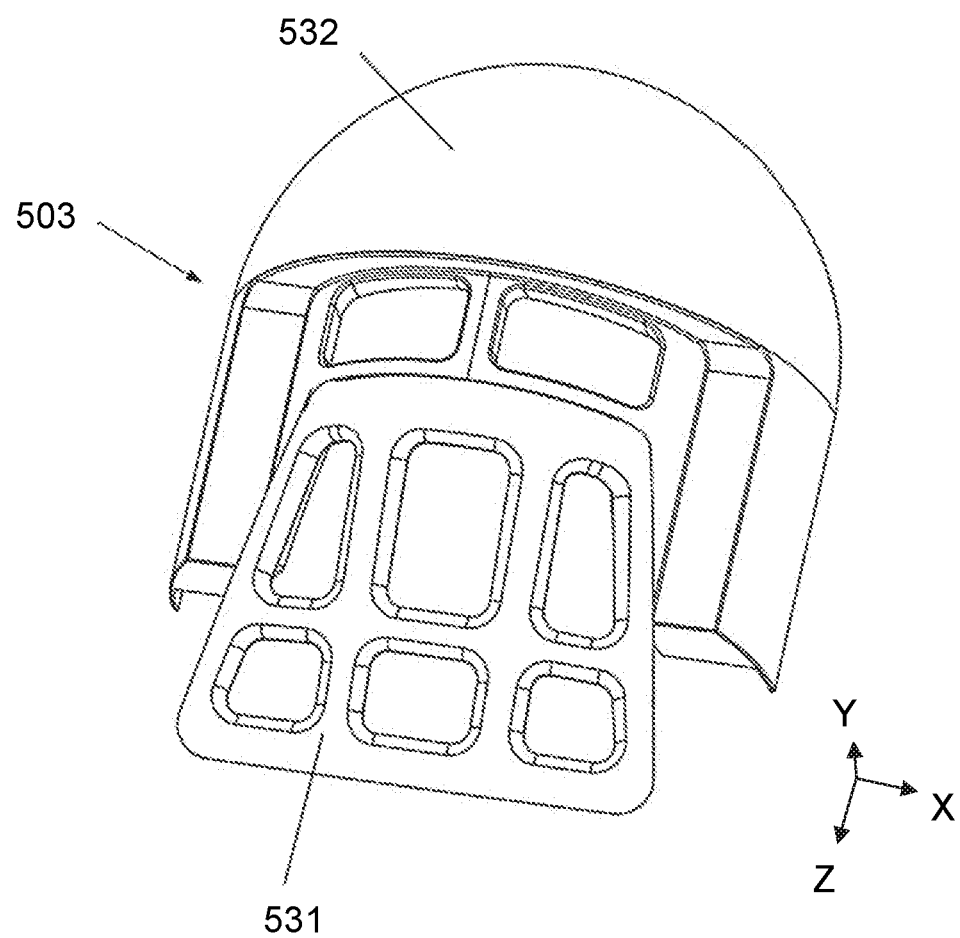
FIG. 8 is a schematic diagram illustrating a top component of the head coil apparatus illustrated in FIGS. 5 to 7 according to some embodiments of the present disclosure.
Figure 9:
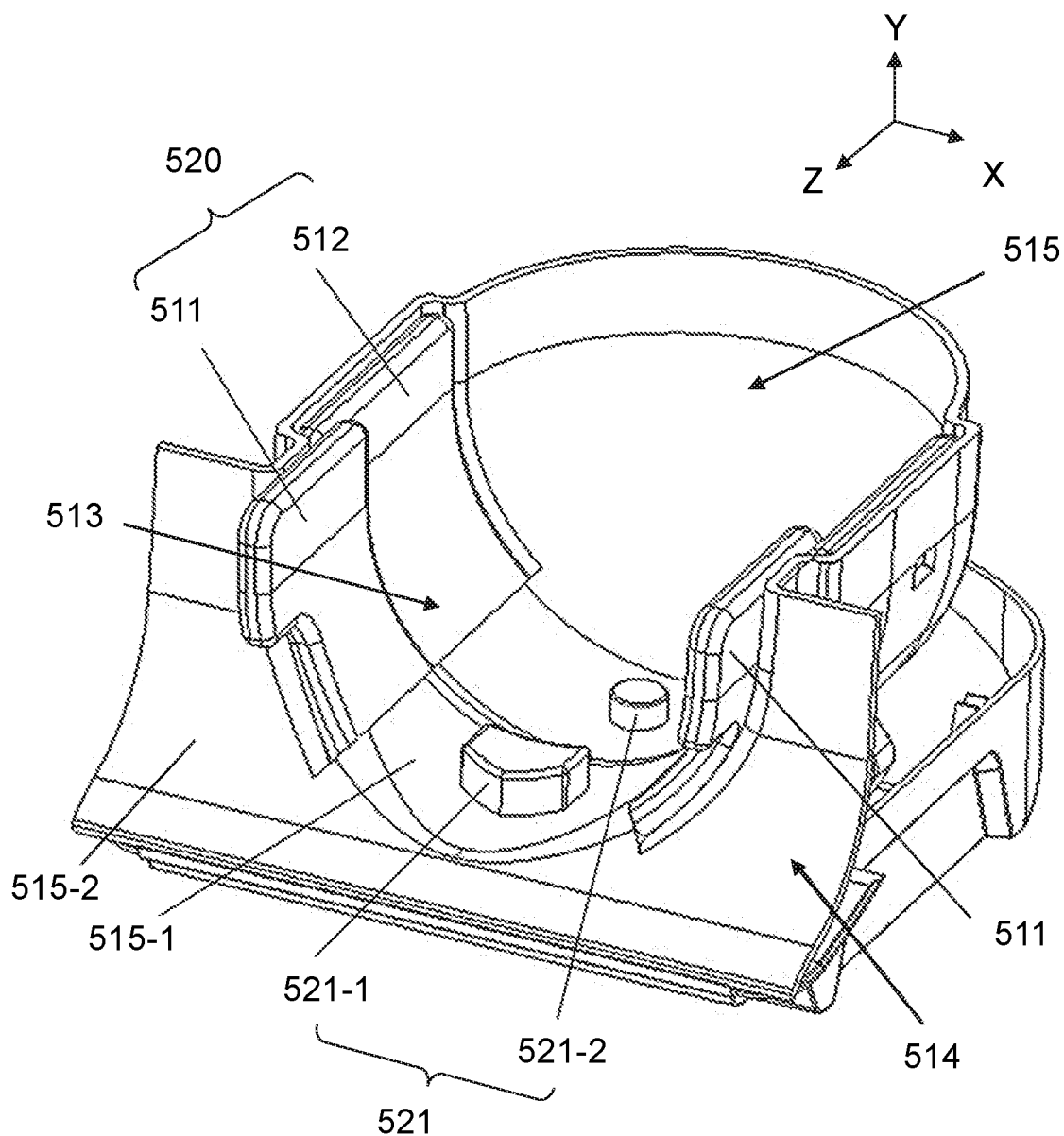
FIGS. 9 and 10 are schematic diagrams illustrating a bottom component of the head coil apparatus illustrated in FIGS. 5 to 7 according to some embodiments of the present disclosure.
Figure 10:
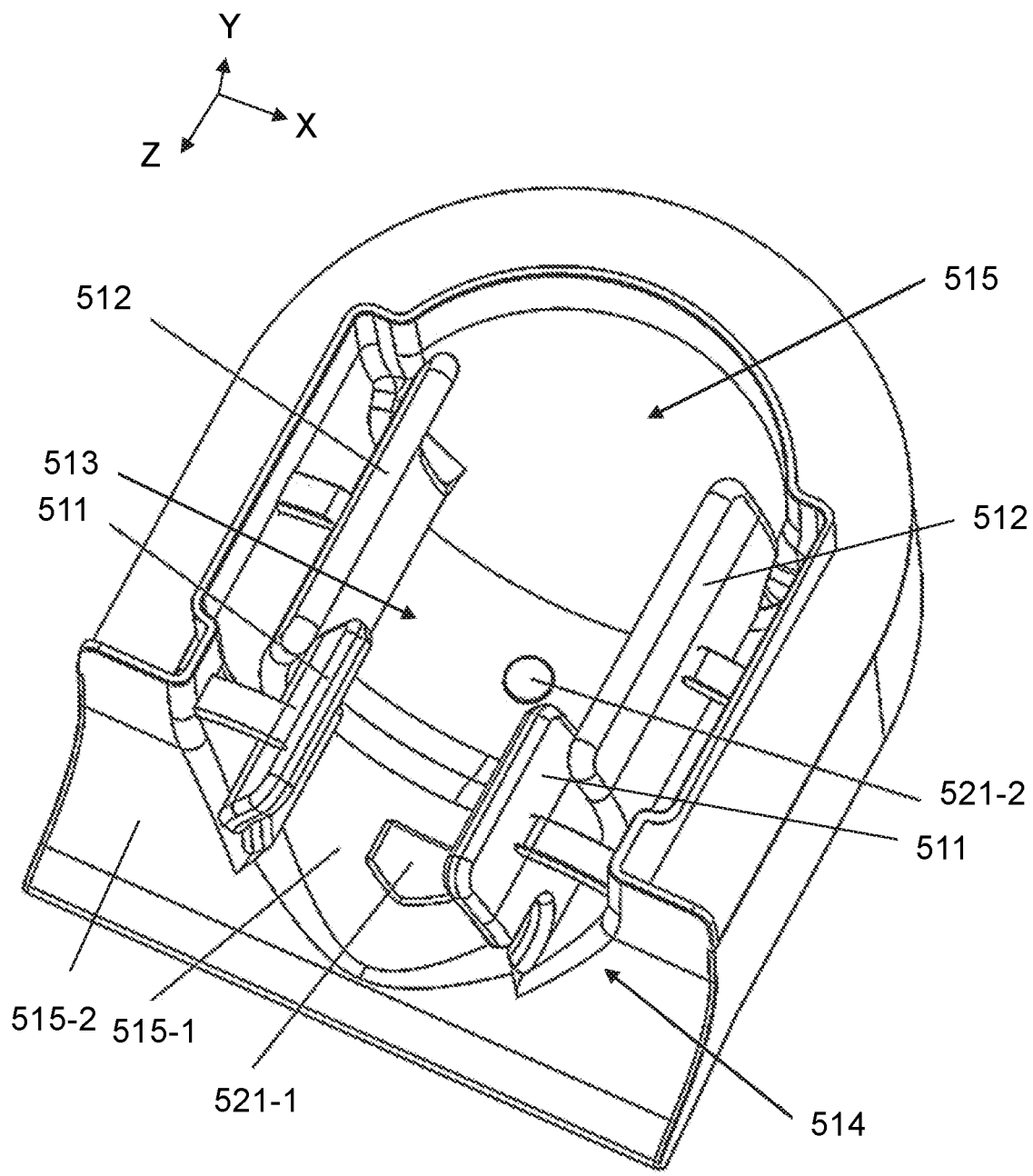

FIG. 8 is a schematic diagram illustrating the top component 503 of the head coil apparatus 500 illustrated in FIGS. 5 to 7 according to some embodiments of the present disclosure. FIGS. 9 and 10 are schematic diagrams illustrating the bottom component 501 of the head coil apparatus 500 illustrated in FIGS. 5 to 7 according to some embodiments of the present disclosure. In FIG. 9, the bottom component 501 may be in a natural state (or idle state). In the natural state, the plurality of receiving members 520 may be in their first configurations. In FIG. 10, the bottom component may be in a working state (or scanning state). In the working state, the head of the patient may be placed on the at least one activation member 521, and the receiving member assembly may be in the second configuration.

As shown in FIG. 8, the top component 503 may include a movable scan section 531 and a first fixed scan section 532. As shown in FIGS. 8 and 9, the bottom component 501 may include a second fixed scan section 513, a third fixed scan section 514, and supporting shells 515. The supporting shells 515 may include a first supporting shell 515-1 and a second supporting shell 515-2, which may be disposed on the outer surfaces of the second fixed scan section 513 and the third fixed scan section 514 respectively.

It is noted that the shell of the top component 503 is not shown in FIG. 5, but shown in FIGS. 6, 7, and 8; the upper shell (with respect to the Y direction) of the movable scan section 531 is shown in FIGS. 5 and 7, but not shown in FIGS. 6 and 8; a part of the shell of the bottom component 501 is not shown in FIGS. 5 and 9, but shown in FIGS. 6 and 10.

The driving mechanism 502 may be connected to the plurality of receiving members 520. The plurality of receiving members 520 may be arranged symmetrically on both lateral sides of the head coil apparatus 500. In some embodiments, the driving mechanism 502 may change the configuration of the plurality of receiving members 520, so that the configuration of the receiving member assembly may be changed from the first configurations to the second configuration. By changing the configurations of the plurality of receiving members 520, the distance between each of the plurality of receiving members 520 and a corresponding portion of the subject to be scanned may be adjusted, and the plurality of receiving members 520 may conform to the corresponding portions. In some embodiments, during the configuration change, the plurality of receiving members 520 may be bent.

The supporting shells 515, the first fixed scan section 532, and the second fixed scan section 513 may form the aforementioned receiving chamber (e.g., as shown in FIGS. 5 and 6), and the plurality of receiving members 520 may be installed in the receiving chamber. For example, the plurality of receiving members 520 may be installed on the supporting shell 515-1. The movable scan section 531 may be disposed outside the receiving chamber. In some embodiments, the movable scan section 531 and the first fixed scan section 532 may be disposed above the driving mechanism 502, and the third fixed scan section 514 may be disposed outside the receiving chamber. In some embodiments, the second fixed scan section 513 and the third fixed scan section 514 may be respectively disposed on the front side and rear side (e.g., with respect to the Z direction) of the receiving chamber, and the third fixed scan section 514 may be disposed below the movable scan section 531, and the first fixed scan section 532 may be disposed above the second fixed scan section.

The curved portions of the first fixed scan section 532 and the second fixed scan section 513 may together form an upper portion (with respect to the Z direction) of the head coil apparatus 500, and the other portion(s) of the head coil apparatus 500 may be referred to as a lower portion of the head coil apparatus 500 (with respect to the Z direction). The upper portion of the head coil apparatus 500 may receive MR signals from the top region of the head of the scanned subject. The lower portion of the head coil apparatus 500 may receive the MR signals from the other region of the head and the neck of the subject.

As the width of the head of a patient is generally larger than the width of the neck of the patient, in order to make the receiving members 520 of the head coil apparatus 500 to be more comfortable to the patient's head and neck, as shown in FIGS. 5 and 6, the one or more receiving systems may include a first receiving system and a second receiving system. The first receiving system may include a pair of first receiving members 511, a driving mechanism 502 associated with the pair of first receiving members 511, and a first activation member 521-1. The second receiving system may include a pair of second receiving members 512, a driving mechanism 502 associated with the pair of second receiving members 512, and a second activation member 521-2. The pair of first/second receiving members 511/512 may be arranged (e.g., symmetrically) on both lateral sides of the local coil apparatus 500, and may be configured to hold the neck/head of the patient specifically. In some embodiments, for each of the first receiving system and the second receiving system, the corresponding driving mechanism 502 may be disposed below (with respect to the Y direction) the corresponding pair of receiving members 520. The pair of first receiving members 511 and the pair of second receiving members 512 may be driven separately by the corresponding driving mechanism 502, so that the pair of first receiving members 511 and the pair of second receiving members 512 may be individually adjusted according to the widths of the neck and head of the patient respectively. As a result, the first coil assemblies of the pair of first receiving members 511 and the pair of second receiving members 512 may be closer to the neck and the head of the patient respectively, reducing the errors of the MR scanning.

In some embodiments, the pair of first/second receiving members 511/512 may be symmetrically disposed on both lateral sides of the head coil apparatus 500. The first activation member 521-1 and the second activation member 521-2 may be configured to activate the driving mechanism 502 associated with the pair of first receiving members 511 and the pair of second receiving members 512 respectively. The first activation member 521-1 and the second activation member 521-2 may have any proper size or shape. For demonstration purposes, in FIGS. 5, 6, 9, and 10, the first activation member 521-1 and the second activation member 521-2 are in different shapes/sizes. However, it is also possible that the first activation member 521-1 and the second activation member 521-2 have the same shape/size. In some specific embodiments, the first/second activation member 521-1/521-2 may have a shape/size adaptive to the neck/head of the patient to improve the comfortableness of the head coil apparatus 500.

In some embodiments, the first activation member 521-1 and the second activation member 521-2 may be an integral structure configured to activate both the driving mechanisms 502 of the first receiving system and the second receiving system.

During the configuration change caused by the corresponding driving mechanism 502s, the pair of first receiving members 511 and the pair of second receiving members 512 may be bent to conform to the patient's head or neck. The patient may feel comfortable during such a process, and the MR signals obtained by the head coil apparatus 500 may be remarkably enhanced. The first receiving members 511 and the second receiving members 512 may each include a flexible component which may be in contact with the head of the patient after the configuration change. The flexible components may include one or more soft/elastic/flexible materials to make the patient more comfortable during the examination. In some embodiments, the first coil assemblies of the receiving members may be embedded in the flexible components thereof to further reduce the distances between the first coil assemblies and the corresponding portions of the head.

In some embodiments, the first receiving member 511 and the second receiving member 512 on the same side of the head coil apparatus 500 may be arranged side by side along a first direction (e.g., the Z direction). When the head coil apparatus 500 is in the idle state, in a second direction (e.g., the X direction) that is perpendicular to the first direction, the distance between the pair of first receiving members 511 may be smaller than the distance between the pair of second receiving members 512. Such a configuration may reduce the error of the MR scan data caused by different sizes of different scanned portions.

In some embodiments, the head coil apparatus 500 may further include more receiving members. For example, the head coil apparatus 500 may further include a pair of third receiving members (now shown). The pair of second receiving members 512 and the pair of the third receiving members may together hold the head (or a part thereof) of the patient.

It is noted that the grid lines in the first fixed scan section 532 illustrated in FIG. 5 represent the layout of the second coil assembly (or assemblies) therein. In some embodiments, the above grid lines may be omitted.

Figure 11:
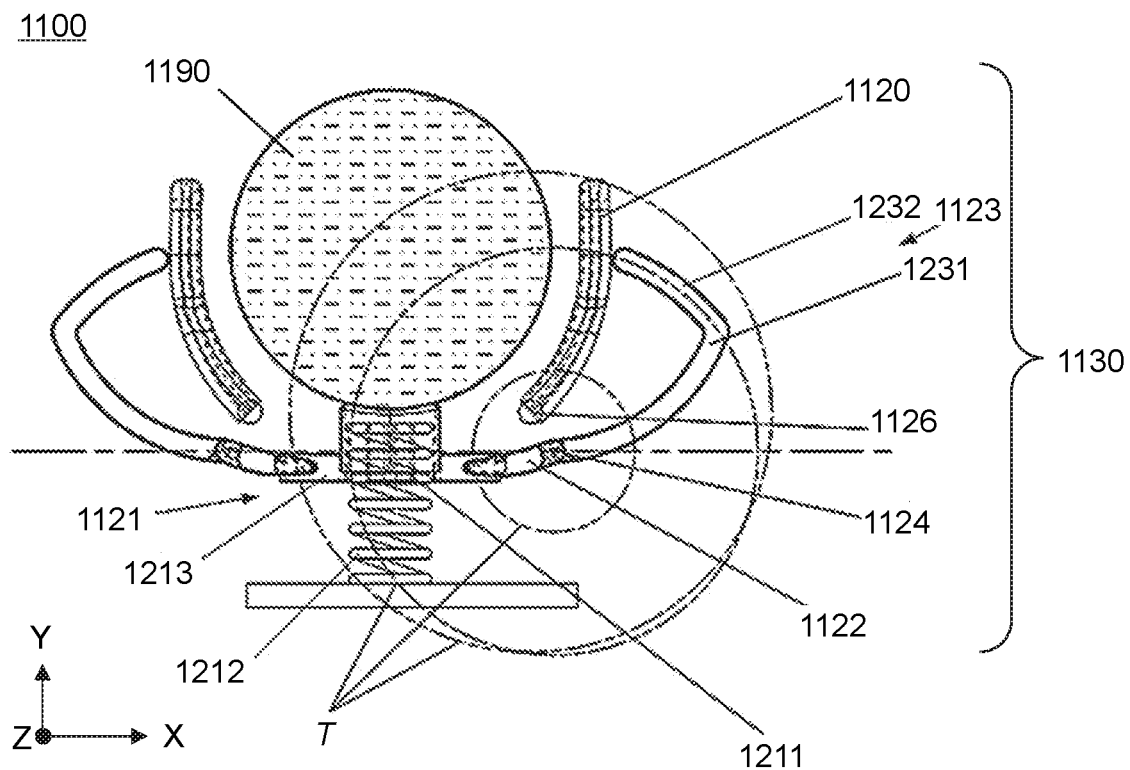
FIG. 11 is a schematic diagram illustrating an exemplary receiving system of a local coil apparatus in its idle state according to some embodiments of the present disclosure.
Figure 12:
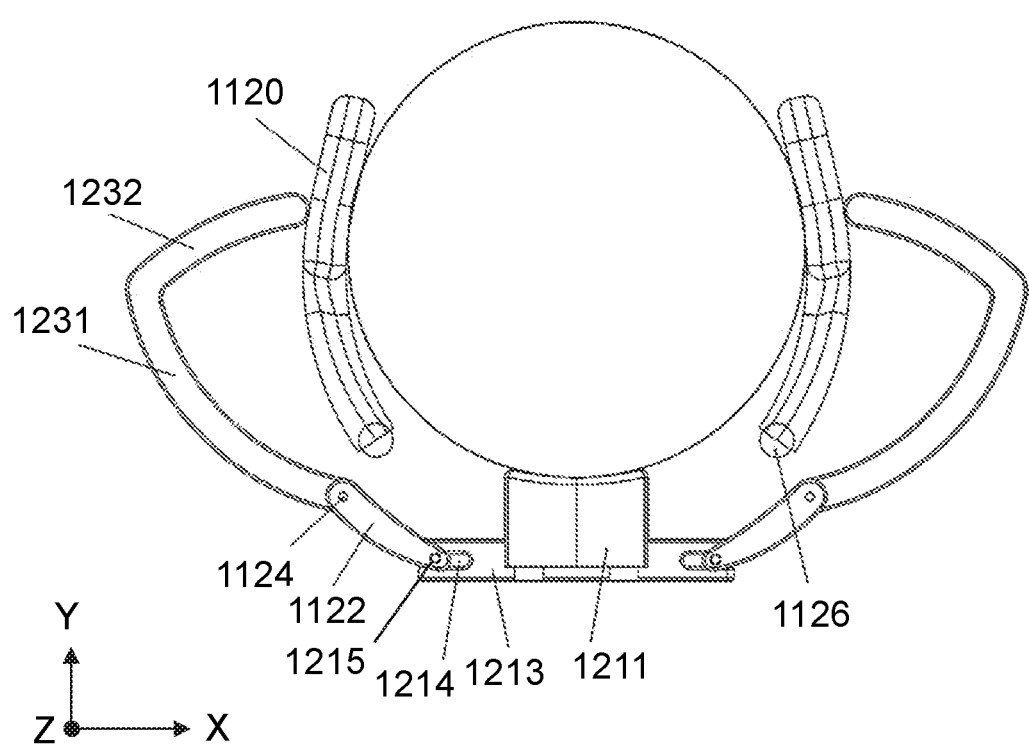
FIG. 12 is a schematic diagram illustrating the receiving system illustrated in FIG. 11 in its operating state according to some embodiments of the present disclosure.

FIG. 11 is a schematic diagram illustrating an exemplary receiving system 1100 of a local coil apparatus in its idle state according to some embodiments of the present disclosure. FIG. 12 is a schematic diagram illustrating the receiving system 1100 illustrated in FIG. 11 in its operating state according to some embodiments of the present disclosure. The receiving system 1100 may be an example of the receiving system of the local coil apparatus 200 or head coil apparatus 500. As shown in FIGS. 7 and 8, the receiving system 1100 may include a pressing member 1121, which may be an example of the activation member 521. The pressing member 1121 may be pressed down (with respect to the Y direction) by a local part 1190 (e.g., the head or neck of a patient). The receiving system 1100 may also include a pair of receiving members 1120, each of which may be an example of the receiving member 520/230. For example, the pair of receiving members 1120 may be the pair of first receiving members 511, the pair of second receiving members 512, or any other pair of receiving members of the head coil apparatus 500.

The receiving system 1100 may also include a driving mechanism 1130 connected to the pair of receiving members 1120 and the pressing member 1121. The driving mechanism 1130 may be an example of the driving mechanism 250/502. For each of the pair of receiving members 1120, the driving mechanism 1130 may include a first rod 1122 and a second rod 1123, which may be examples of the first rod 251 and the second rod 252 respectively. The pair of first rods 1122 and the pair of second rods 1123 may be symmetrically arranged on both sides of the local coil apparatus. For the convenience of description, the receiving system 1100 may be further described by taking the first rod 1122, the second rod 1123, and the receiving member 1120 on the same side as an example.

The pressing member 1121 may be connected to the first rod 1122 and can drive the first rod 1122 to move (e.g., rotate). The second rod 1123 may include a first end pivotally connected to the first rod 1122, and a second end connected to the receiving member 1120 to drive the receiving member 1120 to move, rotate, and/or bend toward the local part 1190. The second rod 1123 may be moved/rotated together with the first rod 1122. In some embodiments, the first rod 1122 and the second rod 1123 may be connected via an elastic component 1125. The elastic component 1125 may provide a torque between the first rod 1122 and the second rod 1123. The torque (i.e., the aforementioned strengthen forth) may cause the second rod 1123 to rotate along with the first rod 1122 when the receiving member 1120 is not in contact with (hasn't reached) the local part 1190, and may also cause the second rod 1123 to move (e.g., rotate) relative to the first rod 1122 when the receiving member 1120 reaches the local part 1190. In such a situation, the configuration change of the receiving member 1120 may be stopped by the local part 1190, but the pressing member 1121 may not be fully pressed down. When the pressing member 1121 is not fully pressed, the pressing member 1121 may keep output an activation force resulting from the force exerted by the local part 1190, causing the driving mechanism 1130 to drive the receiving member 1120 Then the elastic component 1125 may cause the second rod 1123 to move (e.g., rotate) relative to the first rod 1122 to enable the pressing member 1121 to be fully pressed down, which may make the patient to feel more comfortable and avoid potential health damage to the patient. In some embodiments, the first rod 1122 and the second rod 1123 may be connected via a first connecting shaft 1124. The elastic component 1125 may be disposed at the first connecting shaft 1124, and may be pressed to the first rod 1122 and the second rod 1123. In some specific embodiments, the first connecting shaft 1124 may locate on the surface of the supporting shell 515 that faces away from the local part to be scanned, and may be pivotally mounted on the supporting shell 515 as a fixed pivot point.

In some embodiments, the elastic component 1125 may be a torsion spring. To install the torsion spring on the receiving system 1100, the body of the torsion spring may be first disposed to surround the first connecting shaft 1124, and then the two ends of the first connecting shaft 1124 may be inserted into the first rod 1122 and the second rod 1123, respectively. Next, the two ends of the torsion spring may be pressed to the first rod 1122 and the second rod 1123 respectively, ensuring that the second rod 1123 can be rotated with respect to the second rod 1123 when the local part 1190 has a larger size, and can be returned back to its original position after the feedback force exerted by the local part 1190 disappears.

In some embodiments, one or more through-holes (not shown) may be arranged on the supporting shell 515, each of which may accommodate a corresponding pressing member 1121 passing through the supporting shell 515. In some embodiments, when multiple through-holes are arranged on the supporting shell 515, the multiple through-holes may be arranged according to the shape/size of the local part 1190.

For example, when the local part 1190 is the head of a patient, the multiple through-holes may be arranged in a line. The pressing member 1121 may include a first part above (with respect to the Y direction) the supporting shell 515, and a second part beneath (with respect to the Y direction) the supporting shell 515. The first rod 1122 and the second rod 1123 may be both beneath the supporting shell 515. When the pressing member 1121 is pressed down, the first rod 1122 may rotate with respect to the activation member, and the second rod 1123 may also rotate together with the first rod 1122. As the first connecting shaft 1124 is pivotally mounted on the supporting shell 515, and the first rod 1122 and the second rod 1123 are connected to the elastic component 1125 that is disposed over the first connecting shaft 1124, when the receiving member 1120 is in contact with the local part 1190, the elastic component 1125 may allow the pressing member 1121 to be pressed down to the bottom (or be referred to as being fully pressed down), so that the top surface (with respect to the Y direction) of the pressing member 1121 can be coplanar with the surface of the supporting shell 515 that faces the local part 1190 during the MR imaging, no matter the size/shape of the local part 1190. As a result, the patient may not be annoyed by the protrusion of the top surface of the pressing member 1121.

When the head/neck of the subject is placed on the pressing member 1121 causing the pressing member 1121 to be pressed down, the pressing member 1121 may drive the first rod 1122 to rotate about the first connecting shaft 1124. As the first rod 1122 and the second rod 1123 are connected via the first connecting shaft 1124, and the elastic component 1125 is disposed over the first connecting shaft 1124, when the first rod 1122 rotates about the first connecting shaft 1124, the resulting torsion of the elastic component 1125 may drive the second rod 1123 to rotate about the first connecting shaft 1124 as well. The receiving member 1120 may have an end (or be referred to a bottom end) connected to the inner surface of the housing 210/510 via a second connecting shaft 1126. When the second rod 1123 is caused to rotate about the first connecting shaft 1124, the second rod 1123 may push the receiving member 1120 to rotate about the second connecting shaft 1126. The receiving member 1120 may be flexible, and may include at least one flexible/soft/elastic material. Due to the flexibility of the receiving member 1120, the receiving member 1120 may be pushed to bend toward the local part 1190, so as to make it comfortable for the local part 1190. As shown in FIG. 11, T indicates the arc trajectories of the receiving member 1120, the first rod 1122, and the second rod 1123, respectively. It is understood that the trajectories T are only for demonstration purposes. In some embodiments, one or more of the trajectory lines of the receiving member 520, the first rod 1122, and the second rod 1123 may be different form the trajectories T shown in FIG. 11.

When the second rod 1123 is a straight rigid rod, the head of the subject may not be in good contact with the receiving member 1120, which may result in low accuracy of the scan data. Therefore, in some embodiments, the second rod 1123 may include a connecting arm 1231 and a pushing arm 1232. One end of the connecting arm 1231 may be pivotally connected to the first rod 1122, and the other end of the connecting arm 1231 may be connected with the pushing arm 1232. The pushing arm 1232 may be connected to the upper part (with respect to the Y direction) of the receiving member 1120, and the may be bent toward the receiving member 1120. Such a configuration may cause that, when the second rod 1123 is pushing the receiving member 1120, the upper end of the receiving member 1120 may be bent downward, and be in closer conformity to the local part 1190. The end of the pushing arm 1232 connected to the receiving member 1120 may penetrate through the supporting shell 515 when the receiving system 1100 is adopted in the head coil apparatus 500.

Figure 13:
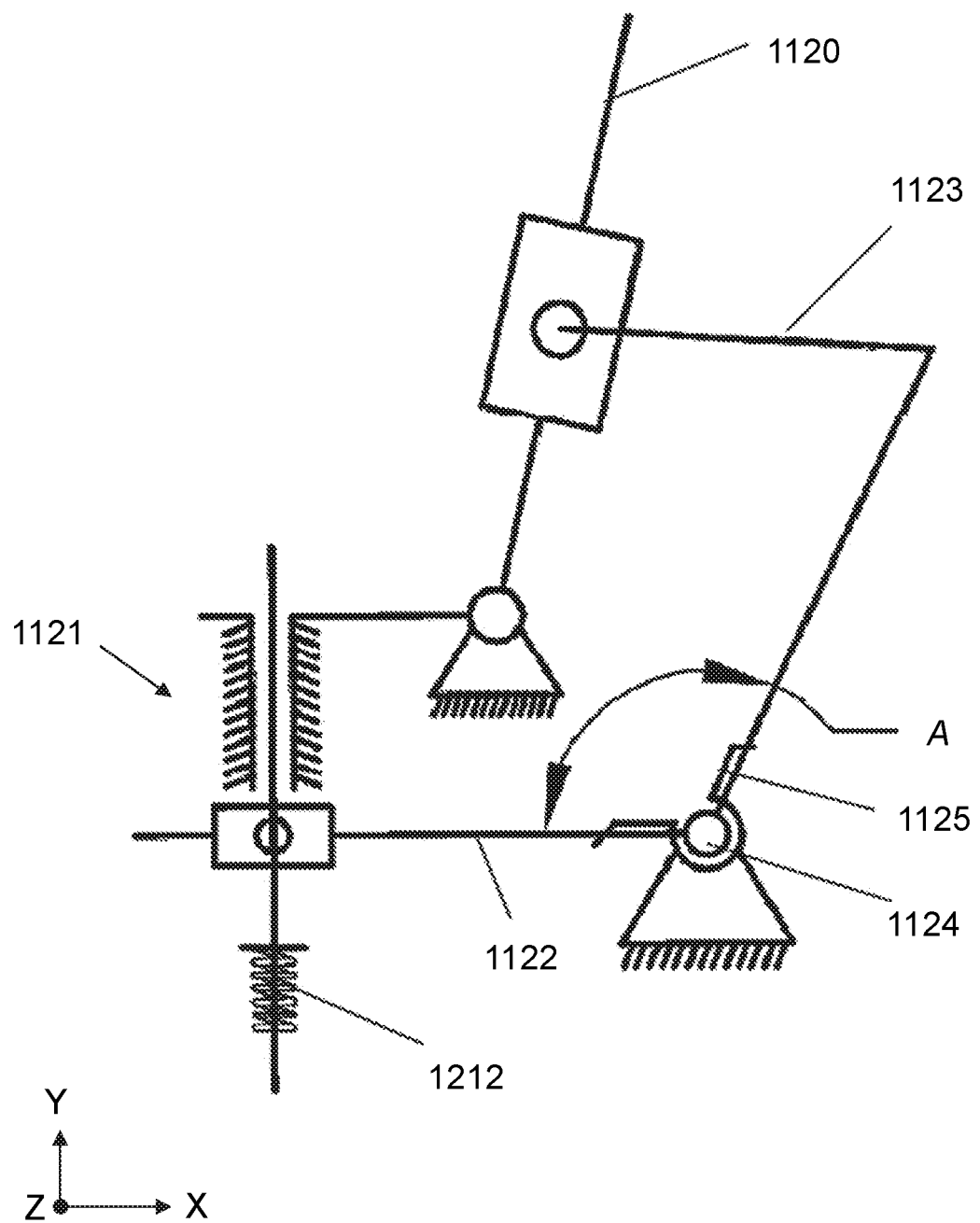
FIG. 13 is a schematic diagram illustrating the receiving system illustrated in FIG. 11 in the idle state according to some embodiments of the present disclosure.
Figure 14:
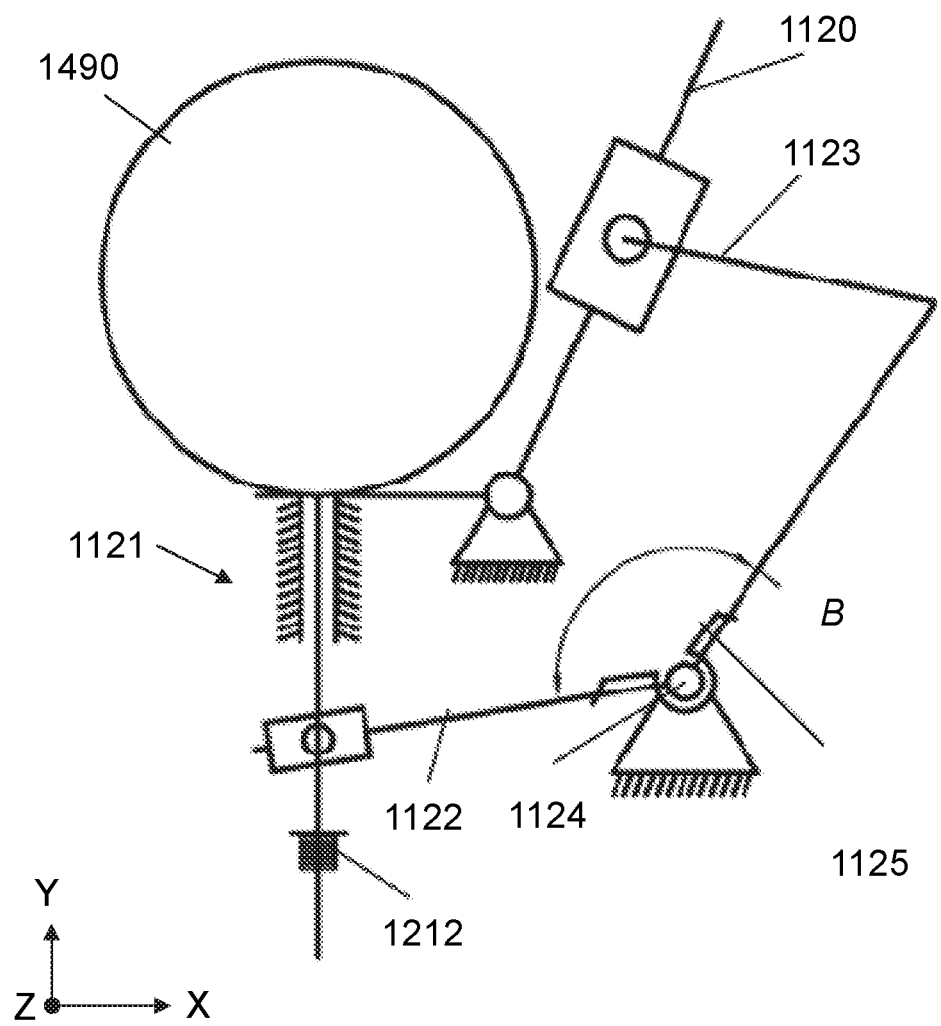
FIG. 14 is a schematic diagram illustrating the receiving system illustrated in FIG. 11 in the presence of a local part with a relatively small size according to some embodiments of the present disclosure.
Figure 15:
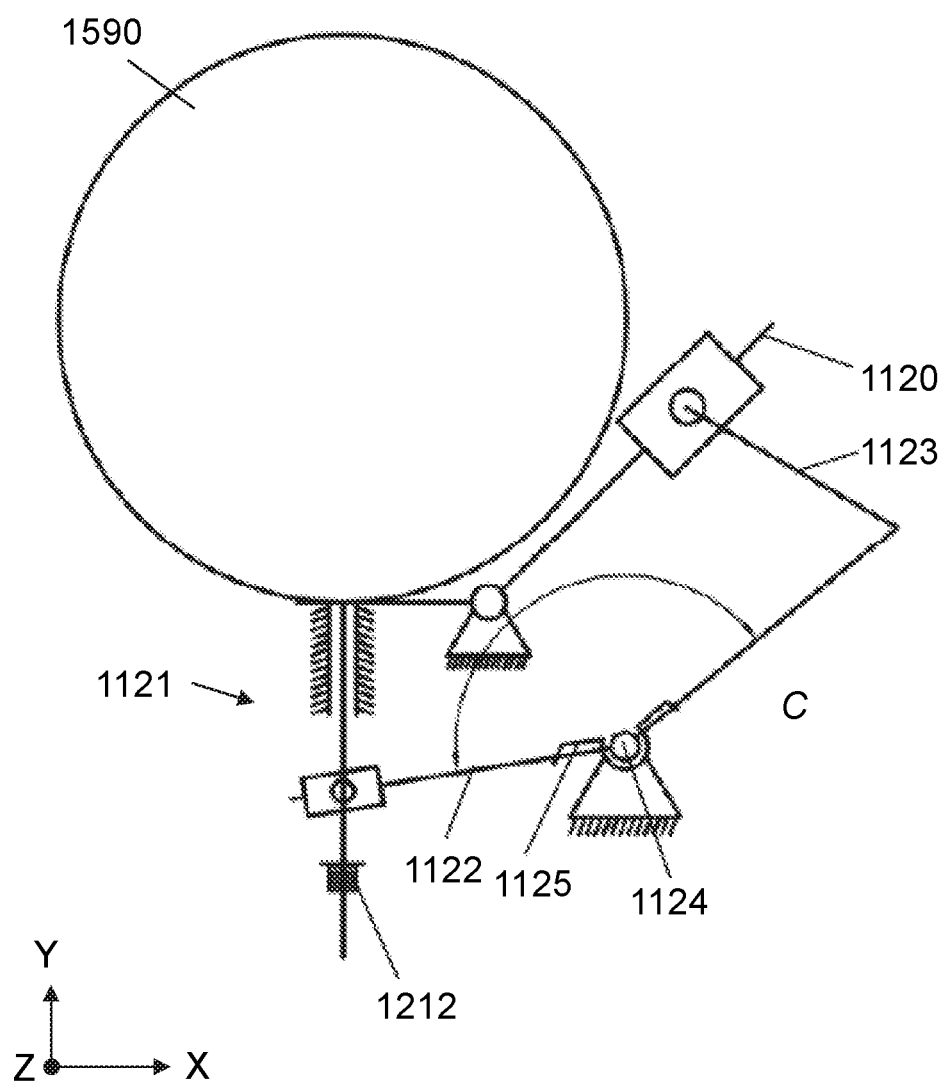
FIG. 15 is a schematic diagram illustrating the receiving system illustrated in FIG. 11 in the presence of a local part with a relatively big size according to some embodiments of the present disclosure.

In some embodiments, the angle between the first rod 1122 and the second rod 1123 may be greater than 90° when the receiving system 1100 is in an idle state, i.e., the pressing member 1121 is not pressed down by the local part 1190. The operating mechanism of the receiving system 1100 may be demonstrated by FIGS. 13 to 15. FIG. 13 is a schematic diagram illustrating the receiving system 1100 illustrated in FIG. 11 in the idle state according to some embodiments of the present disclosure. As shown in FIG. 13, the angle between the first rod 1122 and the second rod 1123 is A (e.g., 115°). FIG. 14 is a schematic diagram illustrating the receiving system 1100 illustrated in FIG. 11 in the presence of a local part 1490 with a relatively small size according to some embodiments of the present disclosure. As shown in FIG. 14, the angle between the first rod 1122 and the second rod 1123 is B (e.g., 130°). FIG. 15 is a schematic diagram illustrating the receiving system 1100 illustrated in FIG. 11 in the presence of a local part 1590 with a relatively big size according to some embodiments of the present disclosure. As shown in FIG. 15, the angle between the first rod 1122 and the second rod 1123 is C (e.g., 150°). As can be seen from FIGS. 13 to 15, the greater the pressure applied to the pressing member 1121 by the local part to be scanned, the greater the angle between the first rod 1122 and the second rod 1123. When the pressing member 1121 is fully pressed down by the local part to be scanned, the angle between the first rod 1122 and the second rod 1123 may be adjustable according to the size of the local part to be scanned (e.g., the head of a patient), so that the receiving member 1120 may conform to the head of the patient.

In the above configuration, after the patient is lying down, the head and the neck of the patient may press down the pressing member 1121, then the head/neck of the patient may be in close contact with the receiving members 1120, and the distances between the coils thereof and the head/neck of the patient may be minimized. The flexible component of the receiving members 1120 and the fully-pressed-down pressing member 1121 may keep the patient comfortable. It is also possible to add cushions on the supporting shell 515 and the pressing member 1121 to make the head coil apparatus 500 to be more comfortable. In some embodiments, the elastic component 1125 may be pre-pressed before being mounted on the receiving system 1100, so that the receiving members 1120 may exert a minimized pressure to the head/neck of the patient. Therefore, the receiving members 1120 may be in close contact with a local part having a relatively small size. Also, the angle between the first rod 1122 and the second rod 1123 may be limited to improve the stability of the receiving system 1100.

In some embodiments, to ensure that both sides of the head/neck of the parent are in contact with the pair of receiving members 1120, the pair of first rods 1122 and the pair of second rods 1123 may be arranged on both lateral sides of the pressing member 1121. In some specific embodiments, the pair of first receiving members 511 and the pair of second receiving members 512 of the head coil apparatus 500 illustrated in FIGS. 5 and 6 may each be connected to a receiving system 1100. The bottom ends of the first receiving members 511 and the second receiving members 512 may each be pivotally mounted on the supporting shell 515 via a second connecting shaft 1126. The upper parts of the first receiving members 511 and the second receiving members 512 may be respectively connected to the corresponding second rods 1123 of the corresponding driving mechanisms 1130. When the neck and the head of the patient are placed on the activation members 511-1 and 511-2, the first receiving members 511 and the second receiving members 512 may be driven to bend/rotate toward the neck and the head of the patient, so that the first receiving members 511 may conform to the neck of the patient, and the second receiving members 512 may conform to the head of the patient.

In some embodiments, the pressing member 1121 may include a pressing protrusion 1211, a return spring 1212, and a pair of connecting plates 1213 (e.g., as illustrated in FIGS. 7 and 8). The pair of connecting plates 1213 may be connected to both lateral sides of the pressing protrusion 1211 respectively. The return spring 1212 may be disposed at the bottom (with respect to the Y direction) of the pressing protrusion 1211. The pair of connecting plates 1213 may be connected to the pair of first rods 1122, respectively.

The pressing protrusion 1211 may penetrate through the supporting shell 515 and can be pressed down by the head of the subject. The return spring 1212 may be disposed directly below the pressing protrusion 1211, so that the pressing member 1121 can be restored to the original state in the absence of an external force. The pair of connecting plates 1213 may each include a sliding slot 1214. The pair of first rods 1122 may each be pivotally connected to the corresponding connecting plate 1213 via a third connecting shaft 1215, and the third connecting shaft 1215 may move through the sliding slot 1214. When the pressing protrusion 1211 is pressed down by the local part 1190, the pressing protrusion 1211 may drive the pair of first rods 1122 connected to the connecting plates 1213 to rotate about the third connecting shaft 1215. As a result, the pair of first/second receiving members 511/512 can move (e.g., rotate) and/or bend toward each other, so as conform to the neck/head of the patient.

It is noted that the receiving system 1100 illustrated in FIGS. 11 to 15 are only for demonstration purposes and not intended to be liming. For example, in different embodiments, the second rod 1123 may be a one-piece structure or a separable structure (e.g., formed by detachably connecting the connecting arm 1231 and the pushing arm 1232). As another example, in some embodiments, the pair of connecting plates 1213 and the pressing protrusion 1211 may also be integrated into a one-piece structure.

In some embodiments, a plurality of coils of the second coil assembly may be respectively disposed inside the first fixed scan section 532, the second fixed scan section 513, the third fixed scan section 514, and the supporting shell 515. A plurality of first coil assemblies may be respectively disposed inside the pair of first receiving members 511 and the pair of second receiving members 512. A third coil assembly may be disposed inside the movable scan section 531. The plurality of first coil assemblies, the second coil assembly, and the third coil assembly may be able to receive MR signals of corresponding portions of the head/neck of the patient.

In some embodiments, adjacent coils in the first/second/third coil assembly may be partially overlapped to decouple the coils. It is noted that other decoupling techniques, such as a decoupling capacitor or a decoupling inductor, may also be introduced into the first/second/third coil assembly for the decoupling of coils. The decoupling technique adopted in the present disclosure is not specifically limited.

Figure 16:
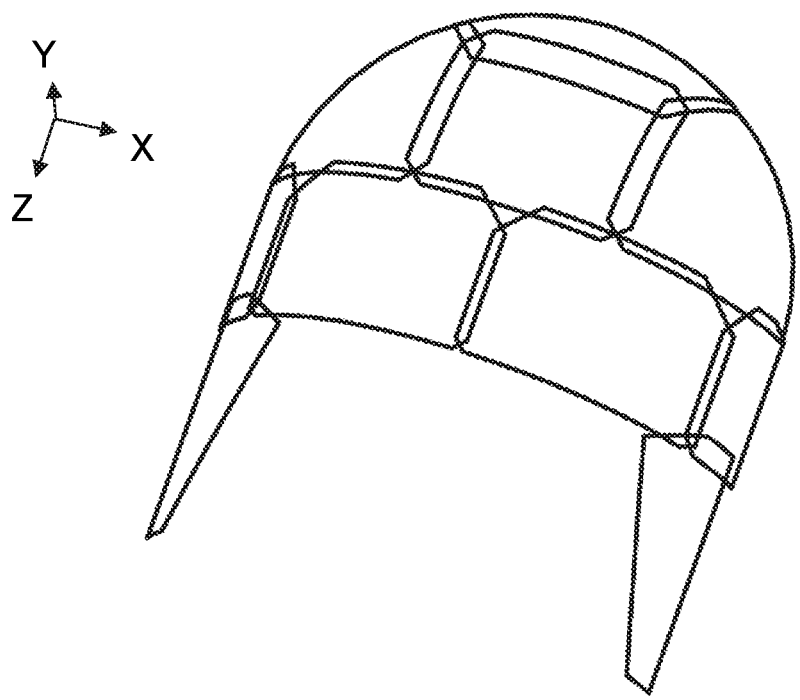
FIG. 16 is a schematic diagram illustrating an exemplary layout of coils disposed inside the top component of the head coil apparatus illustrated in FIG. 8 according to some embodiments of the present disclosure.
Figure 17:
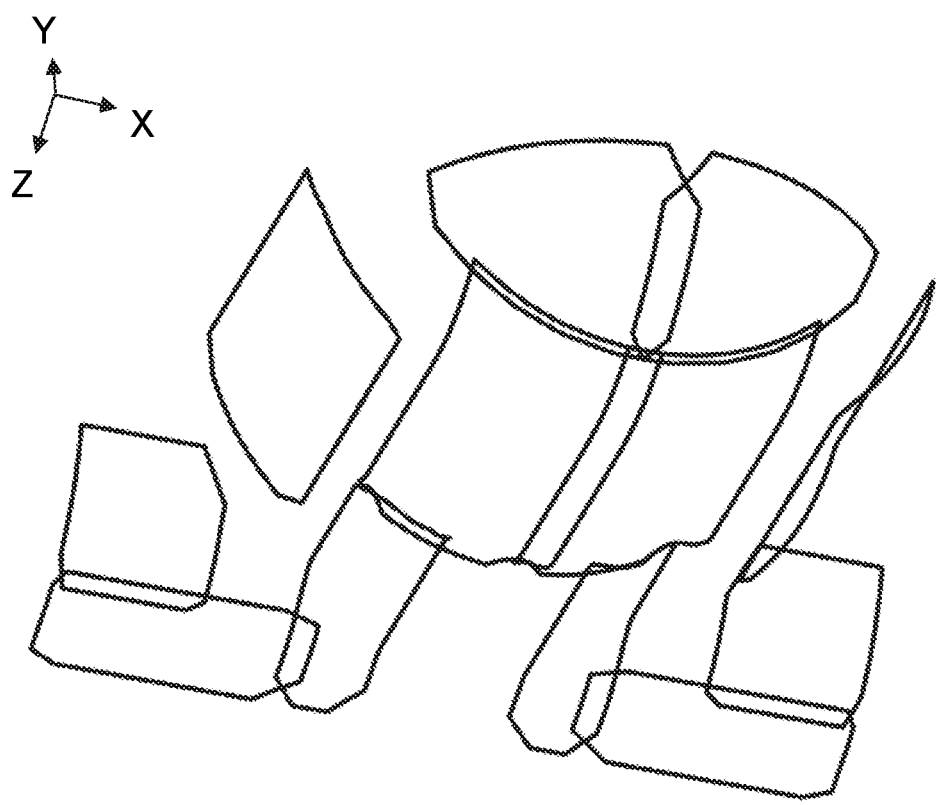
FIG. 17 is a schematic diagram illustrating an exemplary layout of coils disposed inside the bottom component of the head coil apparatus illustrated in FIG. 9 according to some embodiments of the present disclosure.

FIG. 16 is a schematic diagram illustrating an exemplary layout of coils disposed inside the top component 503 of the head coil apparatus 500 illustrated in FIG. 8 according to some embodiments of the present disclosure. FIG. 17 is a schematic diagram illustrating an exemplary layout of coils disposed inside the bottom component 501 of the head coil apparatus 500 illustrated in FIG. 9 according to some embodiments of the present disclosure. Coils of the first coil assembly may be disposed circumferentially in the first fixed scan section 532. Coils of the first coil assembly may also be disposed in the second fixed scan section 513, the third fixed scan section 514, and the supporting shell 515, which may correspond to the head, the neck, and the shoulders the subject, respectively. Since the first coil assembly is has a fixed configuration with respect to the head coil apparatus 500, the RF field generated thereby may be substantially stable.

Figure 18:
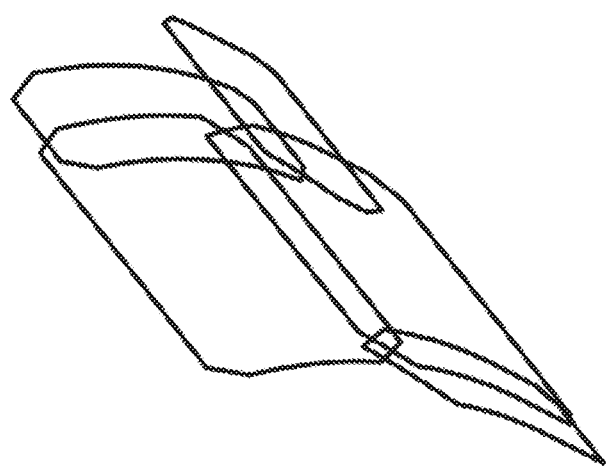
FIG. 18 is a schematic diagram illustrating an exemplary layout of coils disposed inside a first receiving member of the head coil apparatus illustrated in FIG. 10 according to some embodiments of the present disclosure.

FIG. 18 is a schematic diagram illustrating an exemplary layout of coils disposed inside a first receiving member 511 of the head coil apparatus 500 illustrated in FIG. 10 according to some embodiments of the present disclosure. As the first receiving member 511 may be driven by the corresponding driving mechanism 502 to change from the first configuration to the second configuration to conform to the neck of the patient, the first coil assembly thereof may be moved/bent/rotated with the first receiving member. For different patients, due to the different sizes/shapes of the heads, the corresponding second configurations of the first receiving member 511 (as well as that of the other receiving members) may be varied. As a result, the angle between the direction of the RF field generated by the second coil assembly of the first receiving member 511 (as well as that of the other receiving members) and the direction of the main magnetic field generated by the magnet assembly of the medical device 110 may be variable toward different patients.

FIG. 19 is a flow chart illustrating an exemplary process 1900 for performing an MR imaging on a local part of a subject with the imaging system 100 illustrated in FIG. 1 according to some embodiments of the present disclosure. The process 1900 may be implemented on the imaging system 100 and may be performed manually, automatically, or semi-automatically.

In some embodiments, the process 1900 may be in the form of instructions stored in a non-transitory storage device (e.g., the storage device 150, a built-in storage device of the data processing device 130), and may be executed or be invoked by a processor of a computing device (e.g., the data processing device 130). The computing device may be in communication (e.g., via the network 120 and/or wired connections) with the components of the imaging system 100 for transmitting the corresponding control signals to cause the components to perform the corresponding operations. In some embodiments, the computing device may implement the process 1900 in response to an instruction of a user. The user may be a patient (i.e., the subject) to receive the MR imaging, or an operator of the imaging system 100.

For demonstration purposes, the process 1900 may be described in connection with the local coil apparatus 200 illustrated in FIG. 2. It is understood that the process 1900 may also be implemented with a variant of the local coil apparatus 200, such as the head coil apparatus 500 illustrated in FIG. 5.

In 1910, the bottom component 216 of the housing 210 may be positioned on the table 112 of the imaging system 100. The bottom component 216 may just be placed on the table 112 or be detachably mounted on the table 112.

In some embodiments, the operation 1910 may be performed manually. Alternatively, the imaging system 100 may include a first robotic arm configured to perform the operation 1910 when the computing device executes the corresponding instructions.

In 1920, the subject may be positioned on the table 112, ensuring that, for each of the at least one receiving system of the local coil apparatus 200, the local part of the subject is properly placed on the activation member 240 of the receiving system so as to trigger the activation member 240.

In some embodiments, the subject may be a patient, and the patient may lay on the table 112 and properly trigger the activation member 240, or with the help of the operator.

In some embodiments, the subject may be non-living or not intelligent enough, then the operator of the imaging system 100 may perform the operation 1920. Alternatively, the imaging system 100 may include a second robotic arm configured to perform the operation 1920 when the computing device executes the corresponding instructions. The second robotic arm may be the first robotic arm or another robotic arm.

In 1930, for each of the at least one receiving system, the activation member 240 may cause the driving mechanism 250 to drive each of the one or more receiving members 230 to change from the first configuration to the second configuration to conform to the local part of the subject, so as to reduce a distance between the first coil assembly thereof and a corresponding portion of the local part. The above process has been fully described in the present disclosure and not repeated herein.

In 1940, the top component 215 of the housing 210 may be mounted on the bottom component 216.

In some embodiments, the operation 1940 may be performed manually. Alternatively, the imaging system 100 may include a third robotic arm configured to perform the operation 1940 when the computing device executes the corresponding instructions. The third robotic arm may be the first robotic arm, the second robotic arm, or another robotic arm.

In some embodiments, as mentioned before, the top component 215 may have a configuration similar to a receiving members 230. When the operation 1930 is completed, the top component 215 may also be automatically mounted on the bottom component 216.

In 1950, the table 112 may be caused to advance the subject to the scanning region 113 of the medical device 110, so that the local coil apparatus 200 is inside the scanning region 113. The operation 1950 may be performed by the operator of the imaging system 100 or the computing device when executing the corresponding instructions.

In 1960, the medical device 110 and the local coil apparatus 200 may be caused to perform an MR scanning together on the local part of the subject. The operation 1960 may be performed by the operator of the imaging system 100 or the computing device when executing the corresponding instructions. The resulting MR scan data may be processed by the data processing device 130 for generating an MR image of the local part.

Figure 20:
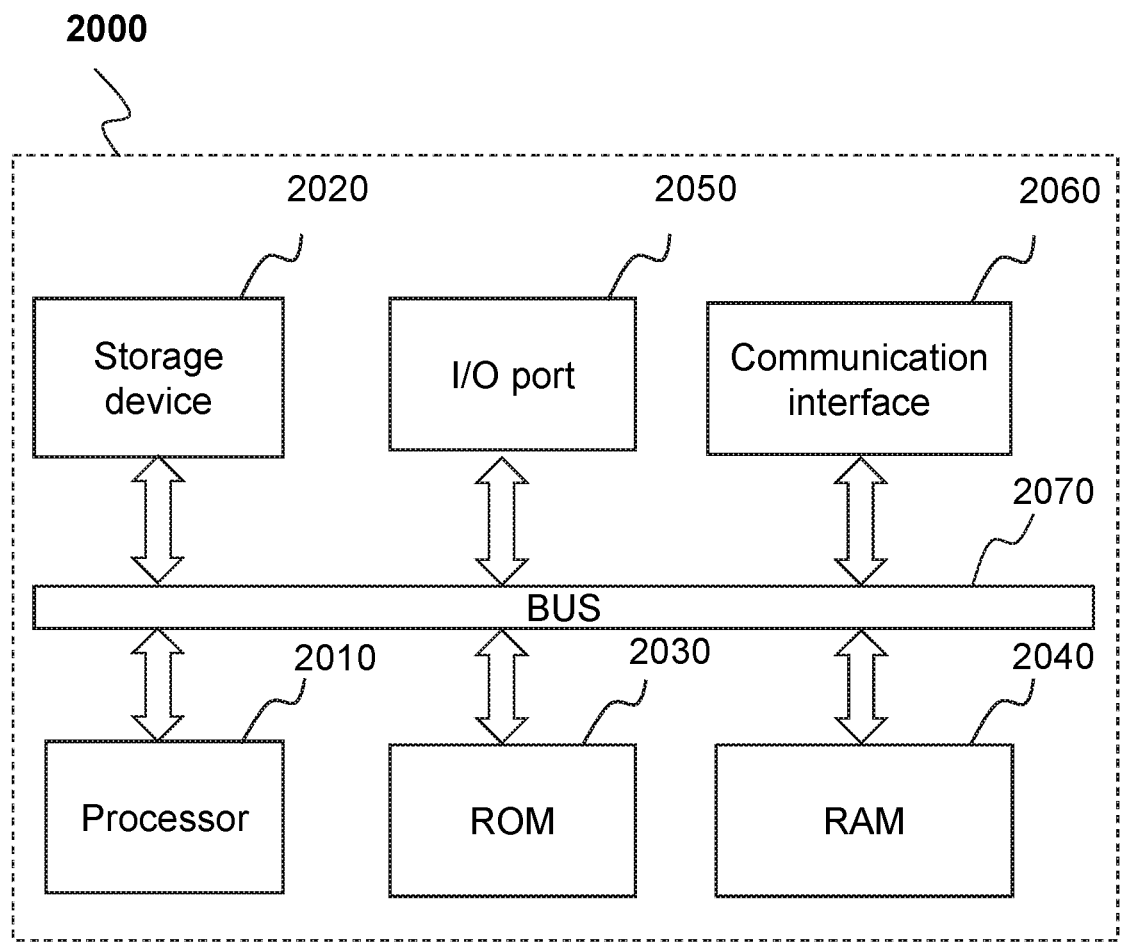
FIG. 20 illustrates an exemplary computing device for implementing one or more components of the imaging device illustrated in FIG. 1.

FIG. 20 illustrates an exemplary computing device for implementing one or more components of the imaging system 100 (e.g., data processing device 130, terminal device 14). For example, the computing device 2000 may be configured to perform one or more operations of the process 1900 in FIG. 19. The computing device 2000 may include a bus 2070, a processor 2010, a read only memory (ROM) 2030, a random-access memory (RAM) 2040, a storage 2020 (e.g., massive storage device such as a hard disk, an optical disk, a solid-state disk, a memory card, etc.), an input/output (I/O) port 2050, and a communication interface 2060. It is noted that the architecture of the computing device 2000 illustrated in FIG. 20 is only for demonstration purposes, and not intended to be limiting.

In some embodiments, the computing device 2000 may be a single device. Alternatively, the computing device 2000 may include a plurality of computing devices having the same or similar architectures as illustrated in FIG. 20, and one or more components of the computing device 2000 may be implemented by one or more of the plurality of computing devices.

The bus 2070 may couple various components of computing device 2000 and facilitate transferring of data and/or information between them. The bus 2070 may have any bus structure in the art. For example, the bus 2070 may be or may include a memory bus and/or a peripheral bus.

The I/O port 2050 may allow a transferring of data and/or information between the bus 2070 and a peripheral device (e.g., components of the imaging system 100 such as the medical device 110). For example, the I/O port 2050 may include a universal serial bus (USB) port, a communication (COM) port, a PS/20 port, a high-definition multimedia interface (HDMI) port, a video graphics array (VGA) port, a video cable socket such as an RCA sockets and a Mini-DIN socket, or the like, or a combination thereof.

The communication interface 2060 may allow a transferring of data and/or information between the network 120 and the bus 2070. For example, the communication interface 2060 may be or may include a network interface card (NIC), a Bluetooth™ module, an NFC module, etc.

The ROM 2030, the RAM 2040, and/or the storage 2020 may be configured to store computer readable instructions that can be executed by the processor 2010. The RAM 2040, and/or the storage 2020 may store date and/or information obtained from a peripheral device (e.g., an image capturing mechanism) and/or the network 120. The RAM 2040, and/or the storage 2020 may also store date and/or information generated by the processor 2010 during the execution of the instruction. In some embodiments, the ROM 2030, the RAM 2040, and/or the storage 2020 may be or may include the storage device 150 illustrated in FIG. 1.

The processor 2010 may be or include any processor in the art configured to execute instructions stored in the ROM 2030, the RAM 2040, and/or the storage 2020, so as to perform one or more operations or implement one or more modules/units disclosed in the present disclosure. Merely by way of example, the processor 2010 may include one or more hardware processors, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the computing device 2000 may include a plurality of processors 2010. The plurality of processors 2010 may operate in parallel for performing one or more operations disclosed in the present disclosure.

In some embodiments, one or more of the components of the computing device 2000 may be implemented on a single chip. For example, the processor 2010, the ROM 2030, and the RAM 2040 may be integrated into a single chip.

In some embodiments, the computing device 2000 may be a single device or include a plurality of computing devices having a same or similar architecture as illustrated in FIG. 20. In some embodiments, the computing device 2000 may implement a personal computer (PC) or any other type of work station or terminal device. The computing device 2000 may also act as a server if appropriately programmed.

Figure 21:
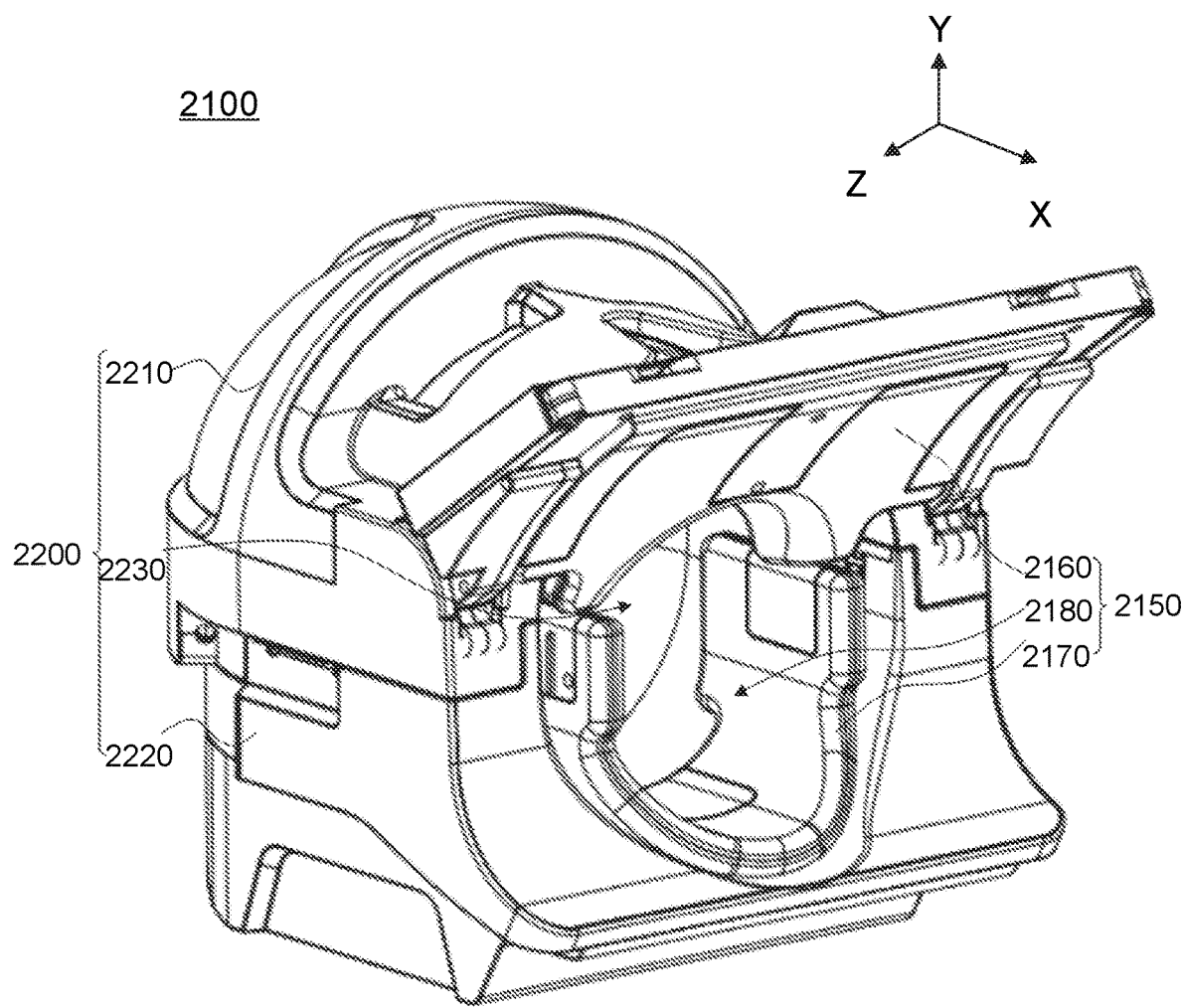
FIG. 21 is a schematic diagram illustrating an exemplary local coil apparatus according to some embodiments of the present disclosure.

FIG. 21 is a schematic diagram illustrating an exemplary local coil apparatus according to some embodiments of the present disclosure. The local coil apparatus 2100 may include a plurality of coils configured to specifically receive MR signals of the corresponding local part of the subject 115. The local coil apparatus 2100 may be in any proper form. In some specific embodiments, the subject 115 may be a patient, and the local part of the subject 115 may include the neck and the head (or a portion thereof) of the patient. The local coil apparatus 2100 may include a housing 2110 that provides an inner space, and a receiving system within the inner space configured to receive the neck and the head of the patient. In some embodiments, the receiving system may include a first receiving member 2150 and a second receiving member 2200 for receiving the neck and the head of the patient, respectively, according to the difference between the sizes/shapes of the head and the neck of the patient. In some embodiment, the local part of the subject 115 may also include other portions of the body of the patient, such as an arm and a corresponding hand of the patient, a lower leg and a corresponding foot of the patient. Accordingly, the first receiving member 2150 and a second receiving member 2200 may be configured for receiving the arm and the hand of the patient or the lower leg and the foot, respectively. The following descriptions are provided, unless otherwise stated expressly, with reference to the local part including the neck and the head of the patient for illustration purposes and not intended to be limiting.

Each of the first receiving member 2150 and the second receiving member 2200 may include a first coil assembly. The first coil assembly may be configured to receive MR signals during the MR scanning. The first coil assembly arranged in the first receiving member 2150 for receiving MR signals excited from the neck of the patient may also be referred to as neck coils. The first receiving member 2150 may also be referred to as a neck receiving member. The first coil assembly arranged in the second receiving member 2200 for receiving MR signals excited from the head of the patient may also be referred to as head coils. The second receiving member 2200 may also be referred to as a head receiving member.

In some embodiments, the first receiving member 2150 may include a first anterior receiving member 2160 and a first posterior receiving member 2170. The first anterior receiving member 2160 may be configured to accommodate the anterior neck of the patient, and also be referred to as anterior neck receiving member. The first posterior receiving member 2170 may be configured to accommodate the posterior neck of the patient, and also be referred to as posterior neck receiving member. The second receiving member 2200 may include a second anterior receiving member 2210 and a second posterior receiving member 2220. The second anterior receiving member 2210 may be configured to accommodate the anterior head (e.g., the face) of the patient, and also be referred to as anterior head receiving member. The second posterior receiving member 2220 may be configured to accommodate the posterior head of the patient, and also be referred to as posterior head receiving member. The first anterior receiving member 2160 and the first posterior receiving member 2170 may be mounted on the top side and the bottom side (with respect to the Y direction) of the inner surface of the housing 2110, respectively, and form a first portion of the inner space 2180 for receiving the neck of the patient. The first anterior receiving member 2160 and the first posterior receiving member 2170 may surround the first portion of the inner space 2180. The first coil assembly may be arranged in the first anterior receiving member 2160 and the first posterior receiving member 2170. In some embodiments, the first coil assembly arranged in the first anterior receiving member 2160 may also be referred to as anterior neck coils. The first coil assembly arranged in the first posterior receiving member 2170 may also be referred to as posterior neck coils.

The second anterior receiving member 2210 and the second posterior receiving member 2220 may be mounted on the top side and the bottom side (with respect to the Y direction) of the inner surface of the housing 2110, respectively, and form a second portion of the inner space 2230 for accommodating the head of the patient. The second anterior receiving member 2210 and the second posterior receiving member 2220 may surround the second portion of the inner space 2230. The first coil assembly may be arranged in the second anterior receiving member 2210 and the second posterior receiving member 2220. In some embodiments, the first coil assembly arranged in the second anterior receiving member 2210 may also be referred to as anterior head coils. The first coil assembly arranged in the second posterior receiving member 2220 may also be referred to as posterior head coils.

In some embodiments, the first anterior receiving member 2160 and the first posterior receiving member 2170 may be arranged at an opening of the second portion of the inner space 2230 formed by the second anterior receiving member 2210 and the second posterior receiving member 2220. The first anterior receiving member 2160 may be movable with respect to the first posterior receiving member 2170 and/or the second receiving member 2200. When the first anterior receiving member 2160 moves relative to the first posterior receiving member 2170 and/or the second receiving member 2200, a size of the first portion of the inner space 2180 may vary. The size of the first portion of the inner space 2180 may be adjusted according to a size of the neck of the patient by moving the first anterior receiving member 2160. In this case, the first anterior receiving member 2160 and the first posterior receiving member 2170 may conform to the neck of the patient, so as to reduce a distance between the first coil assembly in the first receiving member 2150 and the neck of the patient.

The first anterior receiving member 2160 may move with respect to the first posterior receiving member 2170 and/or the second receiving member 2200 in any suitable form. In some embodiments, the first posterior receiving member 2170 or the second receiving member 2200 may include one or more rotation joints. The first anterior receiving member 2160 may rotatably connected to first posterior receiving member 2170 or the second receiving member 2200 via the one or more rotation joints. The first anterior receiving member 2160 may rotate with respect to the first posterior receiving member 2170 and/or the second receiving member 2200 via the one or more rotation joints. In some embodiments, the first posterior receiving member 2170 or the second receiving member 2200 may include at least one sliding rail. The at least one sliding rail may have a curved shape, a linear shape, etc. For example, the at least one sliding rail may have a linear shape being in the Y direction. The first anterior receiving member 2160 may be mounted on the at least one sliding rail. The first anterior receiving member 2160 may move with respect to the first posterior receiving member 2170 and/or the second receiving member 2200 along the sliding rail. It should be noted that the one or more rotation joints and the at least one sliding rail are merely provided for illustration purposes, and not intended to be limiting. Any suitable structure that facilitates the movement of the first anterior receiving member 2160 with respect to the first posterior receiving member 2170 and/or the second receiving member 2200 may be used.

In some embodiments, the first anterior receiving member 2160 may also move with respect to the first posterior receiving member 2170 and/or the second receiving member 2200 along other directions (e.g., the Z direction). By moving along the Z direction, the first anterior receiving member 2160 may conform to the left side or the right side of the neck, so as to reduce a distance between the first coil assembly in the first receiving member 2150 and the left side or the right side of the neck of the patient. Therefore, an imaging of the left side or the right side of the neck (e.g., carotid arteries at the left side or the right side of the neck) may be realized.

In some embodiments, the first receiving member 2150 may be or include at least one flexible component. The at least one flexible component may include at least one soft/elastic/flexible material, such as cotton, wool, cloth, leather, artificial fiber, sponge, rubber, silica gel, polyurethane, ethylene vinyl acetate (EVA) copolymer, latex, or the like, or a combination thereof. The at least one flexible component may be arranged on an inner surface of the first anterior receiving member 2160 and/or the first posterior receiving member 2170 surrounding the first portion of the inner space 2180. When an external pressure is enforced on the flexible component (e.g., the neck of the patient is placed on the flexible component), the at least one flexible component may undergo an elastic deformation and conform to the neck of the patient. In some embodiments, the first coil assembly may be arranged in the flexible component. Due to the elastic deformation of the flexible component, the first coil assembly may be closer to the neck of the patient, and the imaging performance of the local coil apparatus 2100 may be improved. Similarly, the second receiving member 2200 may also be or include at least one flexible component.

In some embodiments, the first posterior receiving member 2170 may include a flexible component arranged on the inner surface of the first posterior receiving member 2170. The flexible component may have a U-shape or semicircular structure. The flexible component may have two free ends. When the neck of the patient is placed on the flexible component of the first posterior receiving member 2170, the two free ends may move towards each other and conform to at least a portion of the neck of the patient.

In some embodiments, outer surfaces of the at least one flexible component of the first anterior receiving member 2160 and/or the first posterior receiving member 2170 may be configured with a flexible band or wire. The flexible band or wire winding the at least one flexible component of the first anterior receiving member 2160 and/or the first posterior receiving member 2170 may tighten up after the neck of the patient is placed in the first portion of the inner space 2180. In this case, the at least one flexible component of the first anterior receiving member 2160 and/or the first posterior receiving member 2170 may conform to the neck of the patient, and the first coil assembly may be of a smaller dimension (e.g., the first coil assembly forming a circle, or a portion thereof, of a smaller diameter) than before the neck of the patient is placed in the first portion of the inner space 2180.

Before the MR scanning, the first anterior receiving member 2160 may be separated apart from the first posterior receiving member 2170. The first receiving member 2150 may be in an open state. Similarly, the second anterior receiving member 2210 may be separated apart from the second posterior receiving member 2220. The second receiving member 2200 may also be in an open state. The neck and the head of the patient may be placed in the first posterior receiving member 2170 and the second posterior receiving member 2220, respectively. Then the first anterior receiving member 2160 may be installed on the first posterior receiving member 2170 (i.e., the first receiving member 2150 may be in a closed state). The first anterior receiving member 2160 and the first posterior receiving member 2170 may be detachably mounted together to form the first portion of the inner space 2180. Similarly, the second anterior receiving member 2210 may installed on the second posterior receiving member 2220 (i.e., the second receiving member 2200 may be in a closed state). The second anterior receiving member 2210 and the second posterior receiving member 2220 may be detachably mounted together to form the second portion of the inner space 2230.

In some embodiments, the connection between the second anterior receiving member 2210 and the second posterior receiving member 2220 may be implemented using one or more pairs each including a positioning protrusion and a complementary positioning groove. By inserting the positioning protrusions into the corresponding positioning grooves, the second anterior receiving member 2210 and the second posterior receiving member 2220 may be connected. In some embodiments, the second anterior receiving member 2210 may also be connected to the second posterior receiving member 2220 via one or more rotation joints (not shown in the figure). It should be noted that the implementation of the second receiving member 2200 set forth above is merely for illustration purposes, and not intended to be limiting. In some embodiments, the second anterior receiving member 2210 and the second posterior receiving member 2220 may be integrated and inseparable.

Figure 22:
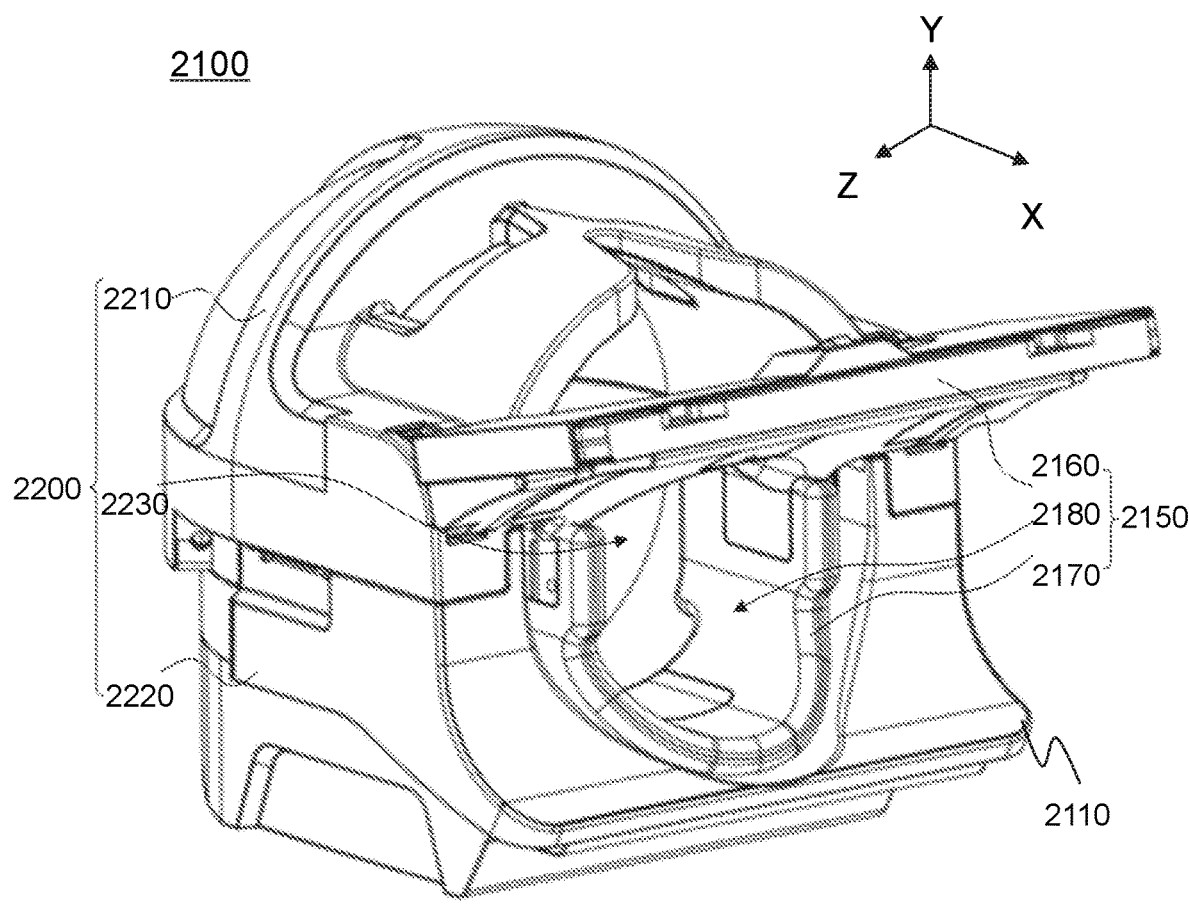
FIG. 22 is a schematic diagram of illustrating an exemplary second configuration of the local coil apparatus according to some embodiments of the present disclosure

When the first anterior receiving member 2160 is installed on the first posterior receiving member 2170, the first portion of the inner space 2180 for accommodating the neck of the patient may have a relatively large size. When the local coil apparatus 2100 is in a state for performing an MR scanning (e.g., when the setup of the local coil apparatus 2100 on the subject 115 is complete), the receiving member assembly may change from a first configuration (e.g., as shown in FIG. 21) to a second configuration (e.g., as shown in FIG. 22). The first configuration and the second configuration correspond to different sizes of the first portion of the inner space 2180. In the second configuration, at least a portion of the receiving member assembly (e.g., the first anterior receiving member 2160) may be in closer conformity to the local part (e.g., the neck of the patient) than in the first configuration.

FIG. 22 is a schematic diagram of illustrating an exemplary second configuration of the local coil apparatus according to some embodiments of the present disclosure. As illustrated in FIG. 22, when the receiving member assembly is in the second configuration, the first portion of the inner space 2180 of the local coil apparatus 2100 may have a smaller size than when the receiving member assembly is in the first configuration, and the first anterior receiving member 2160 may be in close conformity to the neck of the patient. To change from the first configuration to the second configuration, the first anterior receiving member 2160 may be moved (e.g., by an operator or a driving mechanism) to be closer to the first posterior receiving member 2170 so as to conform to the neck of the patient.

By moving the first anterior receiving member 2160, the size of the first portion of the inner space for receiving the neck of the patient may be changed conveniently and effectively, thereby improving the adaptability of the first receiving member 2150 to local parts of different sizes. For example, for a child, the size of the first portion of the inner space 2180 may be relatively small. For an adult, the size of the first portion of the inner space 2180 may be relatively large. In this case, the first coil assembly may be closer to the local part of the patient, a signal-to-noise ratio of the MR signal may be enhanced, and the imaging quality of the local part may be improved.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the first anterior receiving member 2160 may be movable with respect to a reference plane. The reference plane may be any plane that can be represented by the coordinate system. For example, the reference plane may be the X-Z plane. The movement of the first anterior receiving member 2160 with respect to the reference plane may enable at least a portion of the first coil assembly of the first anterior receiving member 2160 to conform to the neck of the patient.

Figure 23:
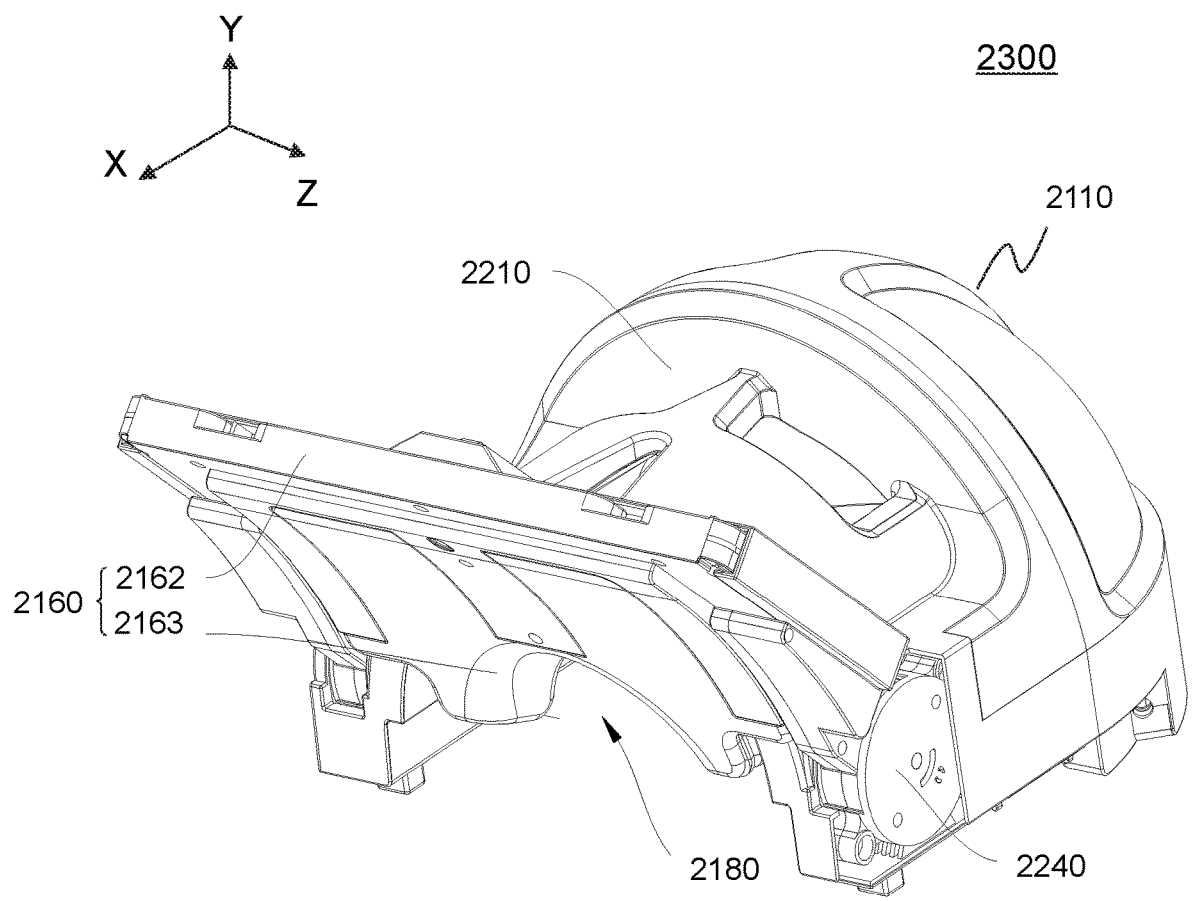
FIGS. 23 and 24 are schematic diagrams of an upper part of the local coil apparatus according to some embodiments of the present disclosure.
Figure 24:
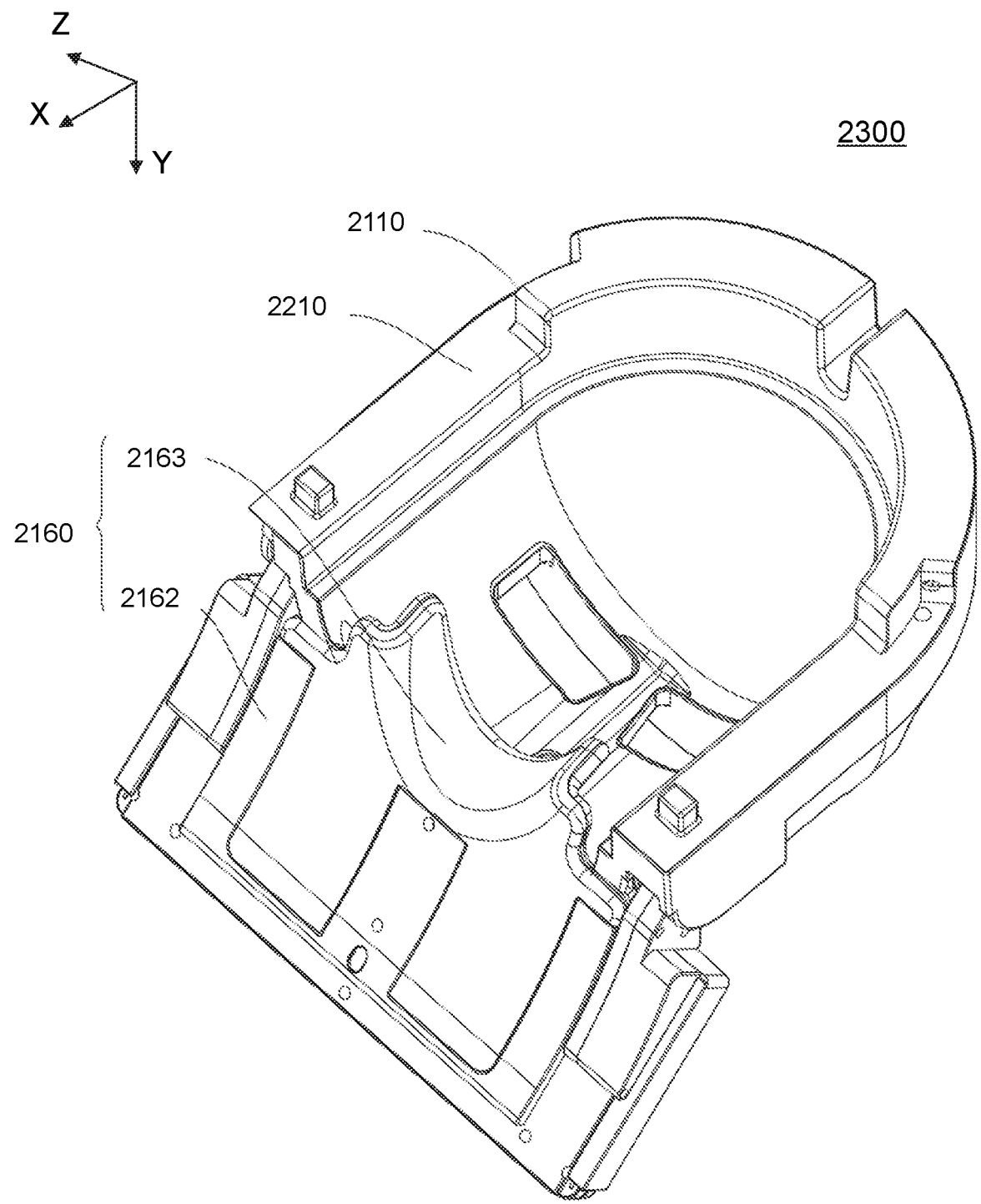

FIGS. 23 and 24 are schematic diagrams of an upper part of the local coil apparatus according to some embodiments of the present disclosure. FIG. 23 is a schematic diagram of the upper part of the local coil apparatus viewed from a positive direction of the Y axis to a negative direction of the Y axis. FIG. 24 is a schematic diagram of the upper part of the local coil apparatus viewed from the negative direction of the Y axis to the positive direction of the Y axis. The upper part of the local coil apparatus 2300 may include the top component of the housing 2110, the first anterior receiving member 2160 and the second anterior receiving member 2210. In some embodiments, the second anterior receiving member 2210 may including one or more rotation joints 2240. The first anterior receiving member 2160 may be rotatably connected to the second anterior receiving member 2210 via the one or more rotation joints 2240. A rotation joint set on the second anterior receiving member 2210 may be a structure that connects first anterior receiving member 2160 to the second anterior receiving member 2210, and enables a rotation of the first anterior receiving member 2160 around an axis. When the first anterior receiving member 2160 rotates around the axis by an angle, the size of the first portion of the inner space 2180 may be increased or decreased accordingly. The angle may be defined with reference to the coordinate system as illustrated in the figure. The rotatable connection between the first anterior receiving member 2160 and the second anterior receiving member 2210 may facilitate a smooth change of the size of the first portion of the inner space 2180. In addition, the rotatable connection may be easy to implement in the manufacture.

In some embodiments, the angle by which the first anterior receiving member 2160 rotates around the axis may be determined according to actual conditions. In some embodiments, the angle may be in a certain angle range. For example, the angle by which the first anterior receiving member 2160 rotates around the axis may range from 5 degrees to 50 degrees. In some embodiments, the angle range may be defined by the one or more rotation joints 2240. For example, at least one of the one or more rotation joints 2240 may include a stopper that determines an upper limit (e.g., 50 degrees) and a lower limit (e.g., 5 degrees) of the rotation range. In some embodiments, the upper limit and the lower limit of the angle range may be determined based on a big data analysis. For example, sizes (e.g., diameters) of necks of a large number of people may be statistically analyzed, and the upper limit and the lower limit of the angle range may be determined based on the statistical analysis.

In some embodiments, when the first anterior receiving member 2160 is positioned at a particular angle in the angle range, the first anterior receiving member 2160 may keep stationary at the angle by virtue of the one or more rotation joints 2240. In this case, when the first anterior receiving member 2160 conforms to the neck of the patient, the one or more rotation joints 2240 may sustain the weight of the first anterior receiving member 2160 to, instead of the neck of the patient, so that the load on the neck of the patient may be reduced. In some embodiments, at least one of the one or more rotation joints 2240 may include a damping structure. The damping structure may increase the friction when the rotation joints 2240 rotates. In this way, the first anterior receiving member 2160 can keep stationary at any angle within the angle range.

In some embodiments, the count or number of the rotation joints 2240 may be set according to actual needs. In some embodiments, the count or number of the rotation joints 2240 may be two. The two rotation joints 2240 may be set on the lateral sides (in the Z direction) of the second anterior receiving member 2210. The first anterior receiving member 2160 may be rotatably connected to the second anterior receiving member 2210 via the two rotation joints 2240. The first anterior receiving member 2160 may rotate around an axis formed by the two rotation joints 2240. The two rotation joints 2240 may facilitate a smooth movement of the first anterior receiving member 2160 with respect to the second receiving member 2200 or a part thereof (e.g., the second anterior receiving member 2210).

In actual applications, differences of the sizes of the necks of different patients may be greater than differences of the sizes of the heads of the different patients. Generally, the sizes of the heads of the different patients may be roughly the same. By setting the one or more rotation joints 2240 on the second anterior receiving member 2210, the first anterior receiving member 2160 may be movable with respect to the second receiving member 2200. In this case, the size of the first portion of the inner space 2180 for accommodating the neck of a patient may be adjusted independently.

In some embodiments, the first anterior receiving member 2160 may be rotatably connected to the second posterior receiving member 2220 through one or more rotation joints. If only the neck of the patient is scanned in the MR scanning process, the second anterior receiving member 2210 may be detached or separated from the second posterior receiving member 2220, and the first anterior receiving member 2160 may be rotatably connected to the second posterior receiving member 2220. In comparison to the second posterior receiving member 2220, the second anterior receiving member 2210 may be closer to the first anterior receiving member 2160, such that the structure of the rotation connection may be easier accordingly. In some embodiments, that least one rotation joint 2240 may be set on the second anterior receiving member 2210, and the other rotation joints 2240 may be set on the second posterior receiving member 2220. The first anterior receiving member may be rotatably connected to the second receiving member via the one or more rotation joints 2240. In some alternative embodiments, the one or more rotation joints 2240 may be set on the first posterior receiving members.

In some embodiments, the first anterior receiving member 2160 may further include a main body 2162 and a flexible component 2163. The flexible component 2163 may be attached to an inner surface of the main body 2162. The main body 2162 may conform to the neck of the patient through the flexible component 2163 in the second configuration. In some embodiments, at least a portion of the first coil assembly of the first anterior receiving member 2160 may be arranged in the flexible component 2163. The flexible component 2163 may undergo an elastic deformation and conform to the neck of the patient in the second configuration, and the at least a portion of the first coil assembly may be closer to the neck of the patient. Therefore, the signal-to-noise ratio of the MR signal regarding the neck of the patient may be enhanced. In addition, the flexible component 2163 may avoid pain or injuries on the neck of the patient when the first anterior receiving member 2160 with respect to the second receiving member 2200, thereby improving the comfort of the patient in the second configuration.

Figure 25:
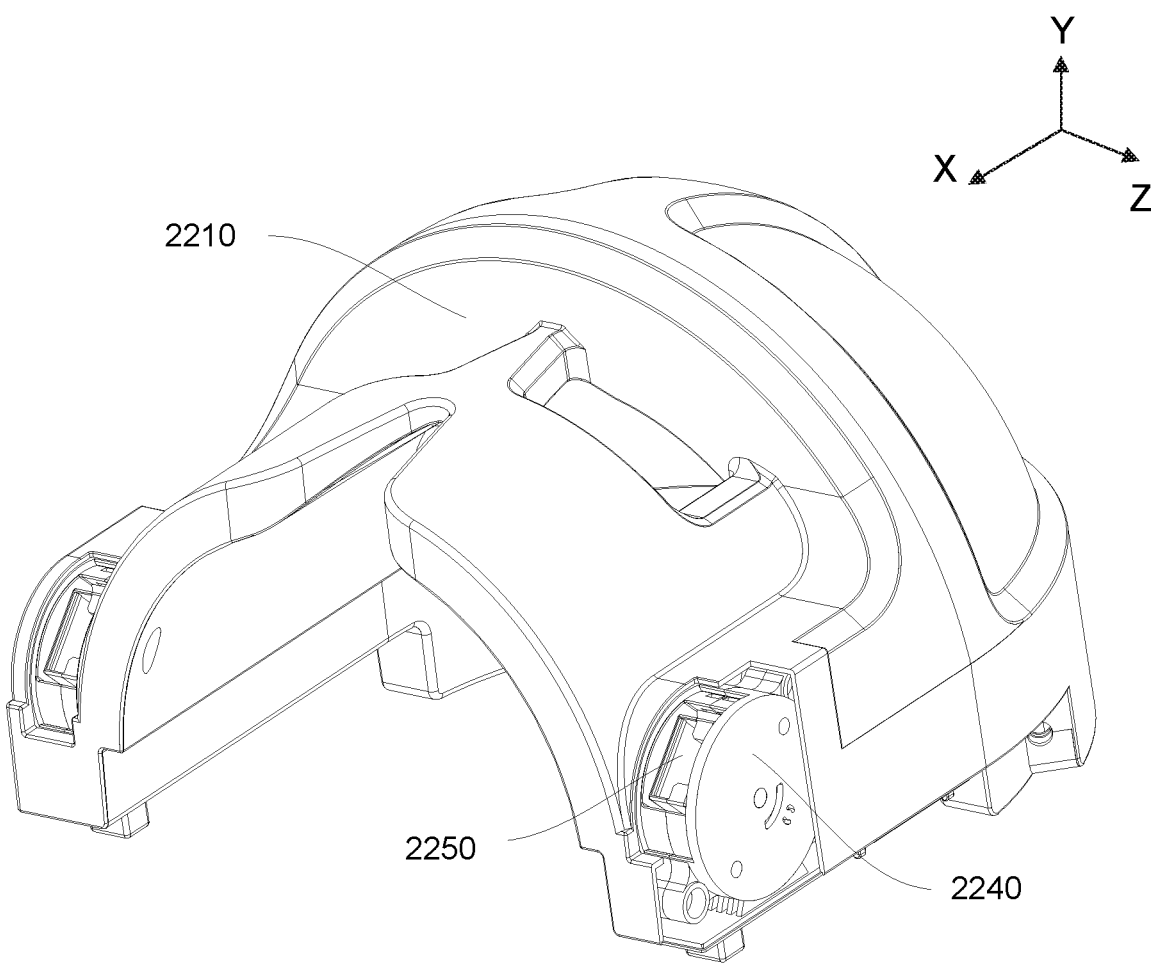
FIG. 25 is a schematic diagram illustrating an exemplary rotation joint according to some embodiments of the present disclosure.

FIG. 25 is a schematic diagram illustrating an exemplary rotation joint according to some embodiments of the present disclosure. As illustrated in FIG. 25, the rotation joints 2240 may be set on the second anterior receiving member 2210. The first anterior receiving member 2160 may have been detached or separated from the second anterior receiving member 2210. Thus, the first anterior receiving member 2160 is not shown in FIG. 25. In some embodiments, the rotation joints 2240 may include a socket part. The first anterior receiving member 2160 may include a plug-in part. The first anterior receiving member 2160 may be detachably plugged in the one or more rotation joints 2240 by inserting the plug-in part into the socket part. The detachable plugging connection may facilitate a rapid installation and disassembly of the first anterior receiving member 2160 with respect to the second receiving member 2200, and increase the replaceability of first anterior receiving member 2160 of different types, structures, and/or sizes.

In some embodiments, the first coil assembly of the first anterior receiving member 2160 may include an electrical access interface (not shown in the figure). Electric power may be supplied to the first coil assembly of the first anterior receiving member 2160 through the electrical access interface. The first coil assembly of the second receiving member 2200 may include a first electrical interface 2250. Electric power from the first coil assembly of the second receiving member 2200 may be output thought the first electrical interface 2250. In some embodiments, the first electrical interface 2250 may configured in at least one of the one or more rotation joints 2240 (e.g., the socket part of the rotation joints 2240). The electrical access interface may be configured at the plug-in part of the first anterior receiving member 2160. The electrical access interface may be connected to the first electrical interface 2250 when the first anterior receiving member 2160 is plugged in the one or more rotation joints 2240. A first connection path between the first anterior receiving member 2160 and the second receiving member 2200 may be established. Electric power in the first coil assembly of the second receiving member 2200 may be transmitted to the first coil assembly of the first anterior receiving member 2160 via the first connection path.

In addition, signals such as control signals, MR signals, etc., may also be transmitted via the first connection path. The first connection path may provide an integrated power supply and signal transmission for the first anterior receiving member 2160 and the second receiving member 2200, and simplify the structure of the local coil apparatus 2100.

Besides, the interfaces may include universal interfaces (e.g., universal serial bus (USB) interfaces), which may be stable and have a high compatibility. For example, when the first receiving member 2150 is used alone, the first coil assembly of the first anterior receiving member 2160 may be powered by an external power source having a universal interface by connecting the electrical access interface to the universal interface.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the rotation joints 2240 may include a plug-in part. The first anterior receiving member 2160 may include a socket part. The first anterior receiving member 2160 may be detachably plugged in the one or more rotation joints 2240 by inserting the plug-in part into the socket part.

Figure 26:
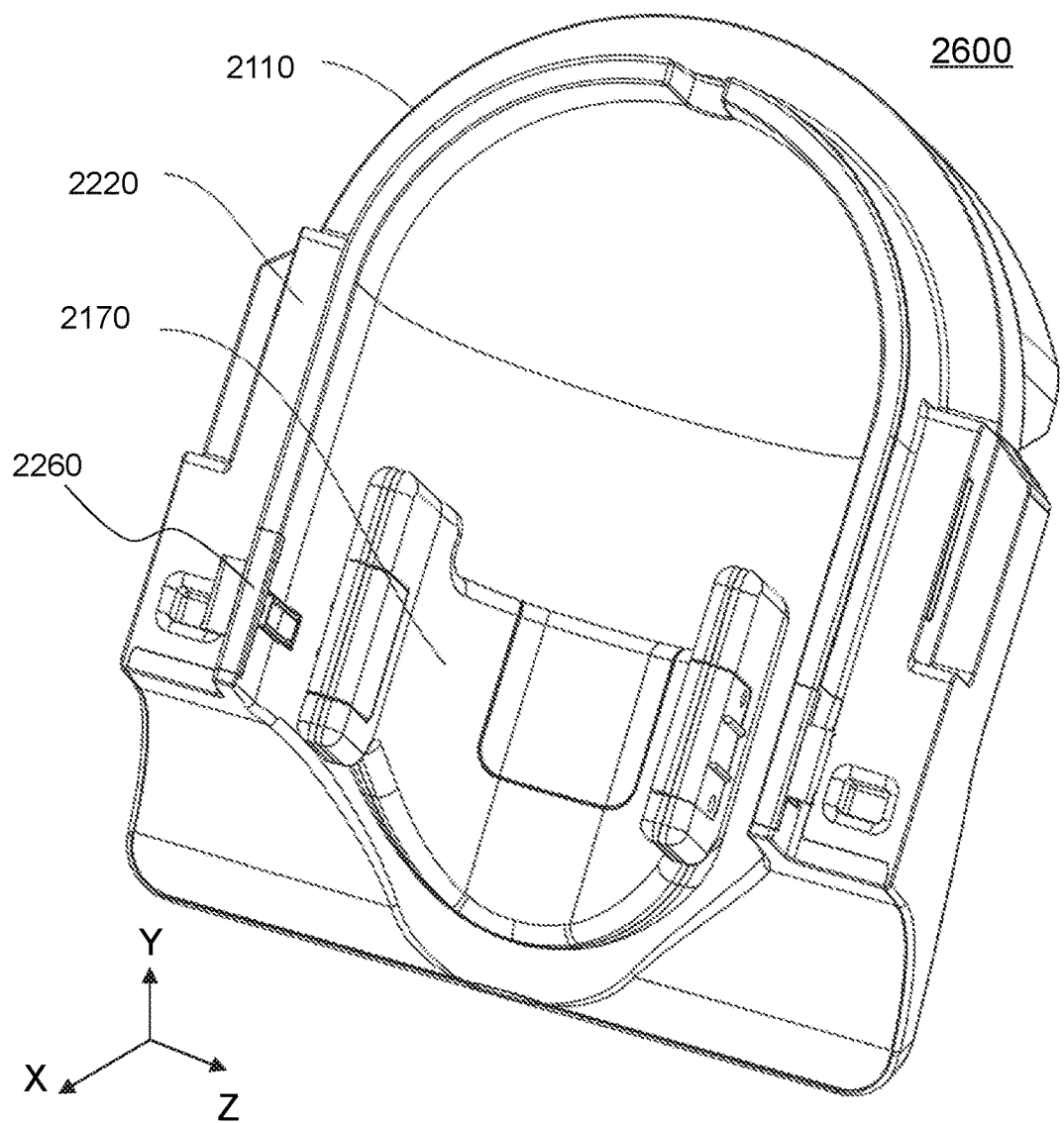
FIG. 26 is a schematic diagram of a lower part of the local coil apparatus according to some embodiments of the present disclosure.

FIG. 26 is a schematic diagram of a lower part of the local coil apparatus according to some embodiments of the present disclosure. The lower part of the local coil apparatus 2600 may include the bottom component of the housing 2110, the first posterior receiving member 2170 and the second posterior receiving member 2220. When the patient is placed on the table 112, the neck of the patient may be in a direct contact with the first posterior receiving member 2170. In some embodiments, the entire first posterior receiving member 2170 may be a flexible component. Alternatively, a portion of the first posterior receiving member 2170 (e.g., a middle portion of the first posterior receiving member 2170) may be or include a flexible component. The flexible component may be made of cotton, wool, cloth, leather, artificial fiber, sponge, rubber, silica gel, polyurethane, ethylene vinyl acetate (EVA) copolymer, latex, or the like, or a combination thereof. At least a portion of the first coil assembly of the first posterior receiving member 2170 may be arranged in the flexible component. The flexible component may undergo an elastic deformation and conform to the neck of the patient when the neck of the patient is placed on the first posterior receiving member 2170, and the at least a portion of the first coil assembly in the flexible component may be closer to the neck of the patient. Therefore, the signal-to-noise ratio of the MR signal regarding the neck of the patient may be enhanced. In addition, the flexible component may avoid or reduce pain or injuries caused by hard contact between the neck of the patient and a solid surface.

In some embodiments, the entire first posterior receiving member 2170 may be a U-shaped or semi-circular flexible component. The flexible component may have two free ends on the lateral sides. When the neck of the patient is placed on the flexible component of the first posterior receiving member 2170, the two free ends may move towards each other and conform to at least a portion of the neck of the patient. The first coil assembly in the flexible component may be closer to the neck of the patient.

In some embodiments, the second anterior receiving member 2210 and the second posterior receiving member 2220 may be detachably mounted together to form the second portion of the inner space 2230. When the second anterior receiving member 2210 may installed on the second posterior receiving member 2220 (i.e., the second receiving member 2200 may be in a closed state), the second anterior receiving member 2210 may be configured to compress the first posterior receiving member 2170 from the lateral sides (the Z direction) so that the two free ends may press against at least a portion of the neck. The pressure from the second anterior receiving member 2210 enforced on the first posterior receiving member 2170 may improve the adaptability of the first posterior receiving member 2170 to necks of different sizes.

Figure 27:
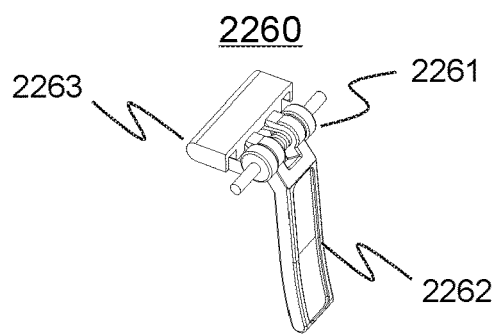
FIG. 27 illustrates an exemplary torsional spring compressed bar according to some embodiments of the present disclosure.

The second anterior receiving member 2210 may compress the first posterior receiving member 2170 from the lateral sides directly or via an intermediate structure between the second anterior receiving member 2210 and the first posterior receiving member 2170. The intermediate structure may transfer the pressure from the second anterior receiving member 2210. In some embodiments, the intermediate structure may be an elastic structure. Merely for illustration, the intermediate structure may include at least one torsional spring compressed bar 2260 set at the lateral sides of the first posterior receiving member 2170. An exemplary torsional spring compressed bar may be found in FIG. 27. As shown in FIG. 27, the torsional spring compressed bar 2260 may include a torsional spring 2261 and two ends 2262 and 2263. The two ends 2262 and 2263 may include a bar, a plate, etc. If one of the two ends (e.g., the end 2263) is impacted by an external force, the external force may be transferred to the other end (e.g., the end 2262) via the torsional spring 2261. When the second anterior receiving member 2210 is installed on the second posterior receiving member 2220 (i.e., the second receiving member 2200 may be in a closed state), the second anterior receiving member 2210 may compress the end 2263 of the torsional spring compressed bar 2260, and the end 2263 may transfer the pressure from the second anterior receiving member 2210 (e.g., the weight of the second anterior receiving member 2210) to the end 2262 via the torsional spring 2261. Then the end 2262 may further transfer the pressure to the first posterior receiving member 2170, such that the two free ends of the first posterior receiving member 2170 may press against at least a portion of the neck. In some embodiments, a torsion generated by the torsional spring 2261 and/or sizes or shapes of the two ends 2262 and 2263 may be designed according to actual needs. In this case, even for the neck of a child, the first posterior receiving member 2170 may conform to the neck.

In some embodiments, the second posterior receiving member 2220 may also be or include a U-shaped or semicircular flexible component. The flexible component may have two free ends on the lateral sides. When the head of the patient is placed on the flexible component of the second posterior receiving member 2220, the two free ends may move towards each other and conform to at least a portion of the head of the patient. The first coil assembly in the flexible component may be closer to the head of the patient.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the receiving system may further include an activation member and a driving mechanism in communication with the activation member. In some embodiments, the activation member may be set on the first posterior receiving member 2170. The driving mechanism may be physically connected to the first posterior receiving member 2170. When the neck of the patient is placed on the activation member, the activation member may detect the presence of the neck due to a pressure (e.g., weight of the neck) enforced on the activation member. The activation member may cause the driving mechanism to drive the receiving member assembly to change from the first configuration to the second configuration to reduce a distance between the first posterior receiving member 2170 and the neck of the patient. In some embodiments, the driving mechanism may be further connected to the second posterior receiving member 2220 physically. When the receiving member assembly changes from the first configuration to the second configuration, a distance between the second posterior receiving member 2220 and head of the patient may also be reduced.

Figure 28:
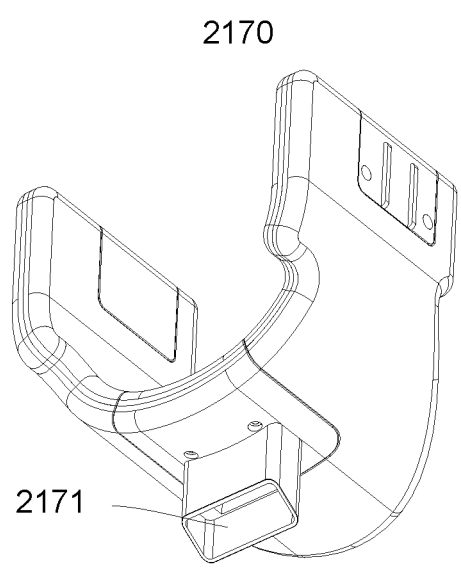
FIG. 28 illustrates an exemplary first posterior receiving member according to some embodiments of the present disclosure.
Figure 29:
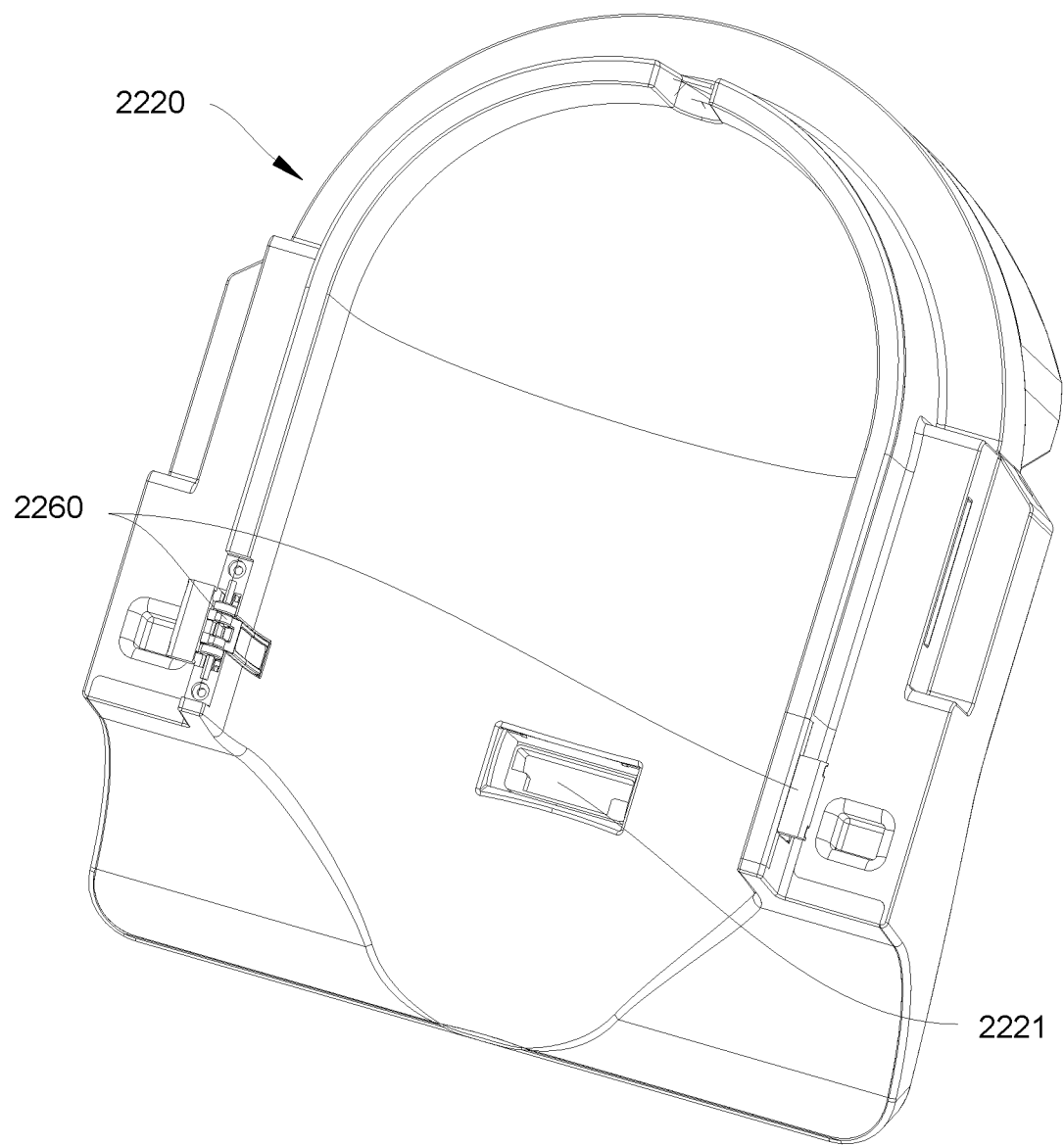
FIG. 29 illustrates an exemplary second posterior receiving member according to some embodiments of the present disclosure.

FIG. 28 illustrates an exemplary first posterior receiving member according to some embodiments of the present disclosure. As illustrated in FIG. 28, the first posterior receiving member 2170 may include a second electrical interface 2171. Electric power may be supplied to the first coil assembly of the first posterior receiving member 2170 through the second electrical interface 2171. FIG. 29 illustrates an exemplary second posterior receiving member according to some embodiments of the present disclosure. As illustrated in FIG. 29, the second posterior receiving member 2220 may include a third electrical interface 2221. Electric power from the first coil assembly of the second posterior receiving member 2220 may be output thought the third electrical interface 2221. In some embodiments, the second electrical interface 2171 may be operably coupled to the third electrical interface 2221. Then a second connection path between the first posterior receiving member 2170 and the second receiving member 2200 may be established. Electric power in the first coil assembly of the second receiving member 2200 may be transmitted to the first coil assembly of the first posterior receiving member 2170 via the second connection path. In addition, signals such as control signals, MR signals, etc., may also be transmitted on the second connection path. The second connection path may provide an integrated power supply and signal transmission for the first posterior receiving member 2170 and the second receiving member 2200, and simplify the structure of the local coil apparatus 2100. Besides, the interfaces may be universal interfaces (e.g., universal serial bus (USB) interfaces), which may be stable and have a high compatibility. For example, when the first receiving member 2150 is used alone, the first coil assembly of the first posterior receiving member 2170 may be powered by an external power source having a universal interface by connecting the electrical access interface to the universal interface. In some embodiments, the first posterior receiving member 2170 may also be detachably connected to the second posterior receiving member 2220 by coupling the second electrical interface 2171 to the third electrical interface 2221. It should be noted that connection means between the first posterior receiving member 2170 and the second posterior receiving member 2220 may not be limited in the present disclosure. Exemplary connection means may include bolted connections, snap joints, rotation joints, adhesive joints, or the like, or a combination thereof.

Having thus described the basic concepts, it may be rather apparent to those skilled in the art after reading this detailed disclosure that the foregoing detailed disclosure may be intended to be presented by way of example only and may be not limiting. Various alterations, improvements, and modifications may occur and are intended to those skilled in the art, though not expressly stated herein. These alterations, improvements, and modifications are intended to be suggested by this disclosure, and are within the spirit and scope of the embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment may be included in at least one embodiment of the present disclosure. Therefore, it may be emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that may be not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an subject oriented programming language such as Java, Scala, Smalltalk, Eiffel, JADE, Emerald, C++, C #, VB. NET, Python or the like, conventional procedural programming languages, such as the "C" programming language, Visual Basic, Fortran 20103, Perl, COBOL 201020, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, may be not intended to limit the claimed processes and methods to any order except as may be specified in the claims. Although the above disclosure discusses through various examples what may be currently considered to be a variety of useful embodiments of the disclosure, it may be to be understood that such detail may be solely for that purposes, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purposes of streamlining the disclosure aiding in the understanding of one or more of the various inventive embodiments. This method of disclosure, however, may be not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±200% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein may be hereby incorporated herein by this reference in its entirety for all purposes, excepting any prosecution file history associated with same, any of same that may be inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A local coil apparatus for performing a magnetic resonance (MR) scanning on a local part of a subject, comprising:
a receiving system including a receiving member assembly, wherein
the receiving member assembly includes a first receiving member and a second receiving member,
the first receiving member includes a first anterior receiving member,
the first anterior receiving member is configured to accommodate the first local part of the subject,
the second receiving member includes a second anterior receiving member and a second posterior receiving member,
the second anterior receiving member and the second posterior receiving member are detachably mounted together to form a portion of an inner space,
each of the first receiving member and the second receiving member includes a first coil assembly configured to receive MR signals during the MR scanning,
the second receiving member includes one or more rotation joints,
the first anterior receiving member rotatably connect to the second anterior receiving member via the one or more rotation joints, and
the first anterior receiving member is rotatable with respect to the second receiving member.

2. The local coil apparatus of claim 1, wherein the first anterior receiving member is detachably plugged in the one or more rotation joints.

3. The local coil apparatus of claim 1, wherein the first coil assembly of the second receiving member includes a first electrical interface that is configured in at least one of the one or more rotation joints.

4. The local coil apparatus of claim 1, wherein
the first receiving member further includes a first posterior receiving member,
the first anterior receiving member and the first posterior receiving member are is configured to form a first portion of the inner space,
the receiving member assembly is configured to change from a first configuration to a second configuration when the first anterior receiving member rotates by an angle, and
the first configuration and the second configuration correspond to different sizes of the first portion of the inner space.

5. The local coil apparatus of claim 4, wherein
the first anterior receiving member includes a flexible component; and
when the receiving member assembly is in the second configuration, the flexible component of the first anterior receiving member undergoes an elastic deformation and is caused to press against at least a portion of the local part.

6. The local coil apparatus of claim 5, wherein at least a portion of the first coil assembly of the first anterior receiving member is disposed inside the flexible component.

7. The local coil apparatus of claim 1, wherein
the first coil assembly of the second posterior receiving member includes a second electrical interface,
the first coil assembly of the second receiving member includes a third electrical interface, and
the second electrical interface is operably coupled to the third electrical interface.

8. The local coil apparatus of claim 4, wherein
the first posterior receiving member includes a flexible component that has two free ends, and
when the local part is placed on the flexible component of the first posterior receiving member, the two free ends move towards each other and conform to at least a portion of the local part.

9. The local coil apparatus of claim 8, wherein a second anterior receiving member of the second receiving member is configured to compress the first posterior receiving member so that the two free ends press against the at least a portion of the local part when the second anterior receiving member is in a closed configuration above a second posterior receiving member of the second receiving member.

10. The local coil apparatus of claim 9, wherein the second anterior receiving member of the second receiving member compresses the first posterior receiving member via an elastic structure.

11. The local coil apparatus of claim 4, wherein the receiving system further includes
an activation member disposed inside the inner space, and
a driving mechanism physically connected to the first posterior receiving member, wherein when the local part is placed on the activation member, the activation member causes the driving mechanism to drive the receiving member assembly to change from a first configuration to a second configuration to reduce a distance between the first posterior receiving member and a portion of the local part.

12. The local coil apparatus of claim 11, wherein the driving mechanism is further connected to the second posterior receiving member physically, wherein when the receiving member assembly changes from the first configuration to the second configuration, a distance between the second posterior receiving member and a portion of the local part is reduced.

13. The local coil apparatus of claim 11, wherein the activation member is set on the first posterior receiving member.

14. A local coil apparatus for performing a magnetic resonance (MR) scanning on a local part of a subject, comprising:
a housing configured to provide an inner space for receiving the local part of the subject; and
a receiving system including a receiving member assembly, the receiving member assembly including a first anterior receiving member, the first anterior receiving member being configured to accommodate the first local part of the subject, the second receiving member including a second anterior receiving member and a second posterior receiving member, the second anterior receiving member and the second posterior receiving member are detachably mounted together to form a portion of an inner space, each of the first anterior receiving member and the first posterior receiving member including a first coil assembly, the first coil assembly being configured to receive MR signals during the MR scanning, the second receiving member including one or more rotation joints, the first anterior receiving member rotatably connecting to the second anterior receiving member via the one or more rotation joints, wherein the first anterior receiving member rotatable with respect to a reference plane so that at least a portion of the first coil assembly of the first anterior receiving member conforms to the local part.

15. The local coil apparatus of claim 14, wherein
the first receiving member further includes a first posterior receiving member,
the first anterior receiving member and the first posterior receiving member are is configured to form a first portion of the inner space,
the receiving member assembly is configured to change from a first configuration to a second configuration when the first anterior receiving member rotates by an angle, and
the first configuration and the second configuration correspond to different sizes of the first portion of the inner space.

16. The local coil apparatus of claim 15, wherein
the first anterior receiving member includes a flexible component, and
when the receiving member assembly is in the second configuration, the flexible component of the first anterior receiving member undergoes an elastic deformation and is caused to press against the local part.

17. A local coil apparatus for performing a magnetic resonance (MR) scanning on the neck and head of a subject, comprising:
a receiving system including a receiving member assembly, wherein
the receiving member assembly includes a neck receiving member and a head receiving member,
the neck receiving member includes an anterior neck receiving member,
the anterior neck receiving member is configured to accommodate the neck of the subject,
the head receiving member includes an anterior head receiving member and a posterior head receiving member,
the anterior head receiving member and the posterior head receiving member are detachably mounted together to form a portion of an inner space,
each of the neck receiving member and the head receiving member includes a first coil assembly configured to receive MR signals during the MR scanning,
the head receiving member includes one or more rotation joints,
the anterior neck receiving member rotatably connect to the anterior head receiving member via the one or more rotation joints, and
the anterior neck receiving member is rotatable with respect to the head receiving member.

\* \* \* \* \*